US010307476B2

(12) United States Patent
Collins et al.

(10) Patent No.: US 10,307,476 B2
(45) Date of Patent: Jun. 4, 2019

(54) GENETICALLY STABLE LIVE ATTENUATED RESPIRATORY SYNCYTIAL VIRUS VACCINE AND ITS PRODUCTION

(71) Applicant: THE UNITED STATES OF AMERICA, AS REPRESENTED BY THE SECRETARY, DEPARTMENT OF HEALTH AND HUMAN SERVICES, Washington, DC (US)

(72) Inventors: Peter L. Collins, Silver Spring, MD (US); Cindy L. Luongo, Bethesda, MD (US); Ursula J. Buchholz, Silver Spring, MD (US); Brian R. Murphy, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 49 days.

(21) Appl. No.: 15/455,438

(22) Filed: Mar. 10, 2017

(65) Prior Publication Data
US 2017/0189520 A1    Jul. 6, 2017

Related U.S. Application Data

(62) Division of application No. 14/394,226, filed as application No. PCT/US2013/030836 on Mar. 13, 2013, now Pat. No. 9,624,475.

(60) Provisional application No. 61/624,010, filed on Apr. 13, 2012.

(51) Int. Cl.
| A61K 39/155 | (2006.01) |
| A61K 39/12 | (2006.01) |
| C07K 14/005 | (2006.01) |
| C12N 7/00 | (2006.01) |
| A61K 39/00 | (2006.01) |

(52) U.S. Cl.
CPC ............ *A61K 39/155* (2013.01); *A61K 39/12* (2013.01); *C07K 14/005* (2013.01); *C12N 7/00* (2013.01); *A61K 2039/5254* (2013.01); *C12N 2760/18521* (2013.01); *C12N 2760/18522* (2013.01); *C12N 2760/18534* (2013.01); *C12N 2760/18562* (2013.01)

(58) Field of Classification Search
None
See application file for complete search history.

(56) References Cited

U.S. PATENT DOCUMENTS

| 5,922,326 A | 7/1999 | Murphy et al. |
| 5,993,824 A | 11/1999 | Murphy et al. |
| 6,713,066 B1 | 3/2004 | Collins et al. |
| 7,709,007 B2 | 5/2010 | Murphy et al. |
| 2005/0100557 A1 | 5/2005 | Collins et al. |

FOREIGN PATENT DOCUMENTS

WO    WO 2001/04335 A2    1/2001

OTHER PUBLICATIONS

"Human respiratory syncytial virus nonstructural protein 1, nonstructural protein 2, nucleocapsid protein, phosphoprotein, matrix protein, small hydrophobic protein, glycoprotein, fusion glycoprotein, 22K/M2 protein and L protein mRNA, complete cds"; Genbank accession No. M74568; 10 pages; as accessed May 19, 2015.
Bartlett et al.; "Attenuation and efficacy of human parainfluenza virus type I (HPIV I) vaccine candidates containing stabilized mutations in the P/C and L genes"; Virology Journal; Jul. 2007; vol. 4; 13 pages.
U.S. Appl. No. 60/047,575, filed May 23, 1997, Murphy et al.
Belshe et al.; "Experimental Respiratory Syncytial Virus Infection of Four Species of Primates"; Journal of Medical Virology; 1977; vol. 1; p. 157-162.
Buchholz et al.; "Chimeric Bovine Respiratory Syncytial Virus with Glycoprotein Gene Substitutions from Human Respiratory Syncytial Virus (HRSV): Effects on Host Range and Evaluation as a Live-Attenuated HRSV Vaccine"; Journal of Virology; Feb. 2000; vol. 74 No. 3; p. 1187-1199.
Buchholz et al.; "Generation of Bovine Respiratory Syncytial Virus (BRSV) from cDNA: BRSV NS2 Is Not Essential for Virus Replication in Tissue Culture, and the Human RSV Leader Region Acts as a Functional BRSV Genome Pomoter"; Journal of Virology; Jan. 1999; vol. 73 No. 1; p. 251-259.
Bukreyev et al.; "Granulocyte-Macrophage Colony-Stimulating Factor Expressed by Recombinant Respiratory Syncytial Virus Attenuates Viral Replication and Increases the Level of Pulmonary Antigen-Presenting Cells"; Journal of Virology; Dec. 2001; vol. 75 No. 24; p. 12128-12140.
Bukreyev et al.; "Interferon γ expressed by a recombinant respiratory syncytial virus attenuates virus replication in mice without compromising immunogenicity"; Proc. Natl. Acad. Sci. USA; Mar. 1999; vol. 96 No. 5; p. 2367-2372.

(Continued)

*Primary Examiner* — Stacy B Chen
(74) *Attorney, Agent, or Firm* — Klarquist Sparkman, LLP

(57) ABSTRACT

Provided herein are recombinant respiratory syncytial viruses that contain mutations that make the disclosed viruses attractive vaccine candidates. The viruses disclosed contain attenuating mutations designed to have increased genetic and phenotypic stability. Desired combinations of these mutations can be made to achieve desired levels of attenuation. Exemplary vaccine candidates are described. Also provided are polynucleotides capable of encoding the described viruses, as wells as methods for producing the viruses and methods of use.

22 Claims, 11 Drawing Sheets
Specification includes a Sequence Listing.

(56) References Cited

OTHER PUBLICATIONS

Bukreyev et al.; Recombinant Respiratory Syncytial Virul from Which the Entire SH Gene Has been Deleted Grows Efficiently in Cell Culture and Exhibits Site-Specific Attenuation in the Respiratory Tract of the Mouse; Journal of Virology; Dec. 1997; vol. 71 No. 12; p. 8973-8982; 1997.
Cheng et al.; "Effective amplification of long targets from cloned inserts and human genomic DNA"; Proc. Natl. Acad. Sci. USA; Jun. 1994; vol. 91; p. 5695-5699.
Collins et al.; "Gene overlap and site-specific attenuation of transcription of the viral polymerase L gene of human respiratory syncytial virus"; Proc. Natl. Acad. Sci. USA; Aug. 1987; vol. 84; p. 5134-5138.
Collins et al.; "New Generation Live Vaccines against Human Respiratory Syncytial Virus Designed by Reverse Genetics"; Proceedings of the American Thoracic Society; 2005; vol. 2 No. 2; p. 166-173.
Collins et al.; "Nucleotide sequences for the gene junctions of human respiratory syncytial virus reveal distinctive features of intergenic structure and gene order"; Proc. Natl. Acad. Sci. USA; Jul. 1986; vol. 83; p. 4594-4598.
Collins et al.; "Production of infectious human respiratory syncytial virus from cloned cDNA confirms an essential role for the transcription elongation factor from the 5' proximal open reading frame of the M2 mRNA in gene expression and provides a capability for vaccine development"; Proc. Natl. Acad. Sci. USA; Dec. 1995; vol. 92; p. 11563-11567.
Collins et al.; "Progress in understanding and controlling respiratory syncytial virus: Still crazy after all these years"; Virus Research; Dec. 2011; vol. 162; p. 80-99.
Connors et al.; "A Cold-Passaged, Attenuated Strain of Human Respiratory Syncytial Virus Contains Mutations in the F and L Genes"; Virology; 1995; vol. 208; p. 478-484.
Crowe et al.; "A comparison in chimpanzees of the immunogenicity and efficacy of live attenuated respiratory syncytial virus (RSV) temperature-sensitive mutant vaccines and vaccinia virus recombinants that express the surface glycoproteins of RSV"; Vaccine; 1993; vol. 11 Issue 14; p. 1395-1404.
Crowe et al.; "A further attenuated derivative of a cold-passaged temperature-sensitive mutant of human respiratory syncytial virus retains immunogenicity and protective efficacy against wild-type challenge in seronegative chimpanzees"; Vaccine; 1994; vol. 12 Issue 9; p. 783-790.
Crowe et al.; "Acquisition of the ts Phenotype by a Chemically Mutagenized Cold-passaged Human Respiratory Syncytial Virus Vaccine Candidate Results from the Acquisition of a Single Mutation in the Polymerase (L) Gene"; Virus Genes; 1996; vol. 13 No. 3; p. 269-273.
Crowe et al.; "Satisfactorily attenuated and protective mutants derived from a partially attenuated cold-passaged respiratory syncytial virus mutant by introduction of additional attenuating mutations during chemical mutagenesis"; Vaccine; 1994; vol. 12 Issue 8; p. 691-699.
Durbin et al; "Recovery of Infectious Human Parainfluenza Virus Type 3 from cDNA"; Virology; Sep. 1997; vol. 235 Issue 2; p. 323-332.
Firestone et al.; "Nucleotide Sequence Analysis of the Respiratory Syncytial Virus Subgroup A Cold-Passaged (cp) Temperature Sensitive (ts) cpts-248/404 Live Attenuated Virus Vaccine Candidate"; Virology; 1996; vol. 225 No. 2; p. 419-422.
Friedewald et al.; "Low-Temperature-Grown RS Virus in Adult Volunteers"; Journal of the American Medical Association; May 1968; vol. 204 Nov. 8; p. 690-694.
Gharpure et al.; "Temperature-sensitive Mutants of Respiratory Syncytial Virus"; Journal of Virology; Apr. 1969; vol. 3 No. 4; p. 414-421.
Hall et al.; "Cold-passaged human parainfluenza type 3 viruses contain ts and non-ts mutations leading to attenuation in rhesus monkeys"; Virus Research; Mar. 1992; vol. 22 Issue 3; p. 173-184.
Haller et al.; "A Single Amino Acid Substitution in the Viral Polymerase Creates a Temperature-Sensitive and Attenuated Recombinant Bovine Parainfluenze Virus Type 3"; Virology; 2001; vol. 288; p. 342-350.
Hoffman et al.; "An infectious clone of human parainfluenza virus type 3"; Journal of Virology; Jun. 1997; vol. 71 No. 6; p. 4272-4277.
Hsu et al.; "Isoalation and characterization of a highly attenuated respiratory syncytial virus (RSV) vaccine candidate by mutagenesis of the incompletely attenuated RSV A2 ts-1 NG-1 mutant virus"; Vaccine; 1995; vol. 13 Issue 5; p. 509-515.
International Search Report and Written Opinion for PCT Application No. PCT/US2013/030836, by the European Patent Office acting as International Searching Authority, dated Aug. 13, 2013, 24 pages.
Juhasz et al.; "The Major Attenuating Mutations of the Respiratory Syncytial Virus Vaccine Candidate cpts530/1009 Specify Temperature-Sensitive Defects in Transcription and Replication and a Non-Temperature-Sensitive Alteration in mRNA Termination"; Journal of Virology; Jun. 1999; vol. 73 No. 6; p. 5176-5180.
Juhasz et al.; "The temperature-sensitive (ts) phenotype of a cold-passaged (cp) live attenuated respiratory syncytial virus vaccine candidate, designated cpts530, results from a single amino acid substitution in the L protein"; Journal of Virology; Aug. 1997; vol. 71 No. 8; p. 5814-5819.
Juhasz et al.; "The two amino acid substitutions in the L protein of cpts530/1009, a live-attenuated respiratory syncytial virus candidate vaccine, are independent temperature-sensitive and attenuation mutations"; Vaccine; Mar. 1999; vol. 17; p. 1416-1424.
Karron et al.; "Identification of a Recombinant Live Attenuated Respiratory Syncytial Virus Vaccine Candidate That is Highly Attenuated in Infants"; The Journal of Infectious Diseases; 2005; vol. 191; p. 1093-1104.
Kato et al.; "The paramyxovirus, Sendai virus, V protein encodes a luxury function required for viral pathogenesis"; The EMBO Journal; 1997; vol. 16 No. 3; p. 578-587.
Krempl et al.; "Recombinant Respiratory Syncytial Virus with the G and F Genes Shifted to the Promoter-Proximal Positions"; Journal of Virology; Dec. 2002; vol. 76 No. 23; p. 11931-11942.
Lin et al.; "Genetic stability determinants of temperature sensitive, live attenuated respiratory syncytial virus vaccine candidates"; Virus Research; 2006; vol. 115; p. 9-15.
Luongo et al.; "Codon stabilization analysis of the "248" temperature sensitive mutation for increased phenotypic stability of respiratory syncytial virus vaccine candidates"; Vaccine; Sep. 2009; vol. 27 Issue 41; p. 5667-5676.
Luongo et al.; "Increased Genetic and Phenotypic Stability of a Promising Live-Attenuated Respiratory Syncytial Virus Vaccine Candidate by Reverse Genetics"; Journal of Virology; Oct. 2012; vol. 86 No. 19; p. 10792-10804.
Luongo et al.; Respiratory virus modified by deletions of the NS2 gene and amino acid S1313 of the L polymerase protein is a temperature sensitive live-attenuated vaccine candidate that is phenotypically stable at physiological temperature; American Society of Microbiology; Dec. 2012.
McAuliffe et al.; "Codon Substitution Mutations at Two Positions in the L Polymerase Protein of Human Parainfluenza Virus Type 1 Yield Viruses with a Spectrum of Attenutation In Vivo and Increased Phenotypic Stability In Vitro"; Journal of Virology; Feb. 2004; vol. 78 No. 4; p. 2029-2036.
Mink et al.; "Nucleotide sequence of the 3' leader and 5' trailer regions of human respiratory syncytial virus genomic RNA"; Virology; Dec. 1991; vol. 185 Issue 2; p. 615-624.
Murphy et al.; "Enhanced pulmonary histopathology is observed in cotton rats immunized with formalin-inactivated respiratory syncytial virus (RSV) or purified F glycoprotein and challenged with RSV 3-6 months afer immunization"; Vaccine; Oct. 1990; vol. 8 Issue 5; p. 497-502.
Nolan et al.; "Recombinant human parainfluenza virus type 2 vaccine candidates containing a 3' genomic promoter mutation and L polymerase mutations are attenuated and protective in non-human primates"; Vaccine; Aug. 2007; vol. 25 Issue 34; p. 6409-6422.

(56) References Cited

OTHER PUBLICATIONS

Poch et al.; "Identification of four conserved motifs among the RNA-dependent polymerase encoding elements"; The EMBO Journal; 1989; vol. 8 No. 12; p. 3867-3874.

Poch et al.; "Sequence comparison of five polymerases (L proteins) of unsegmented negative-strand RNA viruses: theoretical assignment of functional domains"; Journal of General Virology; 1990; vol. 71; p. 1153-1162.

Samal et al.; "RNA replication by a respiratory syncytial virus RNA analog does not obey the rule of six and retains a nonviral trinucleotide extension at the leader end"; Journal of Virology; Aug. 1996; vol. 70 No. 8; p. 5075-5082.

Skiadopoulos et al.; "Three Amino Acid Substitutions in the L Protein of the Human Parainfluenza Virus Type 3 cp45 Live Attenuated Vaccine Candidate Contribute to Its Temperature-Sensitive and Attenuation Phenotypes"; Journal of Virology; Mar. 1998; vol. 72 No. 3; p. 1762-1768.

Spann et al.; "Effects of Nonstructural Proteins NS1 and NS2 of Human Respiratory Syncytial Virus on Interferon Regulatory Factor 3, NF-kB, and Proinflammatory Cytokines"; Journal of Virology; May 2005; vol. 79 No. 9; p. 5353-5362.

Stec et al.; "Sequence Analysis of the Polymerase L Gene of Human Respiratory Syncytial Virus and Predicted Phylogeny of Nonsegmented Negative-Strand Viruses"; Virology; Jul. 1991; vol. 183 Issue 1; p. 273-287.

Teng et al.; "Contribution of the Respiratory Syncytial Virus G Glycoprotein and Its Secreted and Membrane-Bound Forms to Virus Replication in Vitro and in Vivo"; Virology; Oct. 2001; vol. 289 Issue 2; p. 283-296.

Teng et al.; Recombinant Respiratory Syncytial Virus That Does Not Express the NS1 or M2-2 Protein Is Highly Attenuated and Immunogenic in Chimpanzees; Journal of Virology; Oct. 2000; vol. 74 No. 19; p. 9317-9321.

Whitehead et al.; "A Replacement of the F and G Proteins of Respiratory Syncytial Virus (RSV) Subgroup A with Those of Subgroup B Generates Chimeric Live Attenuated RSV Subgroup B Vaccine Candidates"; Journal of Virology; Dec. 1999; vol. 73 No. 12; p. 9773-9780.

Whitehead et al.; "A Single Nucleotide Substitution in the Transcription Start Signal of the M2 Gene of Respiratory Syncytial Virus Vaccine Candidate cpts248/404 Is the Major Determinant of the Temperature-Sensitive and Attenuation Phenotypes"; Virology; Aug. 1998; vol. 247 Issue 2; p. 232-239.

Whitehead et al.; "Addition of Missense Mutation Present in the L Gene of Respiratory Syncytial (RSV) cpts530/1030 to RSV Vaccine Candidate cpts248/404 Increases Its Attenuation and Temperature Sensitivity"; Journal of Virology; Feb. 1999; vol. 73 No. 2; p. 871-877.

Whitehead et al.; "Recombinant Respiratory Syncytial Virus (RSV) Bearing a Set of Mutations from Cold-Passaged RSV Is Attenuated in Chimpanzee"; Journal of Virology; May 1998; vol. 72 No. 5; p. 4467-4471.

Whitehead et al.; "Recombinant Respiratory Syncytial Virus Bearing a Deletion of either the NS2 of SH Gene is Attenuated in Chimpanzees"; Journal of Virology; Apr. 1999; vol. 73 No. 4; p. 3438-3442.

Witko et al.; "An Efficient helper-virus-free method for rescue of recombinant paramyxoviruses and rhadoviruses from a cell line suitable for vaccine development"; Journal of Virological Methods; Jul. 2006; vol. 135 Issue 1; p. 91-101.

Wright et al.; "Genetic Studies of Respiratory Syncytial Virus Temperature-Sensitive Mutants"; Arch. Ges. Virusforsch.; 1973; vol. 41; p. 238-247.

Wright et al.; "The Interferon Antagonist NS2 Protein of Respiratory Syncytial Virus is an Important Virulence Determinant for Humans"; The Journal of Infectious Diseases; 2006; vol. 193; p. 573-581.

Wyatt et al.; "Replication-Deficient Vaccinia Virus Encoding Bacteriophage T7 RNA Polymerase for Transient Gene Expression in Mammalian Cells"; Virology; 1995; vol. 210; p. 202-205.

Zhou et al.; "Increased pathogenesis and inflammation of airways from respiratory syncytial virus infection in T cell deficient nude mice"; Medical Microbiology and Immunology; Dec. 2008; vol. 197 Issue 4; p. 345-351.

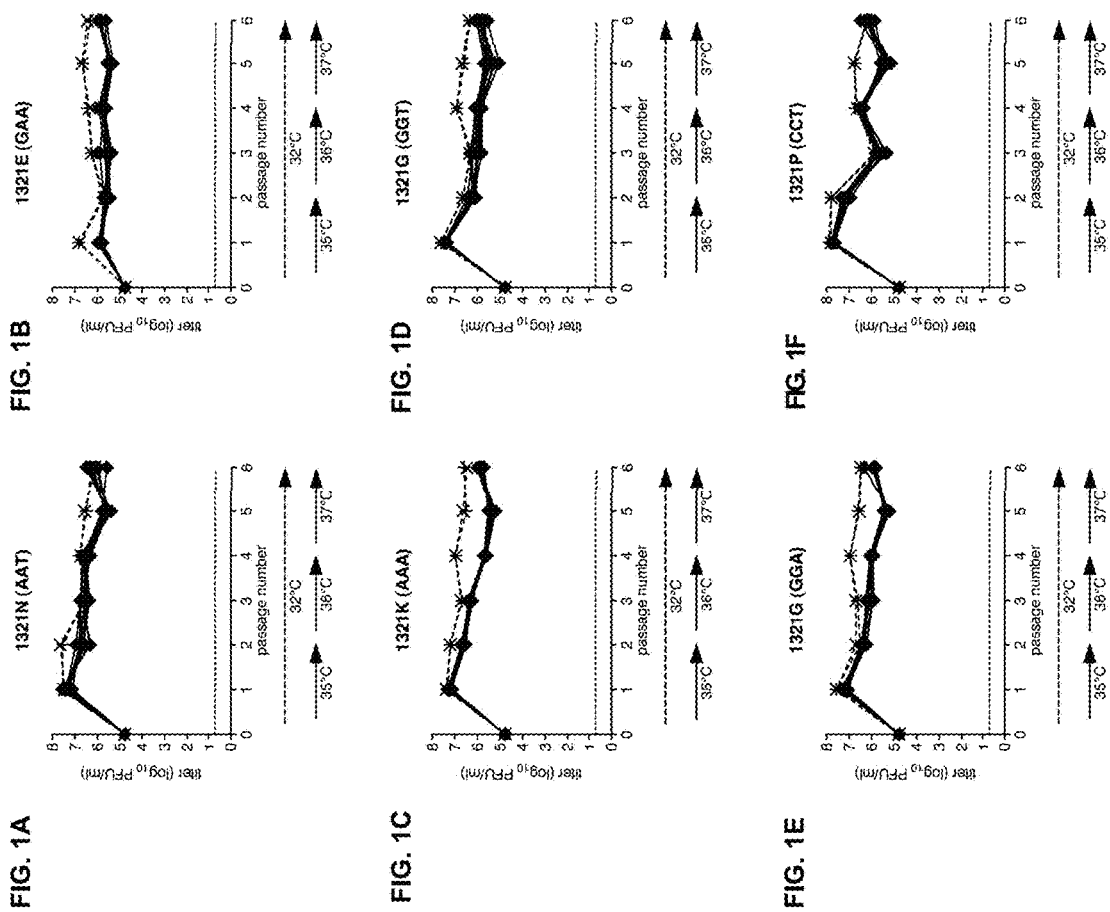

| SEQ ID NO: | | nt # | 12422 | | | 12434-6 | | | | | | | | | 12458-60 | | | |
|---|---|---|---|---|---|---|---|---|---|---|---|---|---|---|---|---|---|---|
| 1 11 | | wt RSV | ATG M | GAA E | GAA E | CTC L | AGC S | ATA I | GGA G | ACC T | CTT L | GGG G | TTA L | ACA T | TAT Y | GAA E | AAG K |
| 2 12 | | Y1321/ 1313C | ... | ... | ... | T.. ░ | | ... | ... | ... | ... | ... | ... | ... | ... | ... | ... |
| 3 13 | | 1321E(GAA)/ S1313 | ... | ... | ... | ... | ... | ... | ... | ... | ... | ... | ... | ... | G.A ░ | ... | ... |
| 4 14 | | 1321E(GAA)/ 1313C | ... | ... | ... | T.. ░ | | ... | ... | ... | ... | ... | ... | ... | G.A ░ | ... | ... |
| 5 15 | | 1321K(AAA)/ S1313 | ... | ... | ... | ... | ... | ... | ... | ... | ... | ... | ... | ... | A.A ░ | ... |

FIG. 3A

|  | | | | | | | | | | | | | SEQ ID NO: |
|---|---|---|---|---|---|---|---|---|---|---|---|---|---|
| | 12428 | | | | | | | | | | 12463 | | |
| Wt RSV | GAA CTC AGC ATA GGA ACC CTT GGG TTA ACA TAT GAA ... | | | | | | | | | | | | 1 |
| | E L S I G T L G L T Y E ... | | | | | | | | | | | | 11 |
| 1321K(AAA) + S1313(TCA) | . . TCA . . . . . . . . A.A . ... | | | | | | | | | | | | 19 |
| | . . . . . . . . . . . K . ... | | | | | | | | | | | | 15 |
| | second site mutation aa 1313 | | | | | | | | | | original "1030" mutation aa 1321 | | |

FIG. 3B

1321K(AAA)/S1313(TCA)

[Graph: titer (log₁₀ PFU/ml) vs passage number, showing temperature shifts 37°C → 32°C → 38°C]

```
nt #        12422                 12434-6                        12458-60
wt RSV      ATG GAA GAA CTC AGC ATA GGA ACC CTT GGG TTA ACA TAT GAA AAG ....    SEQ ID NO: 1
             M   E   E   L   S   I   G   T   L   G   L   T   Y   E   K  ....              11

Δ1313                       ---                                                             20
                                                                                            21 aa #        1309                    1313                              1321
                                     ↑                                 ↑
                                second                              site of
                                site                               "1030" mutation
                                "1313" mutation
```

Δ1313

| | | | 1313 | 1314 | | 1316 | | | | 1320 | SEQ ID NO: |
|---|---|---|---|---|---|---|---|---|---|---|---|
| | E | L | S | I | G | T | L | G | L | T | 11 |
| rA2 | GAA | CTC | AGC | ATA | GGA | ACC | CTT | GGG | TTA | ACA | 1 |
| | E | L | Δ | I | G | T | L | G | L | T | 21 |
| Δ1313 | GAA | CTC | --- | ATA | GGA | ACC | CTT | GGG | TTA | ACA | 20 |
| | E | L | Δ | T | G | T | L | G | L | T | 26 |
| Δ1313/1314T | GAA | CTC | --- | ACA | GGA | ACC | CTT | GGG | TTA | ACA | 27 |
| | E | L | Δ | L | G | T | L | G | L | T | 28 |
| Δ1313/1314L(CTG) | GAA | CTC | --- | CTG | GGA | ACC | CTT | GGG | TTA | ACA | 29 |
| | E | L | S | Δ | G | T | L | G | L | T | 30 |
| Δ1314 | GAA | CTC | AGC | --- | GGA | ACC | CTT | GGG | TTA | ACA | 31 |
| | E | L | S | I | G | Δ | L | G | L | T | 32 |
| Δ1316 | GAA | CTC | AGC | ATA | GGA | --- | CTT | GGG | TTA | ACA | 33 |
| | E | L | S | I | G | T | L | G | L | Δ | 34 |
| Δ1320 | GAA | CTC | AGC | ATA | GGA | ACC | CTT | GGG | TTA | --- | 35 |

FIG. 10

RSV L protein amino acid 1 — N — I — II — III — IV — V — VI — C — amino acid 2165

- Q831L "248" (polymerase activity)
- Y1321N "1030" (capping)
- hinge region: aa 1744-1764
- VI (MTase)

| | | SEQ. ID NO: |
|---|---|---|
| 1754ΔS | PLLSNKKLIKSSAMIRTNYSK | 36 |
| 1756ΔA | PLLSNKKLIK--SAMIRTNYSK | 37 |
| 1753ΔKS | PLLSNKKLIKSS--MIRTNYSK | 38 |
| 1754ΔSS | PLLSNKKLI--SAMIRTNYSK | 39 |
| 1755ΔSA | PLLSNKKLIKS--AMIRTNYSK | 40 |
| 1753ΔKSSA | PLLSNKKLI----MIRTNYSK | 41 |
| 1754ΔSSAM | PLLSNKKLIK----MIRTNYSK | 42 |
| 1752Δ6aa | PLLSNKKLI-----IRTNYSK | 43 |
| 1749Δ9aa | PLLSN--------IRTNYSK | 44 |
| 1752Δ13aa | PLLSNKKL--------IRTNYSK | 45 |
| 1744Δ14aa | ---------IRTNYSK | 46 |
| 1744Δ21aa | PLLSNKKL-------- | 47 |
| | --------- | 48 |

FIG. 11

GENETICALLY STABLE LIVE ATTENUATED RESPIRATORY SYNCYTIAL VIRUS VACCINE AND ITS PRODUCTION

CROSS REFERENCE TO RELATED APPLICATIONS

This application is a divisional of U.S. application Ser. No. 14/394,226, filed Oct. 13, 2014, which is the National Stage of International Application No. PCT/US2013/030836, filed Mar. 13, 2013, which in turn claims the benefit of U.S. Provisional Appl. No. 61/624,010, filed Apr. 13, 2012, the contents of each of these applications is specifically incorporated by reference herein in its entirety.

TECHNICAL FIELD

The subject matter disclosed herein relates to paramyxoviruses, in particular, respiratory syncytial virus and attenuated, mutant strains thereof.

BACKGROUND

Human respiratory syncytial virus (RSV) infects nearly everyone worldwide early in life and is responsible for considerable mortality and morbidity. In the United States alone, RSV is responsible for 75,000-125,000 hospitalizations yearly, and worldwide conservative estimates conclude that RSV is responsible for 64 million pediatric infections and 160,000 pediatric deaths. Another unusual feature of RSV is that severe infection in infancy can be followed by years of airway dysfunction, including a predisposition to airway reactivity. RSV infection exacerbates asthma and may be involved in initiating asthma.

RSV is a member of the Paramyxoviridae family and, as such, is an enveloped virus that replicates in the cytoplasm and matures by budding through the host cell plasma membrane. The genome of RSV is a single, negative-sense strand of RNA of 15.2 kilobases that is transcribed by the viral polymerase into 10 mRNAs by a sequential stop-start mechanism that initiates at a single viral promoter at the 3' end of the genome. Each mRNA encodes a single major protein, with the exception of the M2 mRNA, which has two overlapping open reading frames that encode two separate proteins. The 11 RSV proteins are: the RNA-binding nucleocapsid protein (N), the phosphoprotein (P), the large polymerase protein (L), the attachment glycoprotein (G), the fusion protein (F), the small hydrophobic (SH) surface glycoprotein, the internal matrix protein (M), the two nonstructural proteins NS1 and NS2, and the M2-1 and M2-2 proteins encoded by the M2 mRNA. The RSV gene order is: 3'-NS1-NS2-N-P-M-SH-G-F-M2-L. Each gene is flanked by short transcription signals called the gene-start (GS) signal, present on the upstream end of the gene and involved in initiating transcription of the respective gene, and the gene-end (GE) signal, present at the downstream end of the gene and involved in directing synthesis of a polyA tail followed by release of the mRNA.

The development of live-attenuated vaccines has been in progress since the 1960's but has been complicated by a number of factors. For example, RSV grows only to moderate titers in cell culture and is often present in long filaments that are difficult to purify and can readily lose infectivity during handling. Another problem is that the magnitude of the protective immune response is roughly proportional to the extent of virus replication (and antigen production). Thus, attenuation is accompanied by a reduction in immunogenicity, and it is essential to identify a level of replication that is well tolerated yet satisfactorily immunogenic. These studies can only be done in humans, because RSV does not replicate efficiently in most experimental animals, such as rodents and monkeys. Chimpanzees are more permissive but usually are not readily available. Another obstacle is the difficulty in developing attenuating mutations. Another obstacle is genetic instability that is characteristic of RNA viruses, whereby attenuating mutations can revert to the wild-type assignment or to an alternative assignment that confers a non-attenuated phenotype.

Until recently, RSV vaccine candidates were developed by conventional biological means. These previous biologically-derived candidates were either under-attenuated or over-attenuated, and genetic instability was observed in some cases.

SUMMARY

Disclosed herein are particular mutations useful, either individually or in combinations that may include other known mutations, in producing recombinant, attenuated strains of respiratory syncytial virus that have improved genetic and phenotypic stability, which are useful features for live vaccine viruses. For example, recombinant RSV strains of the invention provide a level of attenuation that was similar to that of a promising experimental live-attenuated RSV vaccine that was well-tolerated and immunogenic in young infants (Karron et al JID 191:1093-104, 2005); however, the present vaccines exhibited increased genetic stability. This can involve the use of an alternate amino acid assignment at specified positions, or of a different codon encoding the same amino acid assignment. In some aspects, the recombinant viruses disclosed herein include a mutation in the codon encoding amino acid residue 1321 of the RSV L protein (the 1321 codon), a position that was previously found to be unstable in attenuated RSV evaluated in clinical trials (Karron et al JID 191:1093-104, 2005). Certain substitutions imparted increased stability at residue 1321. Unexpectedly, this was associated with increased instability at a novel site, namely L amino acid residue 1313. Thus, in some aspects, the recombinant viruses disclosed herein include alternative codons encoding amino acid residue 1313 of the RSV L protein (the 1313 codon). Used in combination, certain codons at positions 1321 and 1313 imparted increased genetic and phenotypic stability to both sites. In some embodiments disclosed herein the 1313 codon may be deleted altogether to create a deletion mutant strain (e.g. RSV Δ1313). Specific attenuated recombinant viruses are described that bear desired combinations of mutations including ones at codons 1321, 1313, and 1314 of the L protein, in combination with other point mutations and/or gene-deletion mutations. Other recombinant viruses include RSV having a mutation in one or more of the codons that encode amino acid residues 1744-1764, including a number of codon deletions involving 1 or 2 or several contiguous amino acids from this region, or as many as 13, 14, or 21 contiguous amino acids. Further, disclosed herein are recombinant RSVs having a mutation or deletion of the codon encoding the amino acid residue at position 1316 of the RSV L protein. Also described is recombinant virus bearing deletion of position 1314 in the L protein. The recombinant respiratory syncytial virus particles disclosed herein can comprise a genome that encodes nonstructural protein 1 (NS1), nonstructural protein 2 (NS2), nucleocapsid protein (N), phosphoprotein (P), matrix protein (M), small hydrophobic protein (SH), glycoprotein (G), fusion protein (F), protein M2-1, protein M2-2, and a mutated large polymerase protein (L); however, those skilled in the art will understand that not all of these proteins, or genes corresponding thereto, need be included for an RSV to be infectious.

Disclosed herein are recombinant RSVs having a mutation in the codon encoding amino acid residue 1321 of the RSV L protein. The 1321 codon can be mutated to cause the amino acid corresponding to the tyrosine at position 1321 of the RSV L protein to be any naturally occurring amino acid other that asparagine (N). In some embodiments, the 1321 codon can be mutated to cause the amino acid corresponding to the tyrosine at position 1321 of the RSV L protein to be alanine. In some embodiments, the 1321 codon can be mutated to cause the amino acid corresponding to the tyrosine at position 1321 of the RSV L protein to be aspartic acid. In some embodiments, the 1321 codon can be mutated to cause the amino acid corresponding to the tyrosine at position 1321 of the RSV L protein to be cysteine. In some embodiments, the 1321 codon can be mutated to cause the amino acid corresponding to the tyrosine at position 1321 of the RSV L protein to be glutamic acid. In some embodiments, the 1321 codon can be mutated to cause the amino acid corresponding to the tyrosine at position 1321 of the RSV L protein to be glutamine. In some embodiments, the 1321 codon can be mutated to cause the amino acid corresponding to the tyrosine at position 1321 of the RSV L protein to be glycine. In some embodiments, the 1321 codon can be mutated to cause the amino acid corresponding to the tyrosine at position 1321 of the RSV L protein to be histidine. In some embodiments, the 1321 codon can be mutated to cause the amino acid corresponding to the tyrosine at position 1321 of the RSV L protein to be isoleucine. In some embodiments, the 1321 codon can be mutated to cause the amino acid corresponding to the tyrosine at position 1321 of the RSV L protein to be leucine. In some embodiments, the 1321 codon can be mutated to cause the amino acid corresponding to the tyrosine at position 1321 of the RSV L protein to be lysine. In some embodiments, the 1321 codon can be mutated to cause the amino acid corresponding to the tyrosine at position 1321 of the RSV L protein to be methionine. In some embodiments, the 1321 codon can be mutated to cause the amino acid corresponding to the tyrosine at position 1321 of the RSV L protein to be phenlyalanine. In some embodiments, the 1321 codon can be mutated to cause the amino acid corresponding to the tyrosine at position 1321 of the RSV L protein to be proline. In some embodiments, the 1321 codon can be mutated to cause the amino acid corresponding to the tyrosine at position 1321 of the RSV L protein to be serine. In some embodiments, the 1321 codon can be mutated to cause the amino acid corresponding to the tyrosine at position 1321 of the RSV L protein to be threonine. In some embodiments, the 1321 codon can be mutated to cause the amino acid corresponding to the tyrosine at position 1321 of the RSV L protein to be tryptophan. In some embodiments, the 1321 codon can be mutated to cause the amino acid corresponding to the tyrosine at position 1321 of the RSV L protein to be tyrosine. In some embodiments, the 1321 codon can be mutated to cause the amino acid corresponding to the tyrosine at position 1321 of the RSV L protein to be valine. Furthermore, the 1321 codon can be mutated to cause the amino acid corresponding to the tyrosine at position 1321 of the RSV L protein to be any non-naturally occurring amino acid. In addition, it is contemplated that the disclosed recombinant RSVs having a mutated 1321 codon may also include additional mutations including, but not limited to, mutations including cold passage ("cp") mutations, temperature sensitive ("ts") mutations, and deletion of part or all of one or more genes. The recombinant RSVs modified at codon 1321 may exhibit temperature sensitive growth characteristics or attenuated replication in vivo or in vitro. Additionally the described viruses may exhibit both temperature sensitive growth characteristics and attenuated replication in vivo or in vitro. In view of the degeneracy of the genetic code, it should be understood by those skilled in the art that the 1321 codon can be mutated at any or all of the three nucleotide positions making up the codon to encode any of the substituted amino acid residues described herein. Furthermore, a strategy whereby more than one such nucleotides of the codon is altered in order to produce a mutated amino acid residue at position 1321 of the RSV L protein can be employed in order to stabilize the mutation and reduce the likelihood that the altered 1321 codon will revert to its original amino acid assignment or undergo a further mutation, by natural mutation processes, to an undesirable amino acid residue. It should also be noted that many of the codons specifically described herein are referred to using DNA base pairs as they would appear in a positive-sense orientation; however, it should be apparent that to one skilled in the art that corresponding mutations, alterations, or modifications could be made in an analogous manner for negative-sense DNA codons, or positive or negative-sense RNA codons.

Disclosed herein are recombinant RSVs having a mutation in the codon encoding amino acid residue 1313 of the RSV L protein. The 1313 codon can be mutated to cause the amino acid corresponding to the serine at position 1313 of the RSV L protein to be a serine residue encoded by a different codon. In some embodiments described herein, the naturally occurring serine codon may be changed from AGC to AGT. In some embodiments described herein, the naturally occurring serine codon may be changed from AGC to TCT. In some embodiments described herein, the naturally occurring serine codon may be changed from AGC to TCC. In some embodiments described herein, the naturally occurring serine codon may be changed from AGC to TCA. In some embodiments described herein, the naturally occurring serine codon may be changed from AGC to TCG. Alternatively, the 1313 codon can be mutated to cause the amino acid corresponding to the serine at position 1313 of the RSV L protein to be a different amino acid. For example, in some embodiments, the 1313 codon is mutated to encode cysteine. In this instance, the encoded cysteine residue can be encoded by any corresponding codon (e.g., TGT or TGC). In some embodiments described herein, the 1313 codon is deleted entirely to produce an RSV that has, or can encode, an L protein having at least one fewer amino acid that the wild-type L protein. The recombinant RSVs modified at codon 1313 may exhibit temperature sensitive growth characteristics or attenuated replication in vivo or in vitro. Additionally the described recombinant viruses may exhibit both temperature sensitive growth characteristics and attenuated replication in vivo or in vitro. In view of the degeneracy of the genetic code, it should be understood by those skilled in the art that the 1313 codon can be mutated at any or all of the three nucleotide positions making up the codon to encode any of the substituted amino acid residues described herein. Furthermore, a strategy whereby more than one such nucleotides of the codon is altered in order to produce a mutated amino acid residue at position 1313 of the RSV L protein can be employed in order to stabilize the mutation and prevent the altered 1313 codon from reverting or undergoing a further mutation, by natural mutation processes, to an undesirable amino acid residue. It should also be noted that many of the codons specifically described herein are referred to using DNA base pairs as they would appear in a positive-sense orientation; however, it should be apparent that to one skilled in the art that corresponding mutations, alterations, or modifications could be made in an analogous manner for negative-sense DNA codons, or positive or negative-sense RNA codons.

Another RSV mutation described herein occurs at amino acid residue 649 of the RSV L protein. In some embodiments, the codon encoding glutamic acid at position 649 of the RSV L protein is mutated to cause a different amino acid to be encoded at this position. In some embodiments, the codon is mutated to encode an amino acid with a charged side chain. In one embodiment, the codon is mutated to encode aspartic acid at position 649 of the RSV L protein. Based on this disclosure, those skilled in the art will readily understand that a mutation at position 649 of the L protein may be combined with any number of RSV mutant strains in order to enhance the attenuation or stability of the virus. For example, E649D may be combined with a mutation at position 1321 of the L protein, a mutation at position 1313 of the L protein, or may be used with mutations at both positions 1321 and 1313. In one embodiment, the mutation E649D may be combined with the mutations 1321K(AAA) and S1313(TCA) to give rise to RSV strain 1321K(AAA)/S1313(TCA)+E649D. As used herein, amino acids are referred to according to their standard one-letter or three-letter abbreviations, as is well known in the art: Alanine, Ala, A; Arginine, Arg, R; Asparagine, Asn, N; Aspartate, Asp, D; Cysteine, Cys, C; Glutamate, Glu, E; Glutamine, Gln, Q; Glycine, Gly, G; Histidine, His, H; Isoleucine, Ile, I; Leucine, Leu, L; Lysine, K; Methionine, Met, M; Phenylalanine, Phe, F; Proline, Pro, P; Serine, Ser, S; Threonine, Thr, T; Trpytophan, Trp, W; Tyrosine, Tyr, Y; Valine, Val, V.

Another attenuating RSV mutation described herein occurs at amino acid residue 874 of the RSV L protein. Accordingly, provided in this disclosure are recombinant RSVs having a L protein, a P protein, a N protein, a M2-1 protein, and a genome or antigenome with a mutation or a deletion of the codon encoding glutamine at a position corresponding to position 874 of the L protein. In some embodiments the genome or antigenome of such RSVs optionally encode a NS1 protein, a NS2 protein, a G protein, a F protein, M protein and an SH protein. In some embodiments, the codon encoding glutamine at position 874 of the RSV L protein is mutated to cause a different amino acid to be encoded at this position. In some embodiments, the codon is mutated to encode an amino acid with a charged side chain. In one embodiment, the codon is mutated to encode histidine at position 874 of the RSV L protein. Based on this disclosure, those skilled in the art will readily understand that a mutation at position 874 of the L protein may be combined with any number of previously described RSV mutant strains in order to enhance the attenuation or stability of the virus. For example, Q874H may be combined with a mutation at position 1321 of the L protein, a mutation at position 1313 of the L protein, or may be used with mutations at both positions 1321 and 1313. In one embodiment, the mutation Q874H may be combined with the mutations 1321K(AAA) and S1313(TCA) to give rise to RSV strain 1321K(AAA)/S1313(TCA)+Q874H.

Also described herein are recombinant RSVs having a mutated 1313 codon and a mutated 1321 codon. In some embodiments, the 1313 codon is changed to a encode serine using a different codon thereby making it less likely that a virus also bearing a 1321 mutation will undergo a serine to cystine mutation at position 1313. In some embodiments the 1313 codon may be changed from AGC to AGT. In some embodiments described herein, the naturally occurring serine codon may be changed from AGC to TCT. In some embodiments described herein, the naturally occurring serine codon may be changed from AGC to TCC. In some embodiments described herein, the naturally occurring serine codon may be changed from AGC to TCA. In some embodiments described herein, the naturally occurring serine codon may be changed from AGC to TCG.

Also provided are isolated infectious respiratory syncytial virus particles comprising a genome that encodes nonstructural protein 1 (NS1), nonstructural protein 2 (NS2), nucleocapsid protein (N), phosphoprotein (P), matrix protein (M), small hydrophobic protein (SH), glycoprotein (G), fusion protein (F), protein M2-1, protein M2-2, and large polymerase protein (L) with a mutation of at least one of the nucleotides of the codon that encodes amino acid 1321 of the L protein. Mutant virus strains of this sort may comprise nucleotide sequence alterations that result in a coding change at amino acid 1321 of the L protein such that the encoded amino acid is a lysine (K) or a glycine (G). In other embodiments described herein, one or more of the NS1, NS2, N, P, M, SH, G, F, M2-1, M2-2 proteins can be altered so as to prevent its expression. For example, the alteration could include deleting the gene in whole or in part, altering the gene via the insertion of a stop codon, removing the gene start sequence for the gene, or any other of a variety of such strategies known in the art.

The individual mutations provided herein are capable of being combined with other mutations, or used in conjunction with other mutagenesis strategies, to create attenuated viruses. In some embodiments, the genome, or corresponding antigenome, of the isolated infectious respiratory syncytial viruses described herein can be manipulated to encode a heterologous gene. For example, the heterologous gene could be a corresponding gene from a related virus, such as parainfluenza virus (PIV), including bovine, mouse, or human PIV subtypes, or metapneumovirus (MPV), such as human MPV, or a heterologous strain of RSV, such as from the heterologous B subgroup, that replaces the gene encoding nonstructural protein 1 (NS1), nonstructural protein 2 (NS2), nucleocapsid protein (N), phosphoprotein (P), matrix protein (M), small hydrophobic protein (SH), glycoprotein (G), fusion protein (F), protein M2-1 or protein M2-2. In addition, a heterologous gene could be added to the genome, so as not to necessitate the removal of any endogenous RSV genes. In related embodiments, a heterologous gene can encode an immunomodulatory protein, such as a cytokine.

Also provided herein are methods and compositions related to expressing the disclosed viruses. For example, isolated polynucleotides that include a nucleic acid sequence encoding the genome or antigenome of the described viruses are disclosed. Such polynucleotides can be in the form of a vector, a linear segment of DNA or RNA, and can be in a positive or negative-sense orientation. The polynucleotides disclosed herein can be used to produce the viruses described via cellular expression through either viral or plasmid-driven expression systems that are known in the art. In one embodiment, plasmids encoding a viral genome or antigenome may be expressed in a cell along with other plasmids that express viral accessory proteins necessary for production of recombinant RSV.

Methods for producing an immune response to a protein in an animal are also described herein. Typically, such methods will be used to produce an immune response in mammals, including, but not limited to, mice, cotton rats, non-human primates, or humans. In some aspects, the disclosed recombinant, attenuated viruses can be administered to an individual in need of protection from infection by a virus, such as RSV, PIV, or MPV. In this regard, the viruses disclosed herein can be used as a vaccine. In another embodiment, the viruses provided herein could also be used to deliver nonviral proteins (e.g., a cytokine) to a mammal.

Described herein are methods for enhancing the genetic stability of, and identifying the genetic basis of phenotypic reversion of, attenuated virus strains. The provided methods consist of obtaining or identifying an attenuated, or mutant, virus strain; culturing the virus in the presence of a selection condition that is less restrictive to a wild-type strain of the virus, relative to an attenuated, or mutated, strain; identifying mutated strains of the attenuated virus that exhibit reduced attenuation under the restrictive conditions than would an non-mutated attenuated virus; and assessing the genome of the mutated strain of the attenuated virus to identify the genetic basis for the reduced attenuation exhibited by the strain. Upon identifying the genetic alteration giving rise to reduced attenuation of the virus, mutations can be made in the genetic sequence of the attenuated virus strain to prevent the mutation conferring reduced attenuation from arising. The provided methods are applicable to any attenuated virus capable of evolving to become less attenuated due to genetic mutation when cultured under selective conditions. For exemplary purposes, the method is described in the context of RSV herein; however, those skilled in the art will readily understand that it may be applied generally.

BRIEF DESCRIPTION OF THE DRAWINGS

FIGS. 1A-1F. Growth of mutant RSVs in vitro at increasing restrictive temperatures in a "temperature stress test" designed to assess phenotypic and genetic stability, based on a general method published in earlier work (McAuliffe, et al., J. Virol. 78:2029-36 (2004). (FIG. 1A) 10 independent aliquots of the virus 1321N(AAT) RSV were serially passed at increasingly restrictive temperature as follows: two passages at 35° C.; two at 36° C.; two at 37° C., for a total of 6 passages (solid lines)). For each passage, 1 ml (out of a total of 5 ml) of the supernatant was used to inoculate the next passage. In parallel, two independent replicas were passaged for 6 passages at 32° C. (non-restrictive temperature), serving as controls (dotted lines). For each passage, aliquots were frozen for titration and sequence analysis. Virus titers of the mutants at the different passage levels are shown, with the passage temperatures indicated. Virus titer was determined by plaque assay at the permissive temperature (32° C.). Passage number 0 represents the input virus. FIGS. 1B, 1C, 1D, 1E, and 1F show results with the following RSV mutants: 1321E(GAA), 1321K(AAA), 1321G(GGT), 1321G(GGA), and 1321P(CCT). Nomenclature: Note that the viruses are named according to the amino acid assignment and codon at L protein amino acid position 1321. Specifically, the number 1321 specifies the amino acid position; the letter to the right of the number (e.g., G in 1321G) specifies the amino acid assignment using the single letter code, and its placement to the right of the number indicates it is a non-wild-type assignment, and the codon for this mutant assignment is indicated to the right, e.g., (GAA) in 1321G(GAA). All of these viruses were based on the wild-type (wt) recombinant D46/6120 backbone that is described in the description of FIG. 2.

FIG. 2. Selected mutations involving L protein amino acid sequence positions 1313 and 1321 of RSV strain A2, numbered according to the complete sequence of the wild-type ("wt") human RSV strain A2 that is represented by Genbank accession number M74568. All of these viruses were constructed using the recombinant wt D46/6120 backbone, which differs from the full length recombinant wt parent by the deletion of 112 nucleotides from the downstream non-translated region of the SH gene, and also contains the introduction of five translationally silent nucleotide changes into the downstream end of the SH open reading frame (Bukreyev, et al. J. Virol., 75:12128-12140, 2001). The nucleotide sequence and amino acid coding assignments for the region of the L gene encompassing nucleotides 12422-12466 are shown at the top. Nucleotide numbering is shown at the top, amino acid sequence position numbers of the L protein are indicated at the bottom. The wt sequence is shown at the top; assignments in subsequent mutants that are identical to wt are shown as dots Amino acid substitutions relative to wt are highlighted in grey. This Figure illustrates a series of virus pairs in which the first of each pair has the wt assignment of S at position 1313, and the second has a putative compensatory mutation C at position 1313, and both viruses of the pair have the same assignment at position 1321 that changes from pair to pair.

Figures 4A, 4B:
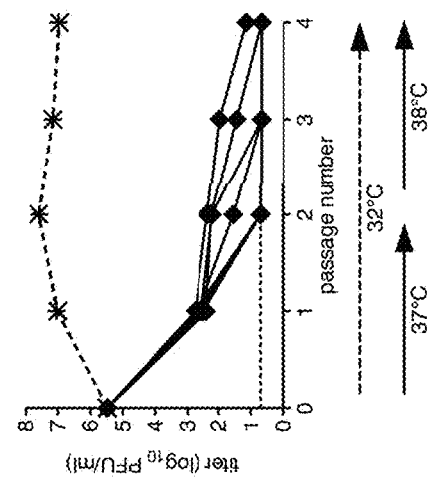

Nomenclature: The viruses in this Figure are named (listed at the left) according to the amino acid assignment at position 1321 followed by the assignment at 1313. Wild-type assignments have the single letter amino acid code to the left of the number. Mutant assignments have the single letter amino acid code to the right of the number with the codon specified in parentheses. If more than one mutant codon is acceptable, a codon might not be specified. The general nomenclature noted here and in FIG. 1 is used throughout (except where noted) and of necessity is descriptive rather than rigidly limiting.

The following SEQ ID NOs. are associated with this figure: SEQ ID NO: 1 (nucleotides 12422-12466 of wt human RSV A2 strain (GenBank accession number M74568), SEQ ID NO: 2 (nucleotides 12422-12466 of RSV mutant Y1321/1313C), SEQ ID NO: 3 (nucleotides 12422-12466 of RSV mutant 1321E(GAA)/S1313), SEQ ID NO: 4 (nucleotides 12422-12466 of RSV mutant 1321E(GAA)/1313C), SEQ ID NO: 5 (nucleotides 12422-12466 of RSV mutant 1321K(AAA)/S1313), SEQ ID NO: 6 (nucleotides 12422-12466 of RSV mutant 1321K(AAA)/1313C), SEQ ID NO: 7 (nucleotides 12422-12466 of RSV mutant 1321G (GGA)/S1313), SEQ ID NO: 8 (nucleotides 12422-12466 of RSV mutant 1321G(GGA)/1313C), SEQ ID NO: 9 (nucleotides 12422-12466 of RSV mutant 1321G(GGT)/S1313), SEQ ID NO: 10 (nucleotides 12422-12466 of RSV mutant 1321G(GGT)/1313C), SEQ ID NO: 11 (amino acids 1309-1323 of the L protein of wt human RSV A2 strain), SEQ ID NO: 12 (amino acids 1309-1323 of the L protein of RSV mutant Y1321/1313C), SEQ ID NO: 13 (amino acids 1309-1323 of the L protein of RSV mutant 1321E(GAA)/S1313), SEQ ID NO: 14 (amino acids 1309-1323 of the L protein of RSV mutant 1321E(GAA)/1313C), SEQ ID NO: 15 (amino acids 1309-1323 of the L protein of RSV mutant 1321K (AAA)/S1313), SEQ ID NO: 16 (amino acids 1309-1323 of the L protein of RSV mutant 1321K(AAA)/1313C), SEQ ID NO: 17 (amino acids 1309-1323 of the L protein of RSV mutant 1321G(GGA)/S1313), SEQ ID NO: 18 (amino acids 1309-1323 of the L protein of RSV mutant 1321G(GGA)/ 1313C), SEQ ID NO: 17 (amino acids 1309-1323 of the L protein of RSV mutant 1321G(GGT)/S1313), SEQ ID NO: 18 (amino acids 1309-1323 of the L protein of RSV mutant 1321G(GGT)/1313C). It should be noted that SEQ ID NOs. 17 is listed twice, because the same amino acid sequence is encoded by the polynucleotides for SEQ ID NOs. 7 and 9.

SEQ ID NOs. 18 is listed twice, because the same amino acid sequence is encoded by the polynucleotides for SEQ ID NOs. 8 and 10.

FIGS. 3A and 3B. Stabilization of L protein amino acid sequence positions 1321 and 1313. FIG. 3A. Sequences of the relevant portions of the L gene and protein of wt RSV are shown at the top (nucleotide residues 12428-12463 of SEQ ID NO: 1 and amino acid residues 1311-1322 of SEQ ID NO: 11), followed by those of a mutant RSV with an alternative codon and amino acid assignment at 1321, namely K(AAA), and an alternative codon for the wt assignment at 1313, namely S1313(TCA), designed to confer increased stability (nucleotide residues 12428-12463 of SEQ ID NO: 19 and amino acid residues 1311-1322 of SEQ ID NO: 15). These viruses are based on wt recombinant RSV 6120. FIG. 3B. An abbreviated temperature stress test was performed for virus 1321K(AAA)/S1313(TCA). Ten replicas were passaged twice at 37° C., and twice at 38° C., for a total of four passages (solid lines). Two replicas were passaged as "non-stressed" controls at the permissive temperature of 32° C. for four passages (dotted lines). Virus titers of the mutants at different passage levels are shown, as detailed above. The substantial decrease in titer for the independent parallel cultures of the mutant "stabilized" virus at the restrictive temperatures (solid lines) compared to the permissive temperature of 32° C. (dotted lines) indicates that there was a substantial restriction of growth in all cultures at the restrictive temperature, consistent with genetic and phenotypic stability of the attenuated phenotype.

Nomenclature: note that, when the amino acid assignment remains wt, but the codon is changed, the amino acid is indicated to the left and the codon to the right, e.g., S1313 (TCA). The general nomenclature noted here and in FIGS. 1 and 2 is used throughout (except where noted) and of necessity is descriptive rather than rigidly limiting.

FIGS. 4A and 4B. Deletion of L gene codon 1313. FIG. 4A. Sequences of the relevant portions of the L gene and protein of wt RSV are shown at the top (SEQ ID NO: 1 and SEQ ID NO: 11), followed by those of a mutant RSV with deletion of codon 1313 (nucleotide residues of SEQ ID NO: 20 and amino acid residues of SEQ ID NO: 21). These viruses are based on recombinant wt RSV 6120 described in the description to FIG. 2. FIG. 4B. An abbreviated temperature stress test was performed for virus Δ1313. Ten replicate cultures were passaged twice at 37° C., and twice at 38° C., for a total of four passages (solid lines). Two replicate cultures were passaged at the permissive temperature of 32° C. for four passages (dotted lines). Virus titers of the mutants at different passage levels are shown, as detailed above. The substantial decrease in titer for the independent parallel cultures of the Δ1313 mutant at restrictive temperatures (solid lines) compared to the permissive temperature of 32° C. (dotted lines) indicates that there was a substantial restriction of growth in all cultures at the restrictive temperature, consistent with the Δ1313 virus having an attenuated phenotype at restrictive temperatures, and this attenuated phenotype having genetic and phenotypic stability.

Nomenclature: The virus with deletion of codon 1313 is designated Δ1313 with no reference to position 1321 (which remains wt). The general nomenclature noted here and in FIGS. 1, 2, and 3 is used throughout (except where noted) and of necessity is descriptive rather than rigidly limiting.

Figure 5:
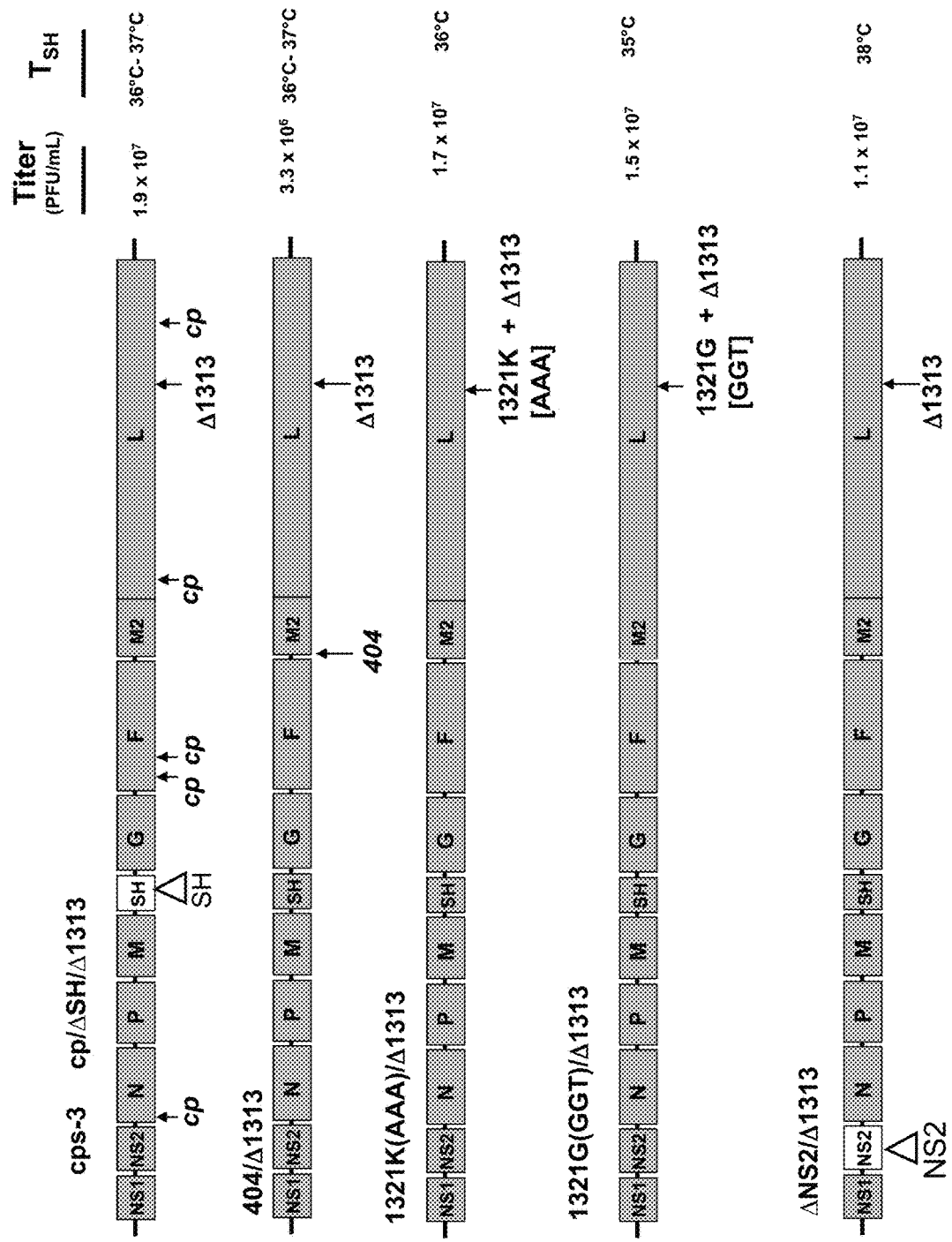

FIG. 5. A depiction of the gene maps of five examples of attenuated recombinant RSVs bearing the Δ1313 mutation in combination with various other mutations. Note that some of the mutations involved are derived from previously described attenuated mutants such as the rA2cp248/404/ 1030ΔSH virus that was previously constructed and one version of which has been evaluated in clinical studies (Karron et al, JID 191:1093-1104, 2005)(see the description of FIG. 10 for an explanation). Note that these mutations use a separate nomenclature: the numbers 404 and 1030 refer to biological clones from the original mutagenesis experiments and not to sequence positions. The mutation set noted as "cp" comprises the following 5 amino acid substitutions: V267I in the N protein, E218A and T523I in the F protein, and C319Y and H1690Y in the L protein (Whitehead et al J Virol 72:4467-4471, 1998). The "404" mutation involves a nucleotide substitution in an RNA signal and was as described (Whitehead et al Virology 247:232-239, 1998; Whitehead et al, J Virol 73:871-877, 1999). Specifically, this involves a T to C substitution at the ninth nucleotide position of the gene-start signal of the M2 gene, corresponding to nucleotide 7606 in RSV strain A2 (relative to a positive sense genome). ΔSH refers to deletion of the SH gene (Bukreyev et al J Virol 71:8973, 1997; Karron et al JID 191:1093-1104, 2005; Whitehead et al J Virol 73:3438-3442, 1999), and in this case involved nucleotides 4210-4628, and joined the last nucleotide of the M gene-end signal to the first nucleotide of the SH-G intergenic region. ΔNS2 refers to deletion of the NS2 gene, involving deletion of nucleotides 577-1098, joining the gene-end signal of the NS1 gene to the NS2-N intergenic region. The cps-3 virus was based on full-length recombinant wt RSV (nucleotide length 15,223 prior to the SH and 1313 deletions), and the other viruses were based on recombinant wt 6120. Typical viral titers and shut off temperatures also are shown: the shut off temperature ($T_{SH}$) is defined as the lowest restrictive temperature at which the reduction compared to 32° C. is 100-fold or greater than that observed for wt RSV at the two temperatures.

Figure 6:
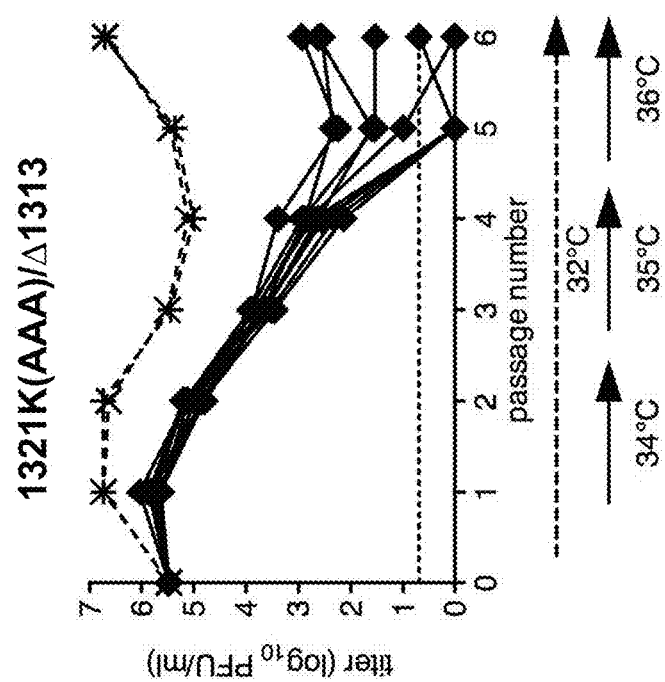

FIG. 6. Temperature stress test of a virus bearing an alternative amino acid assignment at L protein codon 1321, namely K(AAA), plus the deletion of codon 1313. Ten replicate cultures were passaged twice at 34° C., twice at 35° C., and twice at 36° C., for a total of six passages (solid lines). Note that 35-36° C. appeared to be restrictive for this virus (its $T_{SH}$ is 36° C., FIG. 5 and Table 9). Two replicate cultures were passaged at the permissive temperature of 32° C. for six passages (dotted lines). Virus titers of the mutants at different passage levels are shown, as detailed above. The substantial decrease in titer for the independent parallel cultures of the mutant virus at the restrictive temperatures (solid lines) compared to the permissive temperature of 32° C. (dotted lines) indicates that there was a substantial restriction of growth in all cultures at 35-36° C., consistent with genetic and phenotypic stability of the attenuated virus.

Figure 7:
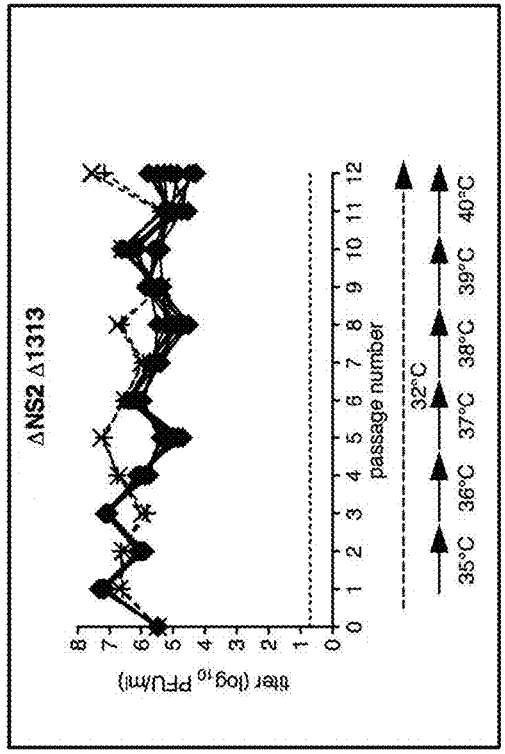

FIG. 7. Temperature stress test of the ΔNS2/Δ1313 virus, which bears the deletion of the NS2 gene and deletion of codon 1313 in the L gene (see FIG. 5 for a gene map). A. Ten replicate cultures were passaged twice at each of the following temperatures: 35° C., 36° C., 37° C., 38° C., 39° C., and 40° C., for a total of twelve passages (solid lines). Two replicate cultures were passaged at the permissive temperature of 32° C. for twelve passages (dotted lines). Virus titers of the mutants at different passage levels are shown, as detailed above. B. Sequence analysis of viral populations following the tenth passage showed that all of the populations from the restrictive passages contained an isoleucine-to-threonine substitution at L amino acid sequence position 1314, as shown. The sequences shown, from top to bottom, are: amino acids 1311-1315 of SEQ ID NO: 11 and nucleotides 12428-12442 of SEQ ID NO: 1, both of wt RSV; amino acids 1311-1315 of SEQ ID NO: 22 and nucleotides 12428-

12442 of SEQ ID NO: 23, both of ΔNS2/Δ1313 passaged at permissive temperature (i.e., not containing the 1314T mutation); amino acids 1311-1315 of SEQ ID NO: 24 and nucleotides 12428-12442 of SEQ ID NO: 25, both of ΔNS2/Δ1313/1314T, the mutant that emerged during passage of ΔNS2/Δ1313 at elevated temperatures.

FIG. 8. Nucleotide and amino acid sequences of wt RSV and mutant RSVs illustrating substitutions and deletions that were introduced at amino acid sequence positions 1313, 1314, 1316, and 1320 of the L protein. The provided sequences show either the wt or corresponding mutated sequences for nucleotides 12428-12457 or amino acids 1311-1320 of the RSV L protein. Note that this set of mutations and deletions was introduced in parallel into two different backbones: a backbone that otherwise was wt 6120 (shown in this Figure) and a second 6120-based backbone that contained the deletion of the NS2 gene.

Figure 9A:
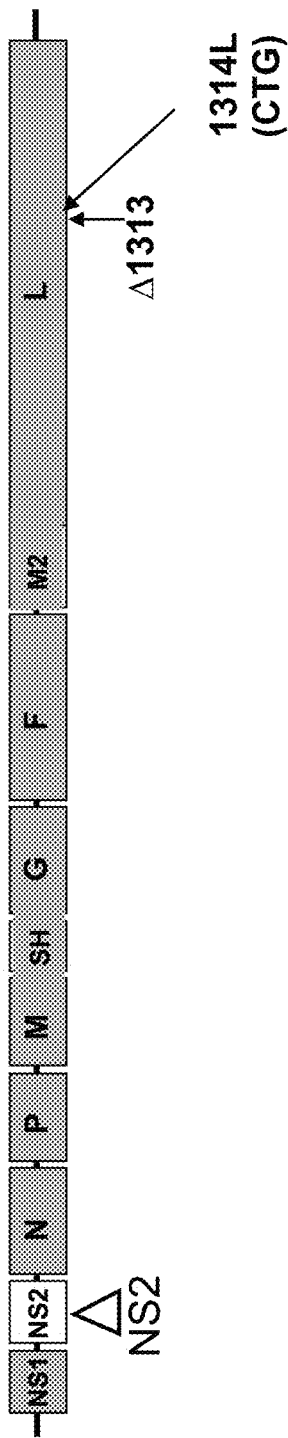
Figure 9B:
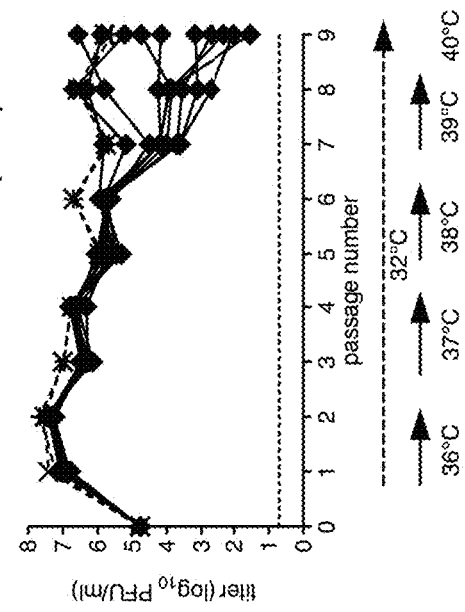

FIGS. 9A and 9B. Gene map and temperature stress test of the ΔNS2/Δ1313/1314L(CTG) virus, which bears the deletion of the NS2 gene, the deletion of codon 1313 in the L gene, and the 1314L(CTG) substitution in the L gene. FIG. 9A. A depiction of the gene map of the ΔNS2/Δ1313/1314L (CTG) virus. FIG. 9B. Temperature stress test. Ten replicate cultures were passaged twice at each of the following temperatures: 36° C., 37° C., 38° C., and 39° C., and once at 40° C. for a total of nine passages (solid lines). Two replicate cultures were passaged at the permissive temperature of 32° C. for the same number of passages (dotted lines). Virus titers of the mutants at different passage levels are shown, as detailed above.

Figure 10:
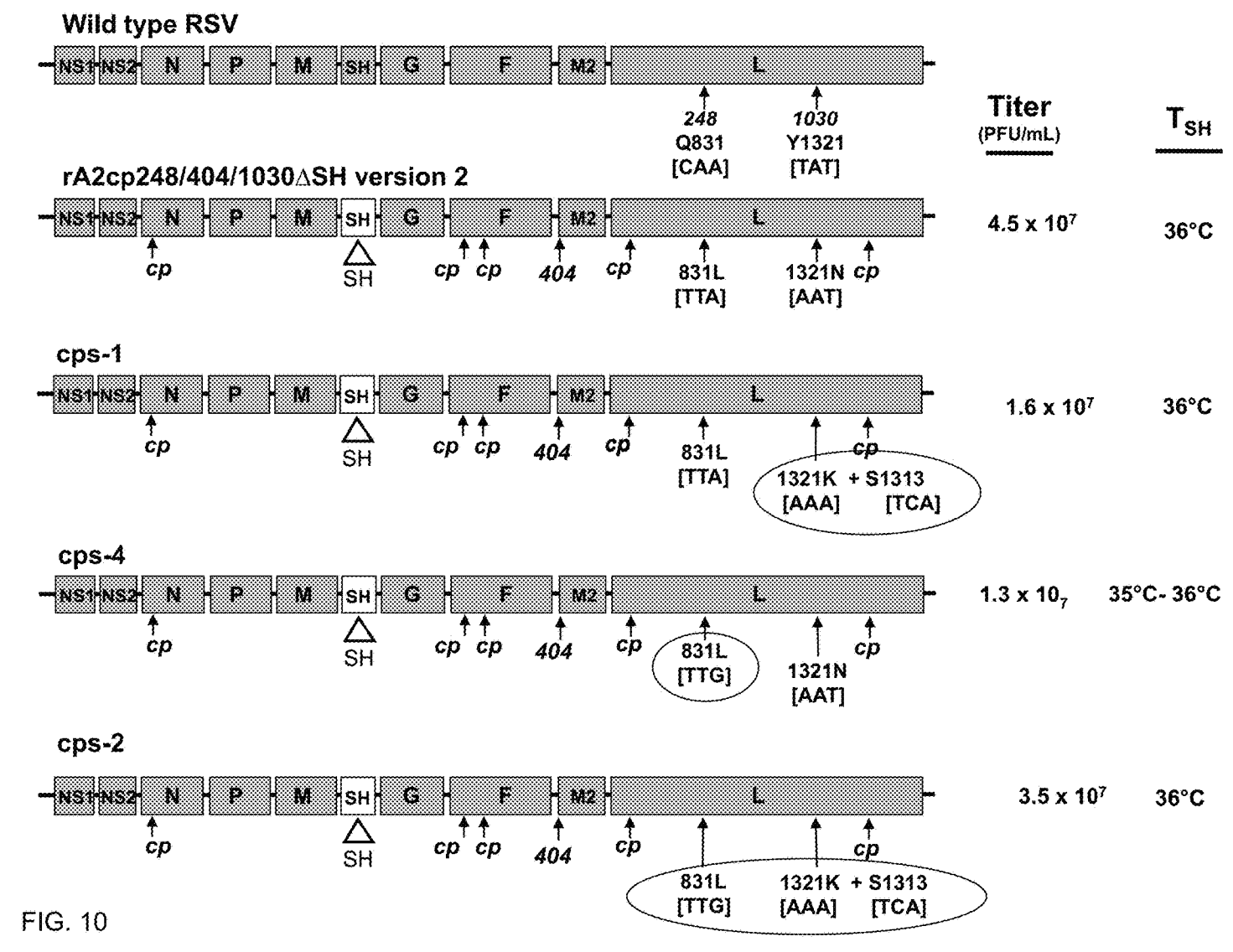

FIG. 10. A depiction of the gene maps of wt RSV (top line) and several attenuated derivatives. The virus rA2cp248/404/1030ΔSH is a vaccine candidate that was designed by reverse genetics and recovered from cDNA. One version of this virus, referred to herein as "cp248/404/1030ΔSH version 2," is being evaluated in clinical studies (ClinicalTrials.gov Identifier NCT00767416). The other vaccine candidate viruses that are shown have changes in specific codons (circled) designed for increased genetic and phenotypic stability. Note that these viruses use a separate nomenclature for mutations: the numbers 248, 404, and 1030 refer to biological clones from the original mutagenesis experiments and not to sequence positions. The mutations noted as "cp" (cold passage) comprise the following 5 amino acid substitutions: V267I in N, E218A and T523I in F, and C319Y and H1690Y in L (Whitehead et al., J. Virol. 72:4467-4471, 1998). The "248" and "1030" loci are indicated. The "404" mutation involves a T to C substitution at nucleotide 7606, which involves the gene-start signal for the M2 gene (Whitehead et al., Virology 247:232-239, 1998; Whitehead et al., J. Virol., 73:871-877, 1999). ΔSH refers to deletion of the SH gene (Bukreyev et al., J. Virol., 71:8973, 1997; Karron et al., JID 191:1093-1104, 2005; Whitehead et al., J. Virol. 73:3438-3442, 1999), which in this case involved nucleotides 4210-4628, and joined the last nucleotide of the M gene-end signal to the first nucleotide of the SH-G intergenic region. Each of these viruses is based on full-length recombinant wt RSV (nucleotide length 15,223 prior to any deletions). Typical viral titers and shut off temperatures also are shown: the shut off temperature ($T_{SH}$) is defined as the lowest restrictive temperature at which the reduction compared to 32° C. is 100-fold or greater than that observed for wt RSV at the two temperatures.

Note that another version of the rA2cp248/404/1030ΔSH cDNA had previously been constructed, and virus was recovered (Karron et al., JID 191:1093-1104, 2005). This version of the cDNA and its encoded virus are referred to herein as "cp248/404/1030ΔSH version 1." This version was previously evaluated in RSV-naïve young infants (Karron et al., JID 191:1093-1104, 2005), and was well-tolerated, moderately immunogenic, and protective against a second vaccine dose. Both versions of rA2cp248/404/1030ΔSH contain the cp, 248, 404, 1030, and ΔSH mutations, and no differences have been identified between the two versions with regard to virus replication, ts and attenuation phenotypes, or other biological properties. The two versions differ by multiple point mutations throughout the genome that mostly are silent at the amino acid level and are considered inconsequential. These include differences due to naturally occurring variability in wt virus and in some cases due to the presence or absence of added restriction sites or sequence tags. As another difference, the "248" mutation (Q831L) is specified by the codon TTA in cp248/404/10030ΔSH version 2 and CTG in cp248/404/1030ΔSH version 1. In general, the two versions of rA2cp248/404/1030ΔSH appear to have similar properties of growth, temperature sensitivity, and attenuation. The diagram and data shown here represent cp248/404/10030ΔSH version 2. The derivatives cps-1, cps-4, cps-2, and cps-3 were derived from cp248/404/10030ΔSH version 2.

FIG. 11. Schematic representation of various domains in the RSV L protein and various deletion mutations involving amino acid residues 1744-1764. The domains have been described elsewhere (Poch et al EMBO J 8:3867-74, 1989; J Gen Virol 71:1153-62, 1990). Each mutation is named by the amino acid residue(s) in the L protein that was deleted. Viruses that involve deletion of 2-4 codons are named using the L protein amino acid position of the first residue that is deleted, followed by the Δ symbol, followed by the specific contiguous residues that were deleted (e.g., 1754ΔSSAM involves deletion of residues 1754-1757, which have the identities SSAM). For deletions larger than 4 residues, the number of contiguous deleted residues is indicated followed by "aa" (e.g., 1752Δ13aa involves a deletion of 13 amino acid (aa) residues beginning with 1752 and ending 1764). SEQ ID NOs are provided for each listed sequence (SEQ ID NO: 36 represents the wild-type RSV A2 strain sequence for amino acids 1744-1764 of the L protein).

SEQUENCE LISTING

The Sequence Listing is submitted as an ASCII text file in the form of the file named "Sequence.txt" (~36 kb), which was created on Mar. 10, 2017, which is incorporated by reference herein.

DETAILED DESCRIPTION OF ILLUSTRATIVE EMBODIMENTS

Attenuating and Stabilizing Mutations of RSV

Provided herein are recombinant RSVs suitable for vaccine use in humans. Attenuated RSVs described herein are produced by introducing and/or combining specific attenuating mutations into incompletely attenuated strains of RSV, such as a temperature sensitive (ts) or cold-passaged (cp) RSV, or into wild-type virus, e.g. RSV strain A2. As used herein, the term "temperature sensitive" refers to the property of reduced replication compared to wild-type virus at temperatures at which the wild-type virus normally replicates. For example, wild-type RSV replicates efficiently within the range of 32° C. to 40° C., whereas a temperature-sensitive mutant would be restricted in replication at the higher temperatures within this range, but could be propagated efficiently at 32° C., which is called the "permissive temperature." These viruses can be made using recombinant methods useful in identifying attenuated RSV strains. Once identified, the attenuating mutations can be introduced into biologically-derived strains, used to further attenuate or stabilize existing attenuated RSV strains, or attenuated RSV strains may be designed de novo.

The term "wild-type" as used herein refers to a viral phenotype that is consistent with efficient replication in a suitable permissive human host, and that may induce disease in a susceptible human host (for example, an RSV-naïve infant). The prototype A2 strain, represented by Genbank accession number M74568 but not strictly limited to that sequence, is considered to be an example of a wild-type strain. Derivative viruses that contain mutations that are presumed to not significantly reduce replication or disease in vivo also have the "wild-type" phenotype. In contrast, viral derivatives that exhibit reductions in replication of approximately 10-fold, 100-fold, or more in vivo may be considered to be "restricted". Generally, restricted replication in vivo in a susceptible host is associated with reduced disease, or "attenuation." Thus, infection of a susceptible host with an "attenuated" virus results in reduced disease in that host, as compared to a wild-type strain.

The term "stable" in the context of virus stability refers to the decreased likelihood that a genetic change will occur in the genome of a virus that results in a change to the phenotype of the virus. As described herein, a virus with increased stability can be produced by altering one or more polynucleotide residues of the viral genome, which may or may not result in an amino acid change for an encoded protein, to reduce the likelihood of the virus undergoing a genetic change that may alter the phenotype of the virus.

Recombinant infectious respiratory syncytial viruses having a large polymerase protein, phosphoprotein, nucleocapsid protein and a M2-1 protein and a genome or antigenome having a mutation in the codon that encodes the tyrosine at position 1321, or a corresponding position, of the L protein that causes an amino acid other than tyrosine or asparagine to be encoded at position 1321, or a corresponding position, of the L protein are described herein. These viruses may optionally include a nonstructural protein 1, a nonstructural protein 2, a glycoprotein, a fusion protein, matrix protein, M2-2 protein, and a small hydrophobic protein. Accordingly, the corresponding virus genome or antigenome may optionally include these proteins either individually or in combination with one another. In some embodiments the viruses disclosed herein are attenuated. Given that a variety of RSV strains exist (e.g., RSV A2, RSV B, RSV Long), those skilled in the art will appreciate that certain strains of RSV may have nucleotide or amino acid insertions or deletions that alter the position of a given residue, relative to the numbering used this disclosure, which is based on the sequence of the biologically derived wild-type RSV A2 strain (GenBank accession number M74568). For example, if the L protein of a heterologous RSV strain had, in comparison with strain A2, two additional amino acids in the upstream end of the L protein, this would cause the amino acid numbering of downstream residues relative to strain A2 to increase by an increment of two. However, because these strains share a large degree of sequence identity, those skilled in the art would be able to determine the location of corresponding sequences by simply aligning the nucleotide or amino acid sequence of the A2 reference strain with that of the strain in question. Therefore, it should be understood that the amino acid and nucleotide positions described herein, though specifically enumerated in the context of this disclosure, can correspond to other positions when a sequence shift has occurred or due to sequence variation between virus strains. In the comparison of a protein, or protein segment, or gene, or genome, or genome segment between two or more related viruses, a "corresponding" amino acid or nucleotide residue is one that is thought to be exactly or approximately equivalent in function in the different species.

The recombinant infectious respiratory syncytial virus disclosed herein can have a variety of mutations at position 1321, or a position corresponding thereto, such that the codon encoding this residue is modified to encode a different amino acid. In some embodiments, the tyrosine residue found at position 1321 will be substituted with a different amino acid, such as glutamic acid, lysine, glycine, proline, threonine, cysteine, glutamine, valine, or alanine. In one embodiment, the recombinant infectious respiratory syncytial viruses described can be mutated at the codon associated with position 1321 of the L protein to have a codon sequence of GAA to encode glutamic acid. In one embodiment, the recombinant infectious respiratory syncytial viruses described can be mutated at the codon associated with position 1321 of the L protein to have a codon sequence of GAG to encode glutamic acid. In one embodiment, the recombinant infectious respiratory syncytial viruses described can be mutated at the codon associated with position 1321 of the L protein to have a codon sequence of AAA to encode lysine. In one embodiment, the recombinant infectious respiratory syncytial viruses described can be mutated at the codon associated with position 1321 of the L protein to have a codon sequence of GGA to encode glycine. In one embodiment, the recombinant infectious respiratory syncytial viruses described can be mutated at the codon associated with position 1321 of the L protein to have a codon sequence of GGC to encode glycine. In one embodiment, the recombinant infectious respiratory syncytial viruses described can be mutated at the codon associated with position 1321 of the L protein to have a codon sequence of GGT to encode glycine. In one embodiment, the recombinant infectious respiratory syncytial viruses described can be mutated at the codon associated with position 1321 of the L protein to have a codon sequence of CCT to encode proline. The specific codon combinations recited herein are provided to exemplify certain aspects of the invention; however, those skilled in the art will understand that, due to the degenerate nature of the genetic code, a number of codons may be used to encode the amino acids described herein. In some embodiments, the codons described herein may be mutated by making one nucleotide change in a codon. In other embodiments, the codons described herein may be mutated by making two nucleotide changes in a codon. In still another embodiment, the codons described herein may be mutated by making three nucleotide changes in a codon. Furthermore, based on this disclosure, those skilled in the art will readily understand that a mutation at position 1321 may be combined with any number of previously described RSV mutant strains in order to enhance the attenuation or stability of the virus. In addition, a mutation at position 1321 may be combined with any number of previously described individual RSV mutations or deletions to produce a new, attenuated virus. For example a mutation at position 1321 of the L protein may also be combined with other RSV mutations such as deletion of the NS2 gene (ΔNS2); cp mutations such as V267I in the N protein, E218A and T523I in the F protein, and C319Y and H1690Y in the L protein; mutation of residue 831 in the L protein, such as Q831L; and deletion of the SH gene (ΔSH).

Also provided herein are RSVs that have a mutation in the codon encoding serine at position 1313, or a corresponding position, of the L protein, such that a different serine codon is present. For example, rather than serine 1313 being encoded by the codon AGC, a different codon, such as TCA, could be used to encode serine. A mutation of this sort could serve to stabilize the codon from spontaneous mutation. Because RSV polymerase is error prone to some degree, undesirable mutations can arise. In some instances it is desirable to decrease the likelihood of this possibility by modifying a codon such that it is less amenable to certain mutations. As will be described herein, the serine codon TCA is less likely than AGC to be mutated to the codon TGC, which encodes cysteine, because only one nucleotide alteration (A to T) needs to occur when the AGC codon is present. Thus, the TCA codon decreases the likelihood of this mutation arising. In some embodiments, the codons described herein may be mutated by making one nucleotide change in a codon, such as the codon encoding serine at position 1313 of the L protein. In other embodiments, the codons described herein may be mutated by making two nucleotide changes in a codon, such as the codon encoding serine at position 1313 of the L protein. In still another embodiment, the codons described herein may be mutated by making three nucleotide changes in a codon, such as the codon encoding serine at position 1313 of the L protein. These strategies can apply more broadly to the mutations described herein and should not be considered to be limited to the embodiments described in this paragraph. Furthermore, based on this disclosure, those skilled in the art will readily understand that a mutation at position 1313 may be combined with any number of previously described RSV mutant strains in order to enhance the attenuation or stability of the virus. In addition, a mutation at position 1313 may be combined with any number of previously described individual RSV mutations or deletions to produce a new, attenuated virus.

In some aspects described herein, the amino acid residue at position 1313 of the RSV L protein, or a corresponding position, may be deleted (Δ1313) by eliminating the three nucleotides making up the codon that encodes the amino acid. In some embodiments, recombinant RSVs having a deletion at position 1313 will exhibit desirable characteristics such as increased attenuation or a decreased likelihood of reverting to a less attenuated state. Recombinant RSVs having the Δ1313 deletion exibited a temperature-sensitive attenuation phenotype that is genetically stable. In another embodiment, presence of the Δ1313 deletion in a recombinant RSV does not reduce virus replication at a permissive temperature, which is important for vaccine manufacture. As described herein, these attributes associated with the Δ1313 mutation were unexpected because deletion mutants involving one or a few codons typically are nonviable or reduce replication so as to be unacceptable for vaccine manufacture. This particular Δ1313 deletion mutation was particularly unexpected since, as described herein, a previous mutation involving this position had the opposite effect of reducing temperature sensitivy and attenuation in an attenuated background. This mutation can be used individually to create a recombinant RSV. In other embodiments, the Δ1313 mutation may be used in combination with other mutations or deletions to create a recombinant RSV.

As described herein, RSV may have an L protein mutated at positions 1313 and 1321. In some embodiments such viruses may be RSV 1321K/S1313(TCA), RSV 1321E/S1313(TCA), RSV 1321P/S1313(TCA), or RSV 1321G/S1313(TCA). In some embodiments the lysine residue in RSV 1321K/S1313(TCA) is encoded by the nucleotides AAA to produce RSV 1321K(AAA)/S1313(TCA). In some embodiments the glycine residue in RSV 1321G/S1313 (TCA) is encoded by the nucleotides GGA to produce RSV 1321G(GGA)/S1313(TCA). In some embodiments, residue 1313 will be mutated to be encoded by a codon having the sequence TCA, which may be combined with any of the mutations at position 1321 described herein. In other embodiments, residue 1313 is mutated to be encoded by a sequence other than TCA. The mutations at positions 1313 and 1321 of the L protein may also be combined with other RSV mutations such as deletion of the NS2 gene (ΔNS2); cp mutations such as V267I in the N protein, E218A and T523I in the F protein, and C319Y and H1690Y in the L protein; mutation of residue 831 in the L protein, such as Q831L; and deletion of the SH gene (ΔSH). In one embodiment these mutations may be combined to produce RSV ΔNS2/1321K (AAA)/S1313(TCA). In another embodiment these mutations may be combined to produce RSV ΔNS2/1321K (AAA)/S1313(TCA)/cp/ΔSH. In one embodiment these mutations may be combined to produce RSV 1321K(AAA)/Δ1313. In another embodiment these mutations may be combined to produce RSV 1321K(AAA)/Δ1313/cp/ΔSH. In another embodiment these mutations may be combined to produce RSV 1321K(AAA)/S1313(TCA)/831L(TTG).

Also described are recombinant infectious RSVs with an L protein, a P protein, an N protein, an M2-1 protein, and a genome or antigenome having a deletion of the codon that encodes the serine at position 1313 (Δ 1313), or a corresponding position, of the L protein. In addition, the described RSV may have a NS1 protein, a NS2 protein, a M2-2 protein, a G protein, a F protein, M protein and a SH protein. In some embodiments described herein, RSV may be mutated at residue 1321 of the L protein and also have a deletion of residue 1313 of the L protein. In one embodiment, such a virus is RSV Y1321/Δ1313. Another such virus could be RSV 1321K/Δ1313, for example, RSV 1321K (AAA)/Δ1313. In another embodiment, residue 1313 could be deleted to form RSV 1321G/Δ1313, for example, RSV 1321G(GGT)/Δ1313. In another embodiment, residue 1313 could be deleted to form RSV 1321P/Δ1313. And in still another embodiment, residue 1313 could be deleted to form RSV 1321E/Δ1313. The mutation of the RSV L protein at position 1313 can also be combined with other RSV mutations to yield a recombinant RSV that has increased attenuation or a decreased likelihood of reverting to a less attenuated state. For example, the 1313 mutation may also be combined with other RSV mutations such as deletion of the NS2 gene (ΔNS2); cp mutations such as V267I in the N protein, E218A and T523I in the F protein, and C319Y and H1690Y in the L protein; mutation of residue 831 in the L protein, such as Q831L; and deletion of the SH gene (ΔSH). One such embodiment is a cpRSV that has the gene encoding its SH protein deleted and also has residue 1313 of the L protein deleted (cp/ΔSH/Δ1313). In another embodiment the Δ1313 mutation is combined with only the previously-described "404" mutation in the gene-start signal of the M2 gene (Whitehead et al, J. Virol. 247:232-239, 1998) to form a mutant virus (404/Δ1313). Similar such combinations, such as RSV ΔNS2/Δ1313, are also described herein. Furthermore, based on this disclosure, those skilled in the art will readily understand that the Δ1313 mutation may be combined with any number of previously described RSV mutant strains in order to enhance the attenuation or stability of the virus.

Described herein are also recombinant RSVs having a L protein, a P protein, a N protein, a M2-1 protein, and a genome or antigenome having a mutation or a deletion of at least one codon encoding an amino acid among residues 1744-1764 of the L protein. In some embodiments the genome or antigenome of such RSVs optionally encode a NS1 protein, a NS2 protein, a M2-2 protein, a G protein, a F protein, M protein and a SH protein. In some embodiments, only one residue in the 1744-1764 span of the L protein will be mutated or deleted; however, in other embodiments several or all of these residues will be mutated or deleted. Some particular RSVs exemplified herein are RSV 1754ΔS, RSV 1756ΔA, RSV 1753ΔKS, RSV 1754ΔSS, RSV 1755ΔSA, RSV 1753ΔKSSA, RSV 1754ΔSSAM, RSV 1752Δ6aa, RSV 1749Δ9aa, RSV 1744Δ13aa, RSV 1744Δ14aa, and RSV 1744Δ21aa. Furthermore, based on this disclosure, those skilled in the art will readily understand that a mutation among residues 1744-1764 of the L protein may be combined with any number of previously described RSV mutant strains in order to enhance the attenuation or stability of the virus. In addition, a mutation among residues 1744-1764 of the L protein may be combined with any number of previously described individual RSV mutations or deletions to produce a new, attenuated virus. For example, a mutation among residues 1744-1764 of the L protein may also be combined with other RSV mutations such as deletion of the NS2 gene (ΔNS2); cp mutations such as V267I in the N protein, E218A and T523I in the F protein, and C319Y and H1690Y in the L protein; mutation of residue 831 in the L protein, such as Q831L; and deletion of the SH gene (ΔSH).

Provided herein are recombinant RSVs having a L protein, a P protein, a N protein, a M2-1 protein, and a genome or antigenome with a mutation or a deletion of the codon encoding the isoleucine amino acid residue corresponding to position 1314 of the L protein. In some embodiments, mutation of amino acid residue 1314 of the RSV L protein increases the stability of additional mutations in recombinant RSVs, which include, but are not limited to, mutations at codons 1313 and 1321 of the L protein. Accordingly, described herein are rembinant RSVs that include a mutation and position 1313 and 1314. In some embodiments, the mutation at position 1313 is a deletion, while the mutation at position 1314 is an amino acid change. In some embodiments, the mutation at position 1313 is a deletion, while the mutation at position 1314 is an amino acid change from isoleucine to leucine. In some embodiments, the mutation at position 1313 is a deletion, while the mutation at position 1314 is an amino acid change from isoleucine to leucine in which leucine is encoded by the codon "CTG". In some embodiments the genome or antigenome of such RSVs optionally encodes an NS1 protein, NS2 protein, M2-2 protein, G protein, F protein, M protein and an SH protein. In some embodiments, the codon encoding amino acid residue 1314 of the RSV L protein will be modified to cause an amino acid other than isoleucine to be encoded at position 1314. For example, the codon encoding isoleucine may be mutated to encode leucine. In one such embodiment, the leucine residue substituted at position 1314 is encoded by the codon "CTG". In some embodiments, the codon encoding isoleucine at position 1314 of the RSV L protein is deleted, so that no amino acid is encoded at position 1314 and the position is occupied by the amino acid residue that would otherwise occur at position 1315. In some embodiments, an RSV having a deletion of amino acid 1314 of the wt L protein (Δ1314) may have a lower $T_{SH}$ than its parental RSV strain. In addition, a virus with this deletion may exhibit significant attenuation, relative to its parent strain. In addition, this virus may have a genetic resistance to phenotypic reversion, and, thus be considered a desirable vaccine candidate as is, or may be combined with other mutations to give rise to a new virus strain. In some embodiments, an RSV having a mutation of amino acid 1314 of the wt L protein (e.g., 1314L) may have a lower $T_{SH}$ than its parental RSV strain. In some embodiments, the 1314L mutation is encoded by a codon having the nucleotide sequence "CTG". In addition, a virus with this mutation may exhibit significant attenuation, relative to its parent strain. In addition, this virus may have, or confer, a genetic resistance to phenotypic reversion, and, thus be considered a desirable vaccine candidate as is, or may be combined with other mutations to give rise to a new virus strain. Furthermore, based on this disclosure, those skilled in the art will readily understand that a mutation at position 1314 of the RSV L protein may be combined with any number of previously described RSV mutant strains in order to enhance the attenuation or stability of the virus. In addition, a mutation at position 1314 of the RSV L protein may be combined with any number of previously described individual RSV mutations or deletions to produce a new, attenuated virus. For example, this mutation may be combined with an existing attenuated virus to form RSV ΔNS2/Δ1313/1314L(CTG), RSV Δ1313/1314L (CTG), or RSV ΔNS2/Δ1314.

Provided herein are recombinant RSVs having a L protein, a P protein, a N protein, a M2-1 protein, and a genome or antigenome with a mutation or a deletion of the codon encoding the isoleucine amino acid residue corresponding to position 1316 of the L protein. In some embodiments the genome or antigenome of such RSVs optionally encode a NS1 protein, a NS2 protein, a M2-2 protein, a G protein, a F protein, M protein and a SH protein. In some embodiments, the codon encoding isoleucine at position 1316 of the RSV L protein is deleted, so that no amino acid is encoded and the position is occupied by the amino acid residue that would otherwise occur at position 1317. In addition, a virus with this mutation may exhibit significant attenuation, relative to its parent strain and may have, or confer, genetic resistance to phenotypic reversion, and, thus be considered a desirable vaccine candidate as is, or may be combined with other mutations to give rise to a new virus strain. For example, a mutation at position 1316 of the L protein may also be combined with other RSV mutations such as deletion of the NS2 gene (ΔNS2); cp mutations such as V267I in the N protein, E218A and T523I in the F protein, and C319Y and H1690Y in the L protein; mutation of residue 831 in the L protein, such as Q831L; and deletion of the SH gene (ΔSH). In one embodiment this mutation may be combined with an existing attenuated virus to form RSV ΔNS2/Δ1316.

Another attenuating RSV mutation described herein occurs at amino acid residue 649 of the RSV L protein. Accordingly, provided in this disclosure are recombinant RSVs having a L protein, a P protein, a N protein, a M2-1 protein, and a genome or antigenome with a mutation or a deletion of the codon encoding glutamic acid at a position corresponding to position 649 of the L protein. In some embodiments the genome or antigenome of such RSVs optionally encode a NS1 protein, a NS2 protein, a M2-2 protein, a G protein, a F protein, M protein and a SH protein. In some embodiments, the codon encoding glutamic acid at position 649 of the RSV L protein is mutated to cause a different amino acid to be encoded at this position. In some embodiments, the codon is mutated to encode an amino acid with a charged side chain. In one embodiment, the codon is mutated to encode aspartic acid at position 649 of the RSV L protein. Based on this disclosure, those skilled in the art will readily understand that a mutation at position 649 of the L protein may be combined with any number of previously described RSV mutant strains in order to enhance the attenuation or stability of the virus, or may be combined with previously characterized individual RSV mutations or deletions to produce a new virus. For example, a mutation at position 649 of the L protein may also be combined with other RSV mutations such as deletion of the NS2 gene (ΔNS2); cp mutations such as V267I in the N protein, E218A and T523I in the F protein, and C319Y and H1690Y in the L protein; mutation of residue 831 in the L protein, such as Q831L; and deletion of the SH gene (ΔSH). For example, E649D may be combined with a mutation at position 1321 of the L protein, a mutation at position 1313 of the L protein, or may be used with mutations at both positions 1321 and 1313. In one embodiment, the mutation E649D may be combined with the mutations 1321K(AAA) and S1313(TCA) to give rise to RSV strain 1321K(AAA)/S1313(TCA)+E649D.

Another attenuating RSV mutation described herein occurs at amino acid residue 874 of the RSV L protein. Accordingly, provided in this disclosure are recombinant RSVs having an L protein, a P protein, an N protein, a M2-1 protein, and a genome or antigenome with a mutation or a deletion of the codon encoding glutamine at a position corresponding to position 874 of the L protein. In some embodiments the genome or antigenome of such RSVs optionally encode a NS1 protein, a NS2 protein, a M2-2 protein, a G protein, an F protein, M protein and a SH protein. In some embodiments, the codon encoding glutamine at position 874 of the RSV L protein is mutated to cause a different amino acid to be encoded at this position. In some embodiments, the codon is mutated to encode an amino acid with a charged side chain. In one embodiment, the codon is mutated to encode histidine at position 874 of the RSV L protein. Based on this disclosure, those skilled in the art will readily understand that a mutation at position 874 of the L protein may be combined with any number of previously described RSV mutant strains in order to enhance the attenuation or stability of the virus, or may be combined with previously characterized individual RSV mutations or deletions to produce a new virus. For example, a mutation at position 874 of the L protein may also be combined with other RSV mutations such as deletion of the NS2 gene (ΔNS2); cp mutations such as V267I in the N protein, E218A and T523I in the F protein, and C319Y and H1690Y in the L protein; mutation of residue 831 in the L protein, such as Q831L; and deletion of the SH gene (ΔSH). Furthermore, Q874H may be combined with a mutation at position 1321 of the L protein, a mutation at position 1313 of the L protein, or may be used with mutations at both positions 1321 and 1313. In one embodiment, the mutation Q874H may be combined with the mutations 1321K(AAA) and S1313(TCA) to give rise to RSV strain 1321K(AAA)/S1313(TCA)+Q874H.

With regard to sequence numbering of nucleotide and amino acid sequence positions for the described viruses, a convention was used whereby each nucleotide or amino acid residue in a given viral sequence retained the sequence position number that it has in the original 15,222-nucleotide biological wt strain A2 virus (Genbank accession number M74568), irrespective of any modifications. Thus, although a number of genomes contain deletions and/or insertions that cause changes in nucleotide length, and in some cases amino acid length, the numbering of all of the other residues (nucleotide or amino acid) in the genome and encoded proteins remains unchanged. It also is recognized that, even without the expedient of this convention, one skilled in the art can readily identify corresponding sequence positions between viral genomes or proteins that might differ in length, guided by sequence alignments as well as the positions of open reading frames, well-known RNA features such as gene-start and gene-end signals, and amino acid sequence features.

The full-length recombinant RSV wt backbone was described previously (Collins et al PNAS 92:11563-11567), and it is well recognized that the viral genome can readily accommodate numerous incidental modifications such as the insertion of restriction enzyme cleavage sites or point mutations due to naturally occurring sequence variation (Collins et al PNAS 92:11563-11567; Whitehead et al J Virol 72:4467-4471). In many cases, the recombinant wt RSV that was used is a version called D46/D6120 (or 6120) that differs from the full length recombinant wt parent by the deletion of 112 nucleotides from the downstream nontranslated region of the SH gene, and also contains the introduction of five translationally silent nucleotide changes into the downstream end of the SH open reading frame (Bukreyev et al J Virol 75:12128-12140, 2001). This deletion and these silent [at the amino acid level] changes were made to stabilize the cDNA during propagation in bacteria. Importantly, they did not detectably affect in the viral phenotype in cell culture or in mice, and thus the 6120 virus is considered to be a wt virus.

Recombinant RSV Mutants

A number of attenuated RSV strains as candidate vaccines for intranasal administration have been developed using multiple rounds of chemical mutagenesis to introduce multiple mutations into a virus which had already been attenuated during cold-passage (e.g., Connors et al., Virology 208: 478-484 (1995); Crowe et al., Vaccine 12: 691-699 (1994); and Crowe et al., Vaccine 12: 783-790 (1994)). Evaluation in rodents, chimpanzees, adults and infants indicate that certain of these candidate vaccine strains are relatively stable genetically, are highly immunogenic, and may be satisfactorily attenuated. However, further studies indicated that genetic instability can occur and can be substantial (Karron et al, JID 191:1093-1104; Lin et al Virus Research 115:9-15, 2006). Nucleotide sequence analysis of some of these attenuated viruses identified nucleotide and amino acid changes, and the introduction of these changes individually and in combination into wild type recombinant virus identified a number of attenuating mutations. The identification of attenuating mutations also made it possible to monitor the stability of specific mutations in vaccine candidates. The present disclosure provides means of increasing the stability of attenuating mutations and phenotypes. Consistent with this understanding, disclosed herein are additional mutations at both the nucleotide and amino acid levels that also produce attenuated viruses but have increased stability. The mutations identified herein can thus be introduced as desired, singly or in combination, to calibrate a vaccine virus to an appropriate level of attenuation, immunogenicity, genetic resistance to reversion from an attenuated phenotype, etc., as desired. In some embodiments, the described mutations may be used to modify a wildtype strain of RSV to create a new vaccine virus. In other embodiments, the described mutations may be used to modify a previously attenuated strain of RSV to create a new vaccine virus by augmenting an existing vaccine stain of RSV.

In some embodiments the mutated RSVs described herein may be temperature sensitive (ts), such that viral replication is reduced, relative to wild-type RSV (or other RSV), at increased temperatures. The level of temperature sensitivity of replication in an exemplary attenuated RSV of the invention is determined by comparing its replication at a permissive temperature with that at several restrictive temperatures. The lowest temperature at which the replication of the virus is reduced 100-fold or more in comparison with its replication at the permissive temperature is termed the shutoff temperature. In experimental animals and humans, both the replication and virulence of RSV correlate with the mutant's shutoff temperature. Replication of mutants with a shutoff temperature of 39° C. is moderately restricted, whereas mutants with a shutoff of 38° C. replicate less well and symptoms of illness are mainly restricted to the upper respiratory tract. A virus with a shutoff temperature of 35 to 37° C. will typically be fully attenuated in humans. Thus, the attenuated RSV of the invention which is ts will have a shutoff temperature in the range of about 35 to 39° C., and preferably from 35 to 38° C. The addition of a ts mutation to a partially attenuated strain produces multiply attenuated virus and may be useful in the production of a vaccine. Accordingly, the amino acid mutations and deletions described herein may be incorporated into an exiting RSV strain known to be temperature sensitive in order to produce a new virus strain that is further attenuated or less likely to revert to a less attenuated form.

In addition to RSVs having the particular mutations, and the combinations of those mutations, described herein, the disclosed viruses may be modified further as would be appreciated by those skilled in the art. For example, the described RSVs may have one or more of its proteins deleted. For example, any of the NS1, NS2, SH, G, or M2-2 proteins could be mutated or deleted. Alternatively, a heterologous gene from a different organism could be added to the genome or antigenome so that the described RSV expressed or incorporated that protein upon infecting a cell and replicating. Furthermore, those skilled in the art will appreciate that previously defined mutations known to have an effect on RSV may be combined with one or more of any of the mutations described herein to produce an RSV with desirable attenuation or stability characteristics.

The specific mutations which have been introduced into RSV are identified by sequence analysis and comparison to the parental background, e.g., a cpRSV derivative or wt background. In one embodiment, the rA2cp248/404/1030ΔSH virus could be recombinantly modified to have an N→G amino acid change at residue 1321 of the L protein. In one embodiment, the rA2cp248/404/1030ΔSH virus could be recombinantly modified to have a N→E amino acid change at residue 1321 of the L protein. In another embodiment, the rA2cp248/404/1030ΔSH virus could be recombinantly modified to have a N→P amino acid change at residue 1321 of the L protein. And in yet another embodiment, the rA2cp248/404/1030ΔSH virus could be recombinantly modified to have a N→K amino acid change at residue 1321 of the L protein. In one such embodiment, a change of this nature could be produced by altering the nucleic acid sequence of the L protein such that the codon encoding the amino acid at residue 1321 is GGT (encoding glycine) rather than AAT (encoding asparagine). In another embodiment, amino acid residue 1313 of the L protein could be changed to a lysine, such as by introduction of the codon AAA. In yet another embodiment, the genome or antigenome of the rA2cp248/404/1030ΔSH virus could be altered to have a mutation at amino acid residue 1313 of the L protein. For example, residue 1313, which is a serine in the wt sequence, could be changed to a cysteine. Alternatively, in another embodiment, the codon encoding S1313 in the wt RSV genome could be deleted completely; producing an amino acid deletion mutant RSV. As exemplified herein, mutations of this sort have phenotypic characteristics consistent with that of an attenuated virus; therefore, it may be desirable to use them singly, or, alternatively, in combination with other mutations known to confer an attenuated phenotype. For example, the RSV strain rA2cp248/404/1030ΔSH, or another existing attenuated RSV strain, could be modified using a combination of the individual mutations and deletions described at positions 1321 and 1313 of the L protein. The provided description of these new mutations and their use in making recombinant alterations of existing attenuated RSV strains would render such combinations apparent to those of skill in the art.

In some embodiments, the mutations described herein, when used either alone or in combination with another mutation, can provide for different levels of virus attenuation, providing the ability to adjust the balance between attenuation and immunogenicity, and can provide a more stable genotype than that of the parental virus. In one such embodiment, an RSV having a deletion of amino acid 1313 of the wt L protein (Δ1313) may have a lower $T_{SH}$ than its parental RSV strain. In addition, a virus with this mutation may exhibit significant attenuation, relative to its parent strain. In addition, this virus may have a genetic resistance to phenotypic reversion, and, thus be considered a desirable vaccine candidate as is, or may be combined with other mutations to give rise to a new virus strain. In this regard there are numerous attenuating mutations known, either in combination or individually, to exist for RSV, such as (i) those characterized for cptsRSV 248, cptsRSV 530, cptsRSV 248/404, cptsRSV 530/1009, cpts248/955, cpts530/1030, or (ii) deletion of part or all of the NS1, NS2, SH, or G genes or the M2-2 open reading frame, or (iii) replacement of human RSV genes with those from relative related animal-specific paramyxovirus such as bovine RSV to introduce host range restriction, or (iv) attenuation introduced by rearranging or adding genes in the RSV genome, as well as other means of attenuation disclosed herein, see for example: Crowe J E et al., Vaccine, 1994 June; 12(8): 691-9; Crowe J E et al., Vaccine, 1994 July; 12(9):783-90; Hsu K H, Vaccine, 1995 April; 13(5):509-15; Connors M, et al., Virology, 1995 Apr. 20; 208(2):478-84; Crowe J E et al., Virus Genes, 1996; 13(3):269-73; Firestone C Y, et al., Virology, 1996 Nov. 15; 225(2):419-22; Juhasz K, et al., J. Virol., 1997 August; 71(8):5814-9; Whitehead S S, et al., J. Virol. 1999 February; 73(2):871-7; Bukreyev A, et al., J Virol. 1997 December; 71(12):8973-82; Whitehead S S, et al., J Virol. 1998 May; 72(5):4467-71; Whitehead S S, et al., Virology. 1998 Aug. 1; 247(2):232-9; Bukreyev A, et al., Proc Natl Acad Sci USA. 1999 Mar. 2; 96(5):2367-72; Whitehead S S, et al., J Virol. 1999 April; 73(4):3438-42; Juhasz K, et al., Vaccine. 1999 Mar. 17; 17(11-12):1416-24; Whitehead S S, et al., J Virol. 1999 December; 73(12):9773-80; Buchholz U J, et al., J Virol. 2000 February; 74(3):1187-99; Teng M N, J Virol. 2000 October; 74(19):9317-21; Krempl C, et a., J Virol. 2002 December; 76(23):11931-42; and Teng M N, et al., Virology. 2001 Oct. 25; 289(2):283-96.

Thus, in addition to, or in combination with, attenuating mutations adopted from biologically derived RSV mutants, the present invention also provides entirely new methods for identifying novel sites in the RSV genome that are commonly mutated to allow for reversion of an attenuated virus strain. In accordance with this aspect of the invention, those skilled in the art will appreciate that attenuated RSV, or other paramyxovirus, strains can now be assessed as described herein to identify amino acid changes that allow attenuated strains to revert, or evolve to have decreased attenuation.

Once identified, these amino acid residues can be themselves altered, or deleted, to provide for creation of a more stable attenuated virus.

Accordingly, provided herein are methods for enhancing the genetic stability of, and identifying the genetic basis of phenotypic reversion of, attenuated virus strains. The provided methods consist of obtaining or identifying an attenuated, or mutant, virus strain; culturing the virus in the presence of a selection condition that is less restrictive to a wild-type strain of the virus, relative to an attenuated, or mutated, strain; identifying mutated strains of the attenuated virus that exhibit reduced attenuation under the restrictive conditions than would an non-mutated attenuated virus; and assessing the genome of the mutated strain of the attenuated virus to identify the genetic basis for the reduced attenuation exhibited by the strain. Upon identifying the genetic alteration giving rise to reduced attenuation of the virus, mutations can be made in the genetic sequence of the attenuated virus strain to prevent the mutation conferring reduced attenuation from arising. The provided methods are applicable to any attenuated virus capable of evolving to become less attenuated due to genetic mutation when cultured under selective conditions. For exemplary purposes, the method is described in the context of RSV herein; however, those skilled in the art will readily understand that it may be applied generally.

Desired modifications of infectious recombinant RSV are typically selected to specify a desired phenotypic change, e.g., a change in viral growth, temperature sensitivity, ability to elicit a host immune response, attenuation, etc. As will be appreciated by those of ordinary skill in the art, these changes can be brought about by, e.g., mutagenesis of a parent RSV clone to ablate, introduce or rearrange a specific gene(s) or gene region(s) (e.g., a gene segment that encodes a protein structural domain, such as a cytoplasmic, transmembrane or extracellular domain, an immunogenic epitope, binding region, active site, etc.). Genes of interest in this regard include all of the genes of the RSV genome: 3'-NS1-NS2-N-P-M-SH-G-F-M2-L-5', as well as heterologous genes from other RSV, other viruses and a variety of other non-RSV sources as indicated herein. It will also be understood that modifications which simply alter or ablate expression of a selected gene can be used to further modify the virus strains described herein, e.g., by introducing a termination codon within a selected RSV coding sequence; changing the position of an RSV gene relative to an operably linked promoter; introducing an upstream start codon to alter rates of expression; modifying (e.g., by changing position, altering an existing sequence, or substituting an existing sequence with a heterologous sequence) GS and/or GE transcription signals to alter phenotype (e.g., growth, temperature restrictions on transcription, etc.); and various other deletions, substitutions, additions and rearrangements that specify quantitative or qualitative changes in viral replication, transcription of selected gene(s), or translation of selected protein(s).

In one aspect of the invention, a selected gene segment, such as one encoding a selected protein or protein region (e.g., a cytoplasmic tail, transmembrane domain or ectodomain, an epitopic site or region, a binding site or region, an active site or region containing an active site, etc.) from one RSV, can be substituted for a counterpart gene segment from the same or different RSV or other source, to yield novel recombinants having desired phenotypic changes compared to wild-type or parent RSV strains. For example, recombinants of this type may express a chimeric protein having a cytoplasmic tail and/or transmembrane domain of one RSV fused to an ectodomain of another RSV. Other exemplary recombinants of this type express duplicate protein regions, such as duplicate immunogenic regions. As used herein, "counterpart" genes, gene segments, proteins or protein regions, are typically from heterologous sources (e.g., from different RSV genes, or representing the same (i.e., homologous or allelic) gene or gene segment in different RSV strains). Typical counterparts selected in this context share gross structural features, e.g., each counterpart may encode a comparable structural "domain," such as a cytoplasmic domain, transmembrane domain, ectodomain, binding site or region, epitopic site or region, etc. Counterpart domains and their encoding gene segments embrace an assemblage of species having a range of size and amino acid (or nucleotide) sequence variations, which range is defined by a common biological activity among the domain or gene segment variants. For example, two selected protein domains encoded by counterpart gene segments within the invention may share substantially the same qualitative activity, such as providing a membrane spanning function, a specific binding activity, an immunological recognition site, etc. More typically, a specific biological activity shared between counterparts, e.g., between selected protein segments or proteins, will be substantially similar in quantitative terms, i.e., they will not vary in respective quantitative activity profiles by more than 30%, preferably by no more than 20%, more preferably by no more than 5-10%.

In alternative aspects of the invention, the infectious RSV produced from a cDNA-expressed genome or antigenome can be any of the RSV or RSV-like strains, e.g., human, bovine, murine, etc., or of any pneumovirus or metapneumovirus, e.g., pneumonia virus of mice or avian metapneumovirus. To engender a protective immune response, the RSV strain may be one which is endogenous to the subject being immunized, such as human RSV being used to immunize humans. The genome or antigenome of endogenous RSV can be modified, however, to express RSV genes or gene segments from a combination of different sources, e.g., a combination of genes or gene segments from different RSV species, subgroups, or strains, or from an RSV and another respiratory pathogen such as human parainfluenza virus (PIV) (see, e.g., Hoffman et al., J. Virol. 71:4272-4277 (1997); Durbin et al., Virology 235(2):323-32 (1997); Murphy et al., U.S. Patent Application Ser. No. 60/047,575, filed May 23, 1997, and the following plasmids for producing infectious PIV clones: p3/7(131) (ATCC 97990); p3/7(131) 2G (ATCC 97889); and p218(131) (ATCC 97991); each deposited Apr. 18, 1997 under the terms of the Budapest Treaty with the American Type Culture Collection (ATCC) of 10801 University Blvd., Manassas, Va. 20110-2209, USA., and granted the above identified accession numbers.

In certain embodiments of the invention, recombinant RSV are provided wherein individual internal genes of a human RSV are replaced with, e.g., a bovine or other RSV counterpart, or with a counterpart or foreign gene from another respiratory pathogen such as PIV. Substitutions, deletions, etc. of RSV genes or gene segments in this context can include part or all of one or more of the NS1, NS2, N, P, M, SH, and L genes, or the M2-1 and M2-2 open reading frames, or non-immunogenic parts of the G and F genes. Also, human RSV cis-acting sequences, such as promoter or transcription signals, can be replaced with, e.g., their bovine RSV counterpart. Reciprocally, means are provided to generate live attenuated bovine RSV by inserting human attenuating genes or cis-acting sequences into a bovine RSV genome or antigenome background.

Thus, infectious recombinant RSV intended for administration to humans can be a human RSV that has been modified to contain genes from, e.g., a bovine RSV or a PIV, such as for the purpose of attenuation. For example, by inserting a gene or gene segment from PIV, a bivalent vaccine to both PIV and RSV is provided. Alternatively, a heterologous RSV species, subgroup or strain, or a distinct respiratory pathogen such as PIV, may be modified, e.g., to contain genes that encode epitopes or proteins which elicit protection against human RSV infection. For example, the human RSV glycoprotein genes can be substituted for the bovine glycoprotein genes such that the resulting bovine RSV, which now bears the human RSV surface glycoproteins and would retain a restricted ability to replicate in a human host due to the remaining bovine genetic background, elicits a protective immune response in humans against human RSV strains.

The ability to analyze and incorporate other types of attenuating mutations into infectious RSV for vaccine development extends to a broad assemblage of targeted changes in RSV clones. For example, deletion of the SH gene yields a recombinant RSV having novel phenotypic characteristics, including enhanced growth in cell culture and reduced replication in vivo. In the present invention, an SH gene deletion (or any other selected, non-essential gene or gene segment deletion), is combined in a recombinant RSV with one or more additional mutations specifying an attenuated phenotype, e.g., a point mutation adopted from a biologically derived attenuated RSV mutant. In exemplary embodiments, the SH, or NS2, or NS1 gene, or M2-2 open reading frame, is deleted in combination with one or more cp and/or is mutations adopted from cpts248/404, cpts530/1009, cpts530/1030, rA2cp248/404/1030ΔSH, Δ1313 or another selected mutant RSV strain, to yield a recombinant RSV having increased yield of virus, enhanced attenuation, and increased genetic or phenotypic stability, due to the combined effects of the different mutations. In this regard, any RSV gene which is not essential for growth, for example the SH, G, NS1, and NS2 genes, or M2-2 open reading frame, can be ablated or otherwise modified to yield desired effects on virulence, pathogenesis, immunogenicity and other phenotypic characters. For example, ablation by deletion of a non-essential gene such as SH results in enhanced viral growth in culture. Without wishing to be bound by theory, this effect is likely due in part to a reduced nucleotide length of the viral genome. In the case of one exemplary SH-deletion clone, the modified viral genome is 14,825 nt long, 398 nucleotides less than wild type. By engineering similar mutations that decrease genome size, e.g., in other coding or noncoding regions elsewhere in the RSV genome, such as in the P, M, F and M2 genes, the invention provides several readily obtainable methods and materials for improving RSV growth.

In addition, a variety of other genetic alterations can be produced in a recombinant RSV genome or antigenome for incorporation into infectious recombinant RSV, alone or together with one or more attenuating point mutations adopted from a biologically derived mutant RSV. As used herein, "heterologuous genes" refers to genes taken from different RSV strains or types or non-RSV sources. These heterologous genes can be inserted in whole or in part, the order of genes changed, gene overlap removed, the RSV genome promoter replaced with its antigenome counterpart, portions of genes removed or substituted, and even entire genes deleted. Different or additional modifications in the sequence can be made to facilitate manipulations, such as the insertion of unique restriction sites in various intergenic regions (e.g., a unique StuI site between the G and F genes) or elsewhere. Nontranslated gene sequences can be removed to increase capacity for inserting foreign sequences.

Deletions, insertions, substitutions and other mutations involving changes of whole viral genes or gene segments in recombinant RSV of the invention yield highly stable vaccine candidates, which are particularly important in the case of immunosuppressed individuals. Many of these mutations will result in attenuation of resultant vaccine strains, whereas others will specify different types of desired phenotypic changes. For example, certain viral genes are known which encode proteins that specifically interfere with host immunity (see, e.g., Kato et al., EMBO. J. 16:578-87 (1997). Ablation of such genes in vaccine viruses is expected to reduce virulence and pathogenesis and/or improve immunogenicity.

Other mutations within RSV of the present invention involve replacement of the 3' end of genome with its counterpart from antigenome, which is associated with changes in RNA replication and transcription. In addition, the intergenic regions (Collins et al., Proc. Natl. Acad. Sci. USA 83:4594-4598 (1986)) can be shortened or lengthened or changed in sequence content, and the naturally-occurring gene overlap (Collins et al., Proc. Natl. Acad. Sci. USA 84:5134-5138 (1987)) can be removed or changed to a different intergenic region by the methods described herein.

In another embodiment, a sequence surrounding a translational start site (preferably including a nucleotide in the −3 position) of a selected RSV gene is modified, alone or in combination with introduction of an upstream start codon, to modulate RSV gene expression by specifying up- or down-regulation of translation.

Alternatively, or in combination with other RSV modifications disclosed herein, RSV gene expression can be modulated by altering a transcriptional GS signal of a selected gene(s) of the virus. In one exemplary embodiment, the GS signal of NS2 is modified to include a defined mutation to superimpose a is restriction on viral replication.

Yet additional RSV clones within the invention incorporate modifications to a transcriptional GE signal. For example, RSV clones are provided which substitute or mutate the GE signal of the NS1 and NS2 genes for that of the N gene, resulting in decreased levels of readthrough mRNAs and increased expression of proteins from downstream genes. The resulting recombinant virus exhibits increased growth kinetics and increased plaque size, providing but one example of alteration of RSV growth properties by modification of a cis-acting regulatory element in the RSV genome.

In another embodiment, expression of the G protein is increased by modification of the G mRNA. The G protein is expressed as both a membrane bound and a secreted form, the latter form being expressed by translational initiation at a start site within the G gene translational open reading frame. The secreted form can account for as much as one-half of the expressed G protein. Ablation of the internal start site (e.g., by sequence alteration, deletion, etc.), alone or together with altering the sequence context of the upstream start site yields desired changes in G protein expression. Ablation of the secreted form of the G protein also will improve the quality of the host immune response to exemplary, recombinant RSV, because the soluble form of the G protein is thought to act as a "decoy" to trap neutralizing antibodies. Also, soluble G protein has been implicated in enhanced immunopathology due to its preferential stimulation of a Th2-biased response.

In alternative embodiments, levels of RSV gene expression are modified at the level of transcription. In one aspect, the position of a selected gene in the RSV gene map can be changed to a more promoter-proximal or promotor-distal position, whereby the gene will be expressed more or less efficiently, respectively. According to this aspect, modulation of expression for specific genes can be achieved yielding reductions or increases of gene expression from two-fold, more typically four-fold, up to ten-fold or more compared to wild-type levels. In one example, the NS2 gene (second in order in the RSV gene map) is substituted in position for the SH gene (sixth in order), yielding a predicted decrease in expression of NS2. Increased expression of selected RSV genes due to positional changes can be achieved up to 10-fold, 30-fold, 50-fold, 100-fold or more, often attended by a commensurate decrease in expression levels for reciprocally, positionally substituted genes.

In other exemplary embodiments, the F and G genes are transpositioned singly or together to a more promoter-proximal or promoter-distal site within the (recombinant) RSV gene map to achieve higher or lower levels of gene expression, respectively. These and other transpositioning changes yield novel RSV clones having attenuated phenotypes, for example due to decreased expression of selected viral proteins involved in RNA replication.

In yet other embodiments, RSV useful in a vaccine formulation can be conveniently modified to accommodate antigenic drift in circulating virus. Typically the modification will be in the G and/or F proteins. The entire G or F gene, or the segments encoding particular immunogenic regions thereof, is incorporated into the RSV genome or antigenome cDNA by replacement of the corresponding region in the infectious clone or by adding one or more copies of the gene such that several antigenic forms are represented. Progeny virus produced from the modified RSV cDNA are then used in vaccination protocols against the emerging strains. Further, inclusion of the G protein gene of RSV subgroup B as a gene addition will broaden the response to cover a wider spectrum of the relatively diverse subgroup A and B strains present in the human population.

An infectious RSV clone of the invention can also be engineered according to the methods and compositions disclosed herein to enhance its immunogenicity and induce a level of protection greater than that provided by infection with a wild-type RSV or an incompletely attenuated parental virus or clone. For example, an immunogenic epitope from a heterologous RSV strain or type, or from a non-RSV source such as PIV, can be added by appropriate nucleotide changes in the polynucleotide sequence encoding the RSV genome or antigenome. Recombinant RSV can also be engineered to identify and ablate (e.g., by amino acid insertion, substitution or deletion) epitopes associated with undesirable immunopathologic reactions. In other embodiments, an additional gene is inserted into or proximate to the RSV genome or antigenome which is under the control of an independent set of transcription signals. Genes of interest include, but are not limited to, those encoding cytokines (e.g., IL-2 through IL-15, especially IL-2, IL-6 and IL-12, etc.), gamma-interferon, and include those encoding cytokines (e.g., IL-2 through IL-15, especially IL-2, IL-6 and IL-12, etc.), gamma-interferon, and proteins rich in T helper cell epitopes. The additional protein can be expressed either as a separate protein or as a chimera engineered from a second copy of one of the RSV proteins, such as SH. This provides the ability to modify and improve the immune response against RSV both quantitatively and qualitatively.

In another aspect of the invention the recombinant RSV can be employed as a vector for protective antigens of other respiratory tract pathogens, such as PIV, e.g., by incorporating sequences encoding those protective antigens from PIV into the RSV genome or antigenome used to produce infectious vaccine virus, as described herein. In alternate embodiments, a modified RSV is provided which comprises a chimera of a RSV genomic or antigenomic sequence and at least one PIV sequence, for example a polynucleotide containing sequences from both RSV and PIV1, PIV2, PIV3 or bovine PIV. For example, individual genes of RSV may be replaced with counterpart genes from human PIV, such as the HN and/or F glycoprotein genes of PIV1, PIV2, or PIV3. Alternatively, a selected, heterologous gene segment, such as a cytoplasmic tail, transmembrane domain or ectodomain of HN or F of HPIV1, HPIV2, or HPIV3 can be substituted for a counterpart gene segment in, e.g., the same gene in an RSV clone, within a different gene in the RSV clone, or into a non-coding sequence of the RSV genome or antigenome. In one embodiment, a gene segment from HN or F of HPIV3 is substituted for a counterpart gene segment in RSV type A, to yield constructs encoding chimeric proteins, e.g. fusion proteins having a cytoplasmic tail and/or transmembrane domain of RSV fused to an ectodomain of RSV to yield a novel attenuated virus, and/or a multivalent vaccine immunogenic against both PIV and RSV.

In addition to the above described modifications to recombinant RSV, different or additional modifications in RSV clones can be made to facilitate manipulations, such as the insertion of unique restriction sites in various intergenic regions (e.g., a unique StuI site between the G and F genes) or elsewhere. Nontranslated gene sequences can be removed to increase capacity for inserting foreign sequences.

Introduction of the foregoing, defined mutations into an infectious RSV clone can be achieved by a variety of well-known methods. By "infectious clone" is meant cDNA or its product, synthetic or otherwise, which can be transcribed into genomic or antigenomic RNA capable of producing an infectious virus. The term "infectious" refers to a virus or viral structure that is capable of replicating in a cultured cell or animal or human host to produce progeny virus or viral structures capable of the same activity. Thus, defined mutations can be introduced by conventional techniques (e.g., site-directed mutagenesis) into a cDNA copy of the genome or antigenome. The use of antigenome or genome cDNA subfragments to assemble a complete antigenome or genome cDNA is well-known by those of ordinary skill in the art and has the advantage that each region can be manipulated separately (smaller cDNAs are easier to manipulate than large ones) and then readily assembled into a complete cDNA. Thus, the complete antigenome or genome cDNA, or any subfragment thereof, can be used as template for oligonucleotide-directed mutagenesis. A mutated subfragment can then be assembled into the complete antigenome or genome cDNA. Mutations can vary from single nucleotide changes to replacement of large cDNA pieces containing one or more genes or genome regions.

The ability to introduce defined mutations into infectious RSV has many applications, including the analyses of RSV molecular biology and pathogenesis. For example, the functions of the RSV proteins, including the NS1, NS2, SH, M2-1 and M2-2 proteins, can be investigated and manipulated by introducing mutations which ablate or reduce their level of expression, or which yield mutant protein. In one embodiment, RSV virus can be constructed so that expression of a viral gene, such as the SH gene, is ablated by deletion of the mRNA coding sequence and flanking transcription signals. These deletions are highly stable against genetic reversion, rendering the RSV clones derived therefrom particularly useful as vaccine agents.

Methods of Producing Recombinant RSV

The ability to produce infectious RSV from cDNA permits the introduction of specific engineered changes, including site specific attenuating mutations, gene deletion, gene start sequecen deletion or modification, and a broad spectrum of other recombinant changes, into the genome of a recombinant virus to produce an attenuated virus and, in some embodiments, effective RSV vaccine strains. Such engineered changes may, or may not, be based on biological mutations identified in other virus strains.

Described herein are infectious RSVs produced by recombinant methods, e.g., from cDNA. In one embodiment, infectious RSV is produced by the intracellular coexpression of a cDNA that encodes the RSV genomic RNA, together with those viral proteins necessary to generate a transcribing, replicating nucleocapsid, such as one or more sequences that encode major nucleocapsid (N) protein, nucleocapsid phosphoprotein (P), large (L) polymerase protein, and a transcriptional elongation factor M2-1 protein. Plasmids encoding other RSV, such as nonstructural protein 1 (NS1), nonstructural protein 2 (NS2), matrix protein (M), small hydrophobic protein (SH), glycoprotein (G), fusion protein (F), and protein M2-2, may also be included with these essential proteins. Accordingly, also described herein are isolated polynucleotides that encode the described mutated viruses, make up the described genomes or antigenomes, express the described genomes or antigenomes, or encode various proteins useful for making recombinant RSV in vitro. These polynucleotides can be included within or expressed by vectors in order to produce a recombinant RSV. Accordingly, cells transfected with the isolated polynucleotides or vectors are also within the scope of the invention and are exemplified herein. In addition, a number of methods relating to the described RSVs are also disclosed. For example, methods of producing the recombinant RSVs described herein are disclosed; as are methods producing an immune response to a viral protein in an animal, mammal or human.

The invention permits incorporation of biologically derived mutations, along with a broad range of other desired changes, into recombinant RSV vaccine strains. For example, the capability of producing virus from cDNA allows for incorporation of mutations occurring in attenuated RSV vaccine candidates to be introduced, individually or in various selected combinations, into a full-length cDNA clone, and the phenotypes of rescued recombinant viruses containing the introduced mutations to be readily determined. In exemplary embodiments, amino acid changes identified in attenuated, biologically-derived viruses, for example in a cold-passaged RSV (cpRSV), or in a further attenuated strain derived therefrom, such as a temperature-sensitive derivative of cpRSV (cptsRSV), are incorporated within recombinant RSV clones. These changes from a wild-type or biologically derived mutant RSV sequence specify desired characteristics in the resultant clones, e.g., an attenuated or further attenuated phenotype compared to a wild-type or incompletely attenuated parental RSV phenotype. In this regard, disclosed herein are novel RSV mutations that can be combined, either individually or in combination with one another, with preexisting attenuated RSV strains to produce viruses having desired characteristics, such as increased attenuation or enhanced genetic (and thereby phenotypic) stability in vitro and in vivo.

In addition to single and multiple point mutations and site-specific mutations, changes to recombinant RSV disclosed herein include deletions, insertions, substitutions or rearrangements of whole genes or gene segments. These mutations can affect small numbers of bases (e.g., from 15-30 bases, up to 35-50 bases or more), or large blocks of nucleotides (e.g., 50-100, 100-300, 300-500, 500-1,000 bases) depending upon the nature of the change (i.e., a small number of bases may be changed to insert or ablate an immunogenic epitope or change a small gene segment or delete one or more codons for purposes of attenuation, whereas large block(s) of bases are involved when genes or large gene segments are added, substituted, deleted or rearranged. These alterations will be understood by those of skill in the art based on prior work done with either RSV or related viruses. Viruses having block mutations of this sort can also be combined with the novel RSV mutations described herein, either individually or in combination with one another, to produce viruses having desired characteristics, such as increased attenuation or enhanced genetic (and thereby phenotypic) stability in vitro and in vivo.

In additional aspects, the invention provides for supplementation of mutations adopted from biologically derived RSV, e.g., cp and is mutations, many of which occur in the L gene, with additional types of mutations involving the same or different genes or RNA signals in a recombinant RSV clone. RSV encodes ten mRNAs and eleven proteins. Three of these are transmembrane surface proteins, namely the attachment G protein, fusion F protein involved in penetration, and small hydrophobic SH protein. While specific functions may be assigned to single proteins, it is recognized that these assignments are provisional and descriptive. G and F are the major viral neutralization and protective antigens. Four additional proteins are associated with the viral nucleocapsid, namely the RNA binding protein N, the phosphoprotein P, the large polymerase protein L, and the transcription elongation factor M2-1. The matrix M protein is part of the inner virion and probably mediates association between the nucleocapsid and the envelope. Finally, there are two nonstructural proteins, NS1 and NS2, of unknown function. These proteins can be selectively altered in terms of its expression level, or can be added, deleted, substituted or rearranged, in whole or in part, alone or in combination with other desired modifications, in a recombinant RSV to obtain novel infectious RSV clones. In addition, the RNA genome contains cis-acting signals, including but not limited to the leader and trailer regions as well as the transcription gene-start (GS) and gene-end (GE) signals that border each gene. These signals help control encapsidation, transcription, and replication, and may have other roles as well. These signals can be selectively altered to obtain novel RSV clones.

Provided herein are specific amino acid changes that may be used to give rise to desirable mutations of the RSV L protein. Those of skill in the art will be readily able to determine the alterations of the codon encoding the described amino acid, as the possible codons that may give rise to a particular amino acid sequence are well known in the art. In some embodiments, particular codon usage is preferred to impart the substitution of a particular amino acid residue at a particular location in the L protein (e.g., 1321K(AAA), 1321E(GAA), and 1313C(TGC) to name a few). In these instances, the particular codon usage is provided herein. That the entire L protein nucleotide sequence, or even partial flanking sequence, may not be provided will not hinder those of ordinary skill in the art from understanding where the codon change should be made, as the changes are provided relative to the biologically-derived, wild-type sequence of RSV A2 strain, the sequence of which is readily available to the public (e.g., GenBank accession number M74568).

The invention also provides methods for producing an infectious RSV from one or more isolated polynucleotides, e.g., one or more cDNAs. According to the present invention cDNA encoding a RSV genome or antigenome is constructed for intracellular or in vitro coexpression with the necessary viral proteins to form infectious RSV. By "RSV antigenome" is meant an isolated positive-sense polynucleotide molecule which serves as the template for the synthesis of progeny RSV genome. Preferably a cDNA is constructed which is a positive-sense version of the RSV genome, corresponding to the replicative intermediate RNA, or antigenome, so as to minimize the possibility of hybridizing with positive-sense transcripts of the complementing sequences that encode proteins necessary to generate a transcribing, replicating nucleocapsid, i.e., sequences that encode N, P, L and M2-1 protein.

A native RSV genome typically comprises a negative-sense polynucleotide molecule which, through complementary viral mRNAs, encodes eleven species of viral proteins, i.e., the nonstructural proteins NS1 and NS2, N, P, matrix (M), small hydrophobic (SH), glycoprotein (G), fusion (F), M2-1, M2-2, and L, substantially as described in Mink et al., Virology 185: 615-624 (1991), Stec et al., Virology 183: 273-287 (1991), and Connors et al., Virol. 208:478-484 (1995). For purposes of the present invention the genome or antigenome of the recombinant RSV of the invention need only contain those genes or portions thereof necessary to render the viral or subviral particles encoded thereby infectious. Further, the genes or portions thereof may be provided by more than one polynucleotide molecule, i.e., a gene may be provided by complementation or the like from a separate nucleotide molecule.

By recombinant RSV is meant a RSV or RSV-like viral or subviral particle derived directly or indirectly from a recombinant expression system or propagated from virus or subviral particles produced therefrom. The recombinant expression system will employ a recombinant expression vector which comprises an operably linked transcriptional unit comprising an assembly of at least a genetic element or elements having a regulatory role in RSV gene expression, for example, a promoter, a structural or coding sequence which is transcribed into RSV RNA, and appropriate transcription initiation and termination sequences.

To produce infectious RSV from cDNA-expressed genome or antigenome, the genome or antigenome is coexpressed with those RSV proteins necessary to (i) produce a nucleocapsid capable of RNA replication, and (ii) render progeny nucleocapsids competent for both RNA replication and transcription. Transcription by the genome nucleocapsid provides the other RSV proteins and initiates a productive infection. Additional RSV proteins needed for a productive infection can also be supplied by coexpression.

Alternative means to construct cDNA encoding the genome or antigenome include by reverse transcription-PCR using improved PCR conditions (e.g., as described in Cheng et al., Proc. Natl. Acad. Sci. USA 91:5695-5699 (1994); Samal et al., J. Virol 70:5075-5082 (1996)) to reduce the number of subunit cDNA components to as few as one or two pieces. In other embodiments, different promoters can be used (e.g., T3, SP6) or different ribozymes (e.g., that of hepatitis delta virus). Different DNA vectors (e.g., cosmids) can be used for propagation to better accommodate the large size genome or antigenome.

The N, P, L and M2-1 proteins are encoded by one or more expression vectors which can be the same or separate from that which encodes the genome or antigenome, and various combinations thereof. Additional proteins may be included as desired, encoded by its own vector or by a vector encoding a N, P, L, or M2-1 protein or the complete genome or antigenome. Expression of the genome or antigenome and proteins from transfected plasmids can be achieved, for example, by each cDNA being under the control of a promoter for T7 RNA polymerase, which in turn is supplied by infection, transfection or transduction with an expression system for the T7 RNA polymerase, e.g., a vaccinia virus MVA strain recombinant which expresses the T7 RNA polymerase (Wyatt et al., Virology, 210:202-205 (1995)). The viral proteins, and/or T7 RNA polymerase, can also be provided from transformed mammalian cells, or by transfection of preformed mRNA or protein.

Alternatively, synthesis of antigenome or genome can be done in vitro (cell-free) in a combined transcription-translation reaction, followed by transfection into cells. Or, antigenome or genome RNA can be synthesized in vitro and transfected into cells expressing RSV proteins.

Uses of RSV Mutant Viruses

To select candidate vaccine viruses from the host of recombinant RSV strains provided herein, the criteria of viability, efficient replication in vitro, attenuation in vivo, immunogenicity, and phenotypic stability are determined according to well known methods. Viruses which will be most desired in vaccines of the invention must maintain viability, must replicate sufficiently in vitro well under permissive conditions to make vaccine manufacture possible, must have a stable attenuation phenotype, must exhibit replication in an immunized host (albeit at lower levels), and must effectively elicit production of an immune response in a vaccine sufficient to confer protection against serious disease caused by subsequent infection from wild-type virus. Clearly, the heretofore known and reported RS virus mutants do not meet all of these criteria. Indeed, contrary to expectations based on the results reported for known attenuated RSV, viruses of the invention are not only viable and more attenuated then previous mutants, but are more stable genetically in vivo than those previously studied mutants.

To propagate a RSV virus for vaccine use and other purposes, a number of cell lines which allow for RSV growth may be used. RSV grows in a variety of human and animal cells. Preferred cell lines for propagating attenuated RS virus for vaccine use include DBS-FRhL-2, MRC-5, and Vero cells. Highest virus yields are usually achieved with epithelial cell lines such as Vero cells. Cells are typically inoculated with virus at a multiplicity of infection ranging from about 0.001 to 1.0, or more, and are cultivated under conditions permissive for replication of the virus, e.g., at about 30-37° C. and for about 3-10 days, or as long as necessary for virus to reach an adequate titer. Temperature-sensitive viruses often are grown using 32° C. as the "permissive temperature." Virus is removed from cell culture and separated from cellular components, typically by well known clarification procedures, e.g., centrifugation, and may be further purified as desired using procedures well known to those skilled in the art.

RSV which has been attenuated as described herein can be tested in various well known and generally accepted in vitro and in vivo models to confirm adequate attenuation, resistance to phenotypic reversion, and immunogenicity for vaccine use. In in vitro assays, the modified virus, which can be a multiply attenuated, biologically derived or recombinant RSV, is tested for temperature sensitivity of virus replication or "ts phenotype," and for the small plaque phenotype. Modified viruses are further tested in animal models of RSV infection. A variety of animal models (e.g., murine, cotton rat, and primate) have been described and are known to those skilled in the art.

In accordance with the foregoing description and based on the Examples below, the invention also provides isolated, infectious RSV compositions for vaccine use. The attenuated virus which is a component of a vaccine is in an isolated and typically purified form. By isolated is meant to refer to RSV which is in other than a native environment of a wild-type virus, such as the nasopharynx of an infected individual. More generally, isolated is meant to include the attenuated virus as a component of a cell culture or other artificial medium. For example, attenuated RSV of the invention may be produced by an infected cell culture, separated from the cell culture and added to a stabilizer which contains other non-naturally occurring RSVs.

RSV vaccines of the invention contain as an active ingredient an immunogenically effective amount of RSV produced as described herein. Biologically derived or recombinant RSV can be used directly in vaccine formulations. The biologically derived or recombinantly modified virus may be introduced into a host with a physiologically acceptable carrier and/or adjuvant. Useful carriers are well known in the art, and include, e.g., water, buffered water, 0.4% saline, 0.3% glycine, hyaluronic acid and the like. The resulting aqueous solutions may be packaged for use as is, or lyophilized, the lyophilized preparation being combined with a sterile solution prior to administration, as mentioned above. The compositions may contain pharmaceutically acceptable auxiliary substances as required to approximate physiological conditions, which include, but are not limited to, pH adjusting and buffering agents, tonicity adjusting agents, wetting agents and the like, for example, sodium acetate, sodium lactate, sodium chloride, potassium chloride, calcium chloride, sucrose, magnesium sulfate, phosphate buffers, HEPES (4-(2-hydroxyethyl)-1-piperazineethanesulfonic acid) buffer, sorbitan monolaurate, and triethanolamine oleate. Acceptable adjuvants include incomplete Freund's adjuvant, aluminum phosphate, aluminum hydroxide, or alum, which are materials well known in the art. Preferred adjuvants also include Stimulon™ QS-21 (Aquila Biopharmaceuticals, Inc., Worcester, Mass.), MPL™ (3-0-deacylated monophosphoryl lipid A; RIBI ImmunoChem Research, Inc., Hamilton, Mont.), and interleukin-12 (Genetics Institute, Cambridge, Mass.).

Upon immunization with a RSV vaccine composition as described herein, via injection, aerosol, droplet, oral, topical or other route, the immune system of the host responds to the vaccine by producing antibodies specific for RSV virus proteins, e.g., F and G glycoproteins. As a result of the vaccination the host becomes at least partially or completely immune to RSV infection, or resistant to developing moderate or severe RSV disease, particularly of the lower respiratory tract.

The host to which the vaccine is administered can be any mammal susceptible to infection by RSV or a closely related virus and capable of generating a protective immune response to antigens of the vaccinizing strain. Thus, suitable hosts include humans, non-human primates, bovine, equine, swine, ovine, caprine, lagamorph, rodents, such as mice or cotton rats, etc. Accordingly, the invention provides methods for creating vaccines for a variety of human and veterinary uses.

The vaccine compositions containing the attenuated RSV of the invention are administered to a subject susceptible to or otherwise at risk of RS virus infection in an "immunogenically effective dose" which is sufficient to induce or enhance the individual's immune response capabilities against RSV. An RSV vaccine composition may be administered to a subject via injection, aerosol delivery, nasal spray, nasal droplets, oral inoculation, or topical application. In the case of human subjects, the attenuated virus of the invention is administered according to well established human RSV vaccine protocols (Karron et al JID 191:1093-104, 2005). Briefly, adults or children are inoculated intranasally via droplet with an immunogenically effective dose of RSV vaccine, typically in a volume of 0.5 ml of a physiologically acceptable diluent or carrier. This has the advantage of simplicity and safety compared to parenteral immunization with a non-replicating vaccine. It also provides direct stimulation of local respiratory tract immunity, which plays a major role in resistance to RSV. Further, this mode of vaccination effectively bypasses the immunosuppressive effects of RSV-specific maternally-derived serum antibodies, which typically are found in the very young. Also, while the parenteral administration of RSV antigens can sometimes be associated with immunopathologic complications, this has never been observed with a live virus.

In all subjects, the precise amount of RSV vaccine administered and the timing and repetition of administration will be determined by various factors, including the patient's state of health and weight, the mode of administration, the nature of the formulation, etc. Dosages will generally range from about $10^3$ to about $10^6$ plaque forming units ("PFU") or more of virus per patient, more commonly from about $10^4$ to $10^5$ PFU virus per patient. In one embodiment, about $10^5$ to $10^6$ PFU per patient could be administered during infancy, such as between 1 and 6 months of age, and one or more additional booster doses could be given 2-6 months or more later. In another embodiment, young infants could be given a dose of about $10^5$ to $10^6$ PFU per patient at approximately 2, 4, and 6 months of age, which is the recommended time of administration of a number of other childhood vaccines. In yet another embodiment, an additional booster dose could be administered at approximately 10-15 months of age. In any event, the vaccine formulations should provide a quantity of attenuated RSV of the invention sufficient to effectively stimulate or induce an anti-RSV immune response (an "effective amount"). The resulting immune response can be characterized by a variety of methods. These include taking samples of nasal washes or sera for analysis of RSV-specific antibodies, which can be detected by tests including, but not limited to, complement fixation, plaque neutralization, enzyme-linked immunosorbent assay, luciferase-immunoprecipitation assay, and flow cytometry. In addition, immune responses can be detected by assay of cytokines in nasal washes or sera, ELISPOT of immune cells from either source, quantitative RT-PCR or microarray analysis of nasal wash or serum samples, and restimulation of immune cells from nasal washes or serum by re-exposure to viral antigen in vitro and analysis for the production or display of cytokines, surface markers, or other immune correlates meaures by flow cytometry or for cytotoxic activity against indicator target cells displaying RSV antigens. In this regard, individuals are also monitored for signs and symptoms of upper respiratory illness. As with administration to chimpanzees, the attenuated virus of the vaccine grows in the nasopharynx of vaccinees at levels approximately 10-fold or more lower than wild-type virus, or approximately 10-fold or more lower when compared to levels of incompletely attenuated RSV.

In some embodiments, neonates and infants are given multiple doses of RSV vaccine to elicit sufficient levels of immunity. Administration may begin within the first month of life, and at intervals throughout childhood, such as at two months, four months, six months, one year and two years, as necessary to maintain sufficient levels of protection against natural RSV infection. In other embodiments, adults who are particularly susceptible to repeated or serious RSV infection, such as, for example, health care workers, day care workers, family members of young children, the elderly, individuals with compromised cardiopulmonary function, are given multiple doses of RSV vaccine to establish and/or maintain protective immune responses. Levels of induced immunity can be monitored by measuring amounts of neutralizing secretory and serum antibodies, and dosages adjusted or vaccinations repeated as necessary to maintain desired levels of protection. Further, different vaccine viruses may be indicated for administration to different recipient groups. For example, an engineered RSV strain expressing a cytokine or an additional protein rich in T cell epitopes may be particularly advantageous for adults rather than for infants. Vaccines produced in accordance with the present invention can be combined with viruses of the other subgroup or strains of RSV to achieve protection against multiple RSV subgroups or strains, or selected gene segments encoding, e.g., protective epitopes of these strains can be engineered into one RSV clone as described herein. In such embodiments, the different viruses can be in admixture and administered simultaneously or present in separate preparations and administered separately. For example, as the F glycoproteins of the two RSV subgroups differ by only about 11% in amino acid sequence, this similarity is the basis for a cross-protective immune response as observed in animals immunized with RSV or F antigen and challenged with a heterologous strain. Thus, immunization with one strain may protect against different strains of the same or different subgroup.

The vaccines of the invention elicit production of an immune response that may be protective against, or reduce the magnitude of serious lower respiratory tract disease, such as pneumonia and bronchiolitis when the individual is subsequently infected with wild-type RSV. While the naturally circulating virus is still capable of causing infection, particularly in the upper respiratory tract, there is a very greatly reduced possibility of rhinitis as a result of the vaccination and possible boosting of resistance by subsequent infection by wild-type virus. Following vaccination, there may be detectable levels of host engendered serum and, in some instances, secretory antibodies which are capable of neutralizing homologous (of the same subgroup) wild-type virus in vitro and in vivo. In many instances the host antibodies will also neutralize wild-type virus of a different, non-vaccine subgroup.

The level of attenuation of vaccine virus may be determined by, for example, quantifying the amount of virus present in the respiratory tract of an immunized host and comparing the amount to that produced by wild-type RSV or other attenuated RS viruses which have been evaluated as candidate vaccine strains. For example, the attenuated virus of the invention will have a greater degree of restriction of replication in the upper respiratory tract of a highly susceptible host, such as a chimpanzee, compared to the levels of replication of wild-type virus, e.g., 10- to 1000-fold less. In order to further reduce the development of rhinorrhea, which is associated with the replication of virus in the upper respiratory tract, an ideal vaccine candidate virus should exhibit a restricted level of replication in both the upper and lower respiratory tract. However, the attenuated viruses of the invention must be sufficiently infectious and immunogenic in humans to confer protection in vaccinated individuals. Methods for determining levels of RS virus in the nasopharynx of an infected host are well known in the literature. Specimens are obtained by aspiration or washing out of nasopharyngeal secretions and virus quantified in tissue culture or other by laboratory procedure. See, for example, Belshe et al., J. Med. Virology 1:157-162 (1977), Friedewald et al., J. Amer. Med. Assoc. 204:690-694 (1968); Gharpure et al., J. Virol. 3:414-421 (1969); and Wright et al., Arch. Ges. Virusforsch. 41:238-247 (1973). The virus can conveniently be measured in the nasopharynx of host animals, such as chimpanzees.

The following examples are provided by way of illustration, not limitation.

Example 1—Attempts to Generate Deletion Mutants in RSV

Phenotypic stability is an important feature of a live-attenuated vaccine. Mutations based on nucleotide substitution are prone to reversion in RNA viruses due to the inherently high mutation rate of these viruses. In a few isolated cases, increased stability of mutant phenotypes based on amino acid substitution has been achieved by deletion of one or more codons, since deletions often are more refractory to reversion than are substitutions. For example, a promising recombinantly derived HPIV2 live vaccine candidate contains deletion of codons 1724-1725 in the L polymerase protein (Nolan et al Vaccine 25:6409-6422, 2007). Also, vaccine candidates of HPIV1 have been developed involving deletion involving codons 168-170 of the C protein and codons 1710-1711 of the L protein (Bartlett et al Virology J 4:67, 2007). In each case, the site of deletion was guided by the previous identification of biologically-derived attenuating point mutations at that site in related viruses. However, these few recombinant examples notwithstanding, deletion mutations involving amino acids are very rare in viable biologically-derived mutants compared to the frequent occurrence of substitutions, supporting the idea that deletions are less well tolerated than substitutions. Therefore, they are not readily generated, and their recovery is unpredictable. Even when it is possible to isolate a deletion mutant, that virus must retain a high degree of replicative fitness under permissive conditions to be useful in a live vaccine, given the need to achieve satisfactory virus titers for vaccine manufacture.

Attempts were made to introduce small deletion mutations into RSV in order to identify stable attenuating mutations. Initially, these efforts focused mainly on several amino acid substitution mutations that were previously identified in biologically-derived RSV mutants and had been confirmed in recombinant virus to individually confer ts and attenuation phenotypes. Deletions were attempted at these sites with the expectation that, since these sites have been shown to accommodate amino acid substitutions without reducing replication at permissive temperatures, these regions would be particularly tolerant of mutation. This same strategy had led to the successful identification of the recombinant deletion mutations described above for HPIV1 and HPIV2. RSV mutants were prepared that included mutations at the following sites in the L protein: F521L ("530" mutation), Q831L ("248" mutation), M1169V ("1009" mutation), and Y1321N ("1030" mutation). In addition, an attenuating point mutation (I1103V in the L protein) that had been identified in bovine PIV3 (BPIV3) (Haller et al Virology 288:342-350 2001) was also included. For the mutation from BPIV3, the amino acid sequence of the BPIV3 L protein was aligned with that of RSV in order to identity the corresponding site in RSV L, which was identified as RSV L position 1165. Unexpectedly, however, it was found that deletion of each of these codons individually resulted in a failure to recover infectious virus in four independent attempts each, under conditions where the attenuating amino acid substitution could be recovered in parallel as a control in each of the four attempts to show that the conditions were favorable to recovery (Table 1). In each case, the L gene of the antigenic cDNA (representing 43% of the viral genome) was completely sequenced and confirmed to be correct. Attempts were also made to recover mutations involving deletion of one or more nearby codons (Table 1). For example, with regard to the "530" mutation at position 521, attempts also were made to recover a mutation involving position 522. With regard to the "248" mutation at position 831, attempts also were made to delete both codons 830 and 831, as well as codons 831 and 832. With regard to the BPIV3 I1103V mutation, attempts also were made to delete position 1164. With regard to the "1009" mutation at position 1169, deletions at positions 1170, 1172, 1176, 1178 also were attempted. With regard to the "1030" mutation at position 1321, attempts also were made to delete positions 1320 plus 1321, and 1321 plus 1322, and 1320 alone. However, none of these various additional deletions in the L protein could be recovered in infectious virus in multiple attempts with two exceptions. The first exception was that virus was recovered from the ΔR1170 mutant in 1 of 4 attempts. However, sequence analysis showed that this virus had acquired a 3-nucleotide insertion of AAA at the point of deletion, replacing the deletion of arginine with a lysine residue. Thus, it was not a true recovery of a deletion mutation. As the second exception, virus was recovered from the ΔN1172 mutant in 1 of 4 attempts. However, sequence analysis showed that this virus had acquired a 3-nucleotide insert of AAA at the point of deletion, replacing the deletion of asparagine with a lysine residue. Thus, this also was not a true recovery of a deletion mutation.

As will be described in Example 5, these studies also identified two attenuating mutations, E649D and Q874H, that spontaneously appeared during passage of an attenuated virus in cell culture in an attempt to evaluate its genetic stability. The identification of these two spontaneous mutations suggested that these sites, and ones nearby, might be amenable for single-codon deletion mutations. Therefore, attempts were made to recover viruses bearing single-codon deletions at positions 646, 649, 653, 874, 850, 857, 858, 872, 875, 876, 879, and 882. However, none of these could be recovered (data not shown).

Taken together, these results showed that the recovery of codon-deletion mutants was not readily achieved even at sites previously shown to accommodate amino acid substitutions in RSV, nor at a site identified by amino acid sequence alignment as corresponding to a substitution mutation at position 1103 in BPIV3. Recovery also was not possible at nearby sites. Thus, deletion of one or more codons in the RSV L polymerase protein frequently resulted in an inability to recover the virus, presumably due to a lethal effect of the deletion. In the two cases that could be recovered, the RSV polymerase apparently inserted three adenosine residues at the point of deletion to create a lysine codon, showing that the codon-deletion mutations that appeared to be recoverable in this Example in fact were not stable.

TABLE 1

Unsuccessful attempts to recover additional mutations involving deletion (Δ) of one or two codons in the RSV L protein.

| Amino Acid[a] | codons | RSV nt[b] | Number of Recovery attempts | Recovery | Additional information |
|---|---|---|---|---|---|
| F521L [c,d] | TTC to CTA | 10058-60 | 4 | 4/4 | RSV "530" mutation |
| ΔF521 [d] | TTC | 10058-60 | 4 | 0/4 | |
| ΔY522 | TAT | 10061-3 | 4 | 0/4 | |
| Q831L [c,e] | CAA to CTA | 10988-90 | 4 | 4/4 | RSV "248" mutation |
| ΔQ831 [e] | CAA | 10988-90 | 4 | 0/4 | |
| ΔQA 831 + 832 | CAA GCA | 10988-93 | 4 | 0/4 | |
| ΔAQ 830 + 831 | GCT CAA | 10985-90 | 4 | 0/4 | |
| ΔR1164 | AGA | 11987-9 | 4 | 0/4 | |
| ΔA1165 [f] | GCC | 11990-2 | 4 | 0/4 | Corresponds to position of BPIV3 I1103V |
| ΔM1169 [g] | ATG | 12002-4 | 4 | 0/4 | Position of RSV "1009" deletion |
| ΔR1170 | AGG | 12005-7 | 4 | 1/4 | Sequence analysis revealed a 3 nt insertion (codon AAA), resulting in R1170K mutation |
| ΔN1172 | AAC | 12011-3 | 4 | 1/4 | Sequence analysis revealed attempts a 3 nt insertion (codon AAA), resulting in N1172K mutation |
| ΔL1176 | CTT | 12023-5 | 3 | 0/3 | |
| ΔR1178 | AGG | 12029-31 | 4 | 0/4 | |
| ΔY1321N [c,h] | TAT to AAT | 12458-60 | 6 | 6/6 | RSV "1030" mutation |
| ΔY1321 [h] | TAT | 12458-60 | 6 | 0/6 | |
| ΔTY 1320 + 1321 | ACA TAT | 12455-60 | 6 | 0/6 | |

TABLE 1-continued

Unsuccessful attempts to recover additional mutations involving deletion (Δ) of one or two codons in the RSV L protein.

| Amino Acid[a] | codons | RSV nt[b] | Number of Recovery attempts | Recovery | Additional information |
|---|---|---|---|---|---|
| ΔYE 1321 + 1322 | TAT GAA | 12458-63 | 4 | 0/4 | |
| ΔT1320 | ACA | 12455-7 | 4 | 0/4 | |

[a] Amino acid position of the RSV L ORF (Genbank Accession number M74568). Note that these mutants were constructed in the recombinant wt RSV 6120 backbone (see the Description of FIG. 2 for an explanation).
[b] Genome positions according to the complete unmodified sequence of biologically-derived wt RSV strain A2 (Genbank Accession Number M74568).
[c] Substitution mutation as a positive control for recovery.
[d] site of "530" mutation.
[e] site of "248" mutation.
[f] site of BPIV3 11103V mutation.
[g] site of "1009" mutation.
[h] site of "1030" mutation.

Example 2—Recovery and Sequence Analysis of Recombinant RSVs with Substitutions at Amino Acid 1321 of the L Protein As shown in Table 1, it was not possible to recover codon-deletion mutations at or near the sites of major attenuating point substitution mutations that were previously identified for RSV and are present in current vaccine candidates. Therefore, it was investigated whether it would be possible to identify alternative codons or amino acid assignments that might be recoverable in virus and might provide improved stability. This was investigated with the RSV "1030" mutation (this designation refers to a biological clone from the original mutagenesis experiments and not to a sequence position), which occurs at amino acid position 1321 in the L polymerase protein. The wt assignment at this position is tyrosine (TAT), and the ts, attenuating mutation is asparagine (AAT), which differs by a single nucleotide (underlined). This mutation also can be described as Y1321N, or 1321N (single letter code for the wt and mutant amino acid assignments, to the left and right, respectively). This nomenclature is used throughout this document except where noted, but of necessity is descriptive rather rigidly limiting. This mutation was previously observed to be unstable in a live attenuated RSV vaccine candidate rA2cp248/404/1030/ΔSH that was evaluated in young infants (Karron et al. JID 191:1093-1104, 2005). Note that "rA2" refers to "recombinant RSV strain A2". In the Examples, this prefix is sometimes added to virus names, but in most case is omitted.

In an attempt to stabilize this mutation, the mutant asparagine (AAT) assignment at L amino acid position 1321 was substituted with an alternate codon or alternate amino acid assignment that might be more stable against reversion to an assignment conferring a wt-like phenotype. Substitutions of amino acids also might have other desirable qualities, such as increased or decreased ts or attenuation phenotypes, which might be useful for vaccine development. Therefore, a panel of recombinant RSV was constructed containing the wt tyrosine assignment or each of the other 19 amino acid substitutions at position 1321. This provided a panel of RSV substitution mutants that could be further assessed for stability, attenuation, and growth characteristics desirable for a vaccine candidate.

As shown in Table 2, 19 of the 20 possible amino acid substitutions at position 1321 yielded recoverable virus. The only virus that was not recovered contained a Y1321R substitution: this virus was not recovered in five independent transfections and was thus considered to be nonviable. This probably was not due to an adventitious mutation in the antigenomic cDNA, since construction of each of the mutants involved transferring a 4013-nt fragment of the L gene bearing the region of position 1321 into a preparation of full-length antigenomic cDNA that yielded viable virus with other 1321 amino acid assignments, and it is generally recognized that cloning in bacteria has a low error rate. Furthermore, the L gene of this antigenomic cDNA (representing 43% of the genome) was sequenced completely and confirmed to be correct. Also, two independent antigenomic cDNAs were assayed for recovery, both with negative results. Each viral genome from the 19 viable viruses was completely sequenced from uncloned RT-PCR products to confirm its integrity. For several of the recovered viruses, inserts of one (or in one case three) adenosine residues were discovered (Table 2). Since these were not present in the original cDNA, they represent adventitious mutations acquired during passage, which frequently occur for RNA viruses. In several cases, adenosine residues occurred in the GE signal of the G or N gene, and specifically occurred in the tract of adenosine residues that constitute the end of the GE signal and directs the viral polymerase to produce the mRNA polyA tail during viral gene transcription. In one virus, an insertion of one adenosine residue occurred in the downstream non-translated region of the L gene, and in another virus an insertion of one adenosine occurred in a run of adenosine residues at the end of the leader region. The insertion of additional adenosine residues such as these into GE signals or other non-translated regions during RSV growth in cell culture is not unusual and was considered to be insignificant. These results indicated that many alternative residues could be accommodated at position 1321, some of which yielded viruses that may have characteristics different than those observed for the original biologically-derived RSV 1030 mutant (Y1321N).

TABLE 2

Recovery and sequence analysis of recombinant RSVs with substitutions at amino acid 1321 of the L protein[a]

| Mutation | 1321 codon | Recovery | Adventitious mutations[b] |
|---|---|---|---|
| Y1321[c] | TAT | + | Insertion of a single A residue in a run of A nt at 15019 between the L stop codon and L GE signal |

TABLE 2-continued

Recovery and sequence analysis of recombinant RSVs
with substitutions at amino acid 1321 of the L protein[a]

| Mutation | 1321 codon | Recovery | Adventitious mutations[b] |
|---|---|---|---|
| 1321N[c] | AAT | + | |
| 1321G | GGT | + | |
| 1321A | GCT | + | |
| 1321S | TCT | + | |
| 1321T | ACT | + | |
| 1321C | TCT | + | Insertion of 3 A residues in a run of A nt (nt 5595) in the G GE signal |
| 1321V | GTT | + | |
| 1321L | TTA | + | |
| 1321I | ATT | + | |
| 1321M | ATG | + | |
| 1321P | CCT | + | |
| 1321F | TTT | + | Insertion of a single A nt into a run of A residues at the end of the leader region (nt 44); insertion of a single A residue in a run of A nt (nt 5595) in the G GE signal |
| 1321W | TGG | + | Insertion of an A residue in a run of A nt (nt 2328) in the N GE signal |
| 1321D | GAT | + | |
| 1321E | GAA | + | |
| 1321Q | CAG | + | |
| 1321H | CAT | + | |
| 1321K | AAA | + | |
| 1321R | CGT | No | |

[a]Genome positions according to the complete unmodified sequence of biologically-derived wt RSV strain A2 (Genbank accession number M74568). Note that these mutants were constructed in the recombinant wt RSV 6120 backbone (see the Description of FIG. 2 for an explanation).
[b]GE: gene-end transcription signal.
[c]Y is the wild-type (wt) assignment at position 1321. N is the mutant assignment in the original biologically-derived "1030" virus.

Example 3—Characterization of RSVs with Substitutions at Amino Acid 1321 of the L Protein Each of the mutant viruses that was recovered was assessed for the ability to replicate in vitro at a range of temperatures (32° C.-40° C.) at which wt RSV is permissive for replication in order to identify possible ts phenotypes (Table 3). In addition, the mutants were evaluated for the ability to replicate in the nasal turbinates and lungs of mice, to identify possible attenuation phenotypes (Table 3). The mouse is an extensively used in vivo model for RSV replication that, like humans, has a 37° C. body temperature and thus can be used to evaluate ts mutants. The mouse is not as permissive as the human for RSV replication and thus does not predict the level of replication in humans, but it does provide a means to compare the relative replication efficiencies of RSV mutants. Ten-week old mice were inoculated intranasally with $10^6$ PFU of each the viruses. Four days after infection, the animals were sacrificed and the nasal turbinates and lungs were harvested and processed to quantify virus titer by plaque assay (Table 3). As shown in Table 3, the original Y1321N mutation confers an in vitro shut-off temperature of 38° C. (the shut off temperature ($T_{SH}$) is defined as the lowest restrictive temperature at which the reduction compared to the permissive temperature of 32° C. is 100-fold or greater than that observed for wt RSV at the two temperatures). This is consistent with previous results (Whitehead, et al., J. Virol 73:871-7 (1999)). The results from the mouse study showed that the Y1321N mutation resulted in a log 10 reduction in titer of 1.1 and 0.6 in the lungs and nasal turbinates, respectively, compared to wild-type virus (Table 3, the wild-type virus is called Y1321 in this Table).

Of the 18 other mutant viruses tested, 17 had a shut-off temperature lower than that of wild-type virus (Y1321). In addition, 9 of these mutant viruses (1321D, 1321E, 1321P, 1321K, 1321G, 1321T, 1321C, 1321Q, 1321V) exhibited a substantial degree of temperature sensitivity, with shut-off temperatures of 35-38° C., compared to 38° C. for the original "1030" mutation (Table 3). When evaluated in mice, several viruses were found to be attenuated, relative to the wild-type virus, with a few of these viruses, such as 1321E, 1321P, 1321K, 1321G, exhibiting attenuation similar to or greater than the original RSV 1030 mutant (1321N). Virus 1321D, which was the most ts of the viruses, could not be recovered from the mice and thus likely was over-attenuated. A number of other viruses, such as 1321L, 1321F, 1321W, and 1321H, exhibited only a modest amount of temperature sensitivity and little or no attenuation, and 1321M was neither temperature sensitive nor attenuated, although it did form microplaques at 39° C. and thus may be slightly more attenuated than the wt virus. Comparison of the chemical structures of the amino acids that were associated with attenuation or a lack of attenuation did not reveal any consistent patterns that might have been used to predict the effects of these substitutions (not shown).

TABLE 3

Characterization of the temperature sensitivity and attenuation phenotypes of recombinant RSVs with substitutions at amino acid sequence position 1321 of the L protein

| | Virus titer (PFU per mL) at indicated temperature (° C.)[a] | | | | | | | | Replication in mice[b] | | | |
|---|---|---|---|---|---|---|---|---|---|---|---|---|
| | | | | | | | | | Titer ($\log_{10}$ PFU/g ± SE) | | Mean $\log_{10}$ reduction[c] | |
| Virus | 32 | 35 | 36 | 37 | 38 | 39 | 40 | $T_{SH}$[d] | Nasal turbinates | Lung | Nasal turbinates | Lung |
| Y1321wt | 7.8 | 7.8 | 7.8 | 7.8 | 7.8 | 7.9 | 7.7 | >40 | 4.6 ± 0.1 | 4.2 ± 0.1 | | |
| 1321N[e] | 7.7 | 7.8 | 7.6 | 7.4* | ≤1 | <1 | <1 | 38 | 3.5 ± 0.1[g] | 3.6 ± 0.0[g] | 1.1 | 0.6 |
| 1321D | 6.1* | 3.4 | 3.5 | 3.3 | 3.3 | 3.1 | 3.2 | 35 | n.d.[h] | n.d. | | |
| 1321E | 7.5 | 7.2* | 6.3* | 3.5* | <1 | <1 | <1 | 37 | 1.9 ± 0[g] | 1.7 ± 0.0[g] | 2.7 | 2.5 |
| 1321P | 7.7 | 7.8 | 7.7 | 4.5 | ≤1 | <1 | <1 | 37 | 3.6 ± 0.1[g] | 2.8 ± 0.0[g] | 1.0 | 1.4 |
| 1321K | 7.5 | 7.5 | 7.4 | 7.3* | ≤1 | <1 | <1 | 38 | 4.0 ± 0.1[g] | 2.7 ± 0.2[g] | 0.6 | 1.5 |
| 1321G | 7.5 | 7.4 | 7.3 | 6.9 | ≤1 | <1 | <1 | 38 | 3.7 ± 0.1[g] | 3.5 ± 0.1[g] | 0.9 | 0.7 |
| 1321T | 7.6 | 7.6 | 7.6 | 7.5* | ≤1 | <1 | <1 | 38 | 4.0 ± 0.1[g] | 3.8 ± 0.0 | 0.6 | 0.4 |
| 1321C | 7.9 | 8.0 | 8.0 | 7.8 | ≤1 | <1 | <1 | 38 | 3.9 ± 0.5 | 3.9 ± 0.1 | 0.7 | 0.3 |
| 1321Q | 7.6 | 7.7 | 7.6 | 7.5 | ≤1 | <1 | <1 | 38 | 4.4 ± 0.1 | 3.7 ± 0.1 | 0.2 | 0.5 |

TABLE 3-continued

Characterization of the temperature sensitivity and attenuation phenotypes of recombinant RSVs with substitutions at amino acid sequence position 1321 of the L protein

| | Virus titer (PFU per mL) at indicated temperature (° C.)[a] | | | | | | | $T_{SH}{}^d$ | Replication in mice[b] | | | |
|---|---|---|---|---|---|---|---|---|---|---|---|---|
| | | | | | | | | | Titer ($\log_{10}$ PFU/g ± SE) | | Mean $\log_{10}$ reduction[c] | |
| | | | | | | | | | Nasal turbinates | Lung | Nasal turbinates | Lung |
| Virus | 32 | 35 | 36 | 37 | 38 | 39 | 40 | | | | | |
| 1321V | 7.9 | 7.9 | 7.9 | 7.8* | 4.9# | <1 | <1 | 38 | 4.4 ± 0.1 | 3.9 ± 0.1 | 0.2 | 0.3 |
| 1321A | 7.2 | 7.3 | 7.2 | 7.0 | 6.1* | ≤1 | <1 | 39 | 4.2 ± 0.0 | 3.7 ± 0.1 | 0.4 | 0.5 |
| 1321S | 7.9 | 7.9 | 7.8 | 7.7 | 6.6* | ≤1 | <1 | 39 | 4.2 ± 0.1 | 3.9 ± 0.1 | 0.4 | 0.3 |
| 1321I | 7.5 | 7.5 | 7.5 | 7.4 | 7.1* | 5.1* | <1 | 39 | 4.1 ± 0.2 | 3.8 ± 0.1 | 0.5 | 0.4 |
| 1321L | 7.5 | 7.5 | 7.5 | 7.4 | 7.4 | 7.2* | ≤1 | 40 | 4.4 ± 0.1 | 4.4 ± 0.0 | 0.2 | none |
| 1321F | 7.5 | 7.5 | 7.6 | 7.4 | 7.3* | 6.7# | ≤1 | 40 | 4.3 ± 0.1 | 4.1 ± 0.1 | 0.3 | 0.1 |
| 1321W | 7.7 | 7.7 | 7.6 | 7.7 | 7.5* | 6.1# | ≤1 | 40 | 4.2 ± 0.1 | 4.3 ± 0.1 | 0.4 | none |
| 1321H | 7.9 | 6.9 | 6.9 | 6.9 | 6.7 | 6.1* | ≤1 | 40 | 4.5 ± 0.1 | 4.3 ± 0.0 | 0.1 | none |
| 1321M | 7.8 | 7.9 | 7.9 | 7.8 | 7.7 | 7.1# | 6.3# | >40 | 4.7 ± 0.0 | 4.4 ± 0.1 | none | none |

[a]The ts phenotype for each virus was evaluated by plaque assay on HEp2 cells at the indicated temperatures. *small plaques, #micro plaques. For viruses with the ts phenotype, values indicating the shut-off temperature are marked (bold, underlined). The shut off temperature is defined in footnote d below.
[b]10-week-old mice in groups of five were inoculated intranasally with 10[6] PFU of the indicated virus. Nasal turbinates and lungs were harvested on day 4, and virus titers were determined by plaque assay. SE: Standard error.
[c]Reduction in mean titer compared to 1321Y (wt) virus.
[d]Shut off temperature ($T_{SH}$) is defined as the lowest restrictive temperature at which the reduction compared to 32° C. is 100-fold or greater than that observed for wt RSV at the two temperatures. The ts phenotype is defined as having a shut off temperature of 40° C. or less (bold, underlined).
[e]Original "1030" amino acid assignment.
[g]Statistically significant (P ≤ 0.05, underlined) difference compared to wt 1321Y control virus.
[h]n.d., not detectable.

Example 4—Stability of Codons Encoding Attenuating Amino Acid Residues

Pursuant to identifying a more stable attenuating mutation at position 1321 in the L protein, attention was focused on the amino acid assignments in Table 3 that specified a level of temperature sensitivity and attenuation similar to or exceeding that of the original 1321N mutant. These included the E, P, K, and G mutants. As shown in Table 4, all of the possible codons for these amino acids were examined (using the genetic code as reference) to enumerate all of the possible amino acid coding changes that could be created by all possible single nucleotide substitutions at each of the three codon positions. Note that this is a "paper" exercise in which all of the theoretical coding changes were enumerated. These possible amino acids were then identified as "wild-type-like", or "intermediate", or "attenuated" based on the information on their level of temperature sensitivity and attenuation in Table 3. Specifically, the "wild-type-like" assignments (Y, S, L, F, W, H, and M) were ones that replicated in mice to a level approaching that of the wild type assignment: i.e., the titers in both the nasal turbinates and lungs were reduced ≤0.4 log 10 each and the $T_{SH}$ was ≥39° C. (Table 3). These assignments would not be desirable because mutations that yielded these amino acids would confer substantial loss of attenuation. A second group of residues was considered to be attenuated because these residues were associated with the greatest observed decreases in viral replication. Specifically, residues (N, D, E, P, K, G, and R) either had viral titers that were reduced ≥0.9 log 10 in either the lungs or nasal turbinates, or were non-viable (i.e. the R assignment) and thus would not yield phenotypic reversion (Table 3). The remaining residues (T, C, Q, V, A, and I) were "intermediate", and represented a partial shift towards reversion, but remained partially attenuated. The goal was to identify one or more codons that specified an attenuating amino acid and that could not be changed by any single nucleotide substitution to an amino acid specifying a wild-type-like phenotype, and preferably would have a minimum number of possible changes to an amino acid specifying an intermediate phenotype. As shown in Table 4, a number of the codons that were examined had at least one possible change that would yield a wild-type-like phenotype. However, several codons were identified that could not yield a wild-type-like assignment with a single nucleotide substitution, namely: the E(GAA), E(GAG), K(AAA), and G(GGA) codons. While these examples [E(GAA), E(GAG), K(AAA), and G(GGA)] may represent the most promising examples, other codons also appear to provide superior alternatives to the wt assignment. For example, while the original "1030" mutant assignment of N(AAT or AAC) had three possible substitutions leading to a wt-like assignment, alternatives such as G(GGG, GGT, or GGC) had only one possible substitution each leading to a wt-like assignment.

TABLE 4

Theoretical outcomes of all possible single nucleotide substitutions in all possible codons of selected amino acid assignments[a]

| Amino acid | Codon | Effect of nt point mutation (N to indicated nt) on amino acid assignment | | | | | Number of phenotypic reversions | |
|---|---|---|---|---|---|---|---|---|
| | | Position[d] | T | C | A | G | Intermed | Wt |
| N | AAT[b,c] or AAC[c] | NAY[d] | Y[e] | H[e] | N | D | 2 | 3 |
| | | ANY | I | T | N | S | | |
| | | AAN | N | N | K | K | | |
| P | CCT[c] or CCC[c] | NCY | S | P | T | A | 2 | 3 |
| | | CNY | L | P | H[e] | R | | |
| | | CCN | P | P | P | P | | |
| P | CCA[c] or CCG[c] | NCR[d] | S | P | T | A | 3 | 2 |
| | | CNR | L | P | Q | R | | |
| | | CCN | P | P | P | P | | |
| G | GGG | NGG | W | R | R | G | 2 | 1 |
| | | GNG | V | A | E | G | | |
| | | GGN | G | G | G | G | | |

TABLE 4-continued

Theoretical outcomes of all possible single nucleotide substitutions in all possible codons of selected amino acid assignments[a]

| Amino acid | Codon | Position[d] | Effect of nt point mutation (N to indicated nt) on amino acid assignment | | | | Number of phenotypic reversions | |
|---|---|---|---|---|---|---|---|---|
| | | | T | C | A | G | Intermed | Wt |
| G | GGT[c] or | NGY | C | R | <u>S</u> | G | 3 | 1 |
| | GGC[c] | GNY | V | A | D | G | | |
| | | GGN | G | G | G | G | | |
| K | AAG | NAG | stop | Q | K | E | 2 | 1 |
| | | ANG | <u>M</u> | T | K | R | | |
| | | AAN | N | N | K | K | | |
| E | GAA or | GAR | stop | Q | K | E | 3 | |
| | GAG[c] | GNR | V | A | E | G | | |
| | | GAN | D | D | E | E | | |
| K | AAA | NAA | stop | Q | K | E | 3 | |
| | | ANA | I | T | K | R | | |
| | | AAN | N | N | K | K | | |
| G | GGA | NGA | stop | R | R | G | 2 | |
| | | GNA | V | A | E | G | | |
| | | GGN | G | G | G | G | | |

[a]The first and second columns at the left indicate the amino acid assignment (column 1) and specific codons (column 2) being analyzed. As shown in column 3, each codon is analyzed for substitutions at codon positions 1, 2, and 3 (nucleotide position in the codon where substitution occurs is indicated with N). The next four columns show the amino acid assignments resulting from T, C, A, and G substitutions at this position. Amino acids that confer an intermediate attenuation phenotype are italicized. Ones that confer a wt-like phenotype are in bold and underlined.
[b]AAT: codon present in the rA2cp248/404/1030ΔSH virus that was evaluated in clinical trials (Karron et al, JID 191: 1093-1104, 2005).
[c]These codons yield the same outcomes.
[d]Y denotes C or T; R denotes G or A.
[e]Amino acid conferring an upward shift in shut-off temperature detected in samples from clinical trials (Karron et al, JID 191: 1093-1104, 2005).

Experiments were conducted to assess the stability of these codons during replication in vitro. This involved "temperature stress tests", in which the virus bearing the mutation of interest was passaged multiple times at increasing temperature in order to provide a selective advantage for any revertants that might occur, allowing these revertants to selectively amplify and be detected. The viruses for comparison included the original 1321N(AAT) mutation as well as the 1321E(GAA), 1321K(AAA), 1321G(GGT), 1321G(GGA), and 1321P(CCT) mutations. Only one of the two 1321E codons was evaluated since both had the same predicted outcomes (Table 4). Ten independent aliquots of each virus were serially passaged two times each at 35° C., 36° C., and 37° C., for a total of six passages (FIG. 1). As controls, two independent aliquots of each virus were serially passaged 6 times at the permissive temperature of 32° C. (FIG. 1, dotted lines). Aliquots of each passage level were titrated by plaque assay at 32° C. to detect changes in yield that might be indicative of changes in the ts phenotype, as an indirect assay of attenuation. Titration analysis indicated that all lineages replicated at 36° C. and 37° C. (FIG. 1), with no restriction due to the ts phenotype. This result alone did not provide clear information on the stability of the ts mutations. However, sequence analysis of a 249-nt region of the L gene spanning the "1030" mutation of viruses from passage 6 was performed in order to directly investigate the stability of its mutation (Table 5). For the 1321N(AAT) virus, for example, sub-populations with reversions to wt (Y) were detected in 9 out of 10 lineages (flasks), and one of these had mixed subpopulations encoding N, Y, and H at codon 1321. Reversion to Y, or change to H, also had been observed in isolates from vaccinees in clinical trials that received an experimental vaccine containing the "1030" mutation, and these changes were associated with an upward shift in temperature sensitivity indicative of a partial loss of attenuation (Karron, J. Infect. Dis 191:1093-104, 2005). This showed concordance between our in vitro assay and results from clinical trials in infants and children. In contrast, neither of the two glycine codons, GGT or GGA, had a change at position 1321. Thus, both codons were identified as providing increased stability. However, each contained a second-site mutation at codon S1313 in 50% and 90% of the lineages, respectively, resulting in a change to cysteine. Another tested virus, 1321K(AAA), also had no detectable change at position 1321 (and thus was stabilized), but had the second site mutation S1313C in 90% of the cultures. The other tested mutants, E(GAA) and P(CCT), had changes at position 1321 in some flasks. All of the changes at position 1321 in virus 1321E(GAA) involved changes to valine or alanine (Table 5), which had "intermediate" attenuated phenotypes (Table 3), whereas all of the changes at position 1321 in virus 1321P(CCT) involved changes to leucine, or histidine (Table 5), which had wt-like phenotypes (Table 3). Thus, the 1321E(GAA) assignment was stable against reversion to wt-like assignments, and the 1321P(CTT) was more stable than the wt 1321N(AAT) assignment. However, both the 1321E(GAA) and 1321P(CCT) viruses had the second site mutation S1313C in nearly all of the cultures. For all of the viruses with changes at codon 1313, the change involved an AGC to TGC point mutation (underlined), resulting in a serine-to-cysteine (S1313C) amino acid change. Thus, the "stress test" evaluation provided presumptive evidence of increased genetic stability at position 1321 with the G(GGA), G(GGT), and K(AAA) mutations, and to a lesser extent with the E(GAA) and P(CCT) mutations. However, the presence of the S1313C mutation suggested that it might be a compensatory second-site mutation that could be solely responsible for the ability of the viruses with no change at position 1321 to replicate efficiently at 35-37° C.

TABLE 5

Observed stability of the various codons encoding amino acid 1321 and occurrence of a potential compensatory 1313C mutation of the L protein during passage at restrictive temperatures[a]

| Virus | % cultures with revertants or compensatory mutation[b] | Codon 1321 | | Compensatory mutation at 1313 [wt assignment S(AGC)] | |
|---|---|---|---|---|---|
| | | Revertant codon observed[c] | Amino Acid[d] | Codon observed[c] | Amino acid[d] |
| N (AAT)[e] | 80 | [A/<u>T</u>]AT | N:<u>Y</u> | | |
| | 10 | [A/<u>T</u>/C]AT | N:<u>Y</u>:H | | |
| G (GGA) | 90 | | | [A/<u>T</u>]GC | S:<u>C</u> |
| G (GGT) | 50 | | | [A/<u>T</u>]GC | S:<u>C</u> |
| K (AAA) | 90 | | | [A/<u>T</u>]GC | S:<u>C</u> |
| E (GAA) | 40 | | | <u>T</u>GC | <u>C</u> |
| | 40 | | | [A/<u>T</u>]GC | S:<u>C</u> |
| | 10 | G[A/<u>T</u>]A | E:<u>V</u> | [A/<u>T</u>]GC | S:<u>C</u> |
| | 10 | G[A/<u>T</u>/C]A | E:<u>V</u>:A | [A/<u>T</u>]GC | S:<u>C</u> |
| P (CCT) | 10 | | | [A/<u>T</u>]GC | S:<u>C</u> |
| | 50 | C[C/<u>T</u>]T | P:<u>L</u> | [A/<u>T</u>]GC | S:<u>C</u> |
| | 20 | C[C/<u>A</u>/<u>T</u>]T | P:<u>L</u>:H | [A/<u>T</u>]GC | S:<u>C</u> |
| | 10 | C<u>TT</u> | <u>L</u> | [A/<u>T</u>]GC | S:<u>C</u> |
| | 10 | C[<u>A</u>/<u>T</u>]T | <u>L</u>:<u>H</u> | | |

[a]Ten replicate 25 cm² flasks of HEp-2 cells were infected with the indicated 1321 mutant at an MOI of 0.1 PFU/cell at 35° C. Virus was harvested between 5 and 7 days post-infection, serially passaged once more at 35° C., and twice each at 36° C. and 37° C., for a total of six passages, each by transferring 1 ml (out of a total of 5 ml) of supernatant to a fresh 25 cm² flask of HEp-2 cells. In parallel, two control flasks per mutant were passaged six times at the permissive temperature of 32° C. For each passage, aliquots were frozen for titration. Genotype analysis was done after the 6th passage by sequencing of a 249 nt region of the RSV L gene (RSV nt 12261-12511; Genbank accession number M74568). No mutations were detected in the 32° C. controls (not shown).
[b]% of cultures with detectable revertant mutations at codon 1321and/or compensatory mutations at codon S1313.
[c]Observed codon sequence: mixtures are indicated in bracket. Nt changes are underlined.
[d]Amino acid coding: Colon indicates a mixed population of the specified amino acids. Amino acid changes are underlined.
[e]Codon present in the rA2cp248/404/1030ΔSH virus evaluated in clinical trials (Karron et al, JID 191: 1093-1104 2005).

Studies were carried out to determine whether the S1313C mutation indeed was a compensatory mutation: in other words, to determine whether it reduced the ts and attenuation phenotypes conferred by the attenuating assignments at 1321. To do this, recombinant viruses were constructed in which each assignment (wild-type tyrosine or the substitutions glycine, glutamic acid, and lysine) at position 1321 was combined with either serine (the wt assignment) or cysteine (the proposed compensatory mutation) at codon 1313 (FIG. 2). In the case of glycine at codon 1321, two different codons were evaluated (GGA and GGT). All of these viruses were recovered, amplified, and sequenced in their entirety and were to shown to be free of adventitious mutations with the exception of a single A insert in the downstream end of the noncoding region of the L gene in mutant 1321K(AAA)/1313C, which was deemed inconsequential (not shown).

the sister virus with the wt serine assignment at codon 1313. In addition, each of these viruses replicated in mice with an efficiency that was indistinguishable from that of the wt parent (Table 6). This shows that, in combination with the attenuating 1321G assignment, the 1313C assignment clearly had a compensatory effect, eliminating to a large extent the ts and attenuation phenotypes specified by the 1321G assignment. Similar results were observed when the 1313C assignment was introduced in the context of the 1321E and 1321K mutations: in each case, the $T_{SH}$ was increased by 2° C., compared to the sister virus with the wt serine assignment at codon 1313, and the restriction on replication in mice was largely ablated (Table 6). This showed that the 1313C mutation indeed compensated for, and largely eliminated, the ts and attenuation phenotypes of mutations at position 1321.

TABLE 6

Demonstration that the S1313C mutation in the RSV L protein is a compensatory mutation, and evaluation of viruses in which the S1313 codon has been silently changed from AGC to TCA or in which the 1313 codon has been deleted.

| | Virus titer (PFU per mL) at indicated temperature (° C.)[a] | | | | | | | | | Replication in mice[b] | | | |
|---|---|---|---|---|---|---|---|---|---|---|---|---|---|
| | | | | | | | | | | Titer (log$_{10}$ PFU/g ± SE) | | Mean log$_{10}$ reduction[c] | |
| Virus | 32 | 35 | 36 | 37 | 38 | 39 | 40 | $T_{SH}$[d] | Δ $T_{SH}$[e] | Nasal turbinates | Lung | Nasal turbinates | Lung |
| Y1321/S1313[f] | 7.8 | 7.8 | 7.7 | 7.6 | 7.6 | 7.6 | 7.2 | >40 | | 4.2 ± 0.1 | 4.6 ± 0.1 | | |
| Y1321/1313C[g] | 8.4 | 8.4 | 8.3 | 8.2 | 8.2 | 8.1 | 7.9 | >40 | 0 | 4.4 ± 0.1 | 4.7 ± 0.0 | | |
| 1321G(GGA)/S1313 | 7.7 | 7.7 | 7.6 | 7.1 | <u><1</u> | <1 | <1 | <u>38</u> | | n.d.[i] | n.d.[i] | n.d.[i] | n.d.[i] |
| 1321G(GGA)/1313C[g] | 8.1 | 8.1 | 8.2 | 8.0 | 7.7 | 6.6 | <u><1</u> | <u>40</u> | +2 | 4.2 ± 0.1 | 4.3 ± 0.1 | | 0.3 |
| 1321G (GGT)/S1313 | 7.5 | 7.5 | 7.3 | 6.9 | <u><1</u> | <1 | <1 | <u>38</u> | | 3.6 ± 0.1 | 3.1 ± 0.2*[h] | 0.6 | 1.5 |
| 1321G (GGT)/1313C[g] | 8.3 | 8.2 | 8.1 | 8.1 | 7.8 | 6.4 | <u><1</u> | <u>40</u> | +2 | 4.3 ± 0.2 | 4.5 ± 0.1 | | 0.1 |
| 1321K(AAA)/S1313 | 7.7 | 7.6 | 7.5 | 7.3 | <u><1</u> | <1 | <1 | <u>38</u> | | 3.8 ± 0.1 | 2.8 ± 0.2*[h] | 0.4 | 1.8 |
| 1321K(AAA)/1313C[g] | 8.2 | 8.2 | 8.0 | 8.1 | 7.8 | 7.2 | <u><1</u> | <u>40</u> | +2 | 4.2 ± 0.2 | 4.5 ± 0.1 | | 0.1 |
| 1321E(GAA)/S1313 | 7.6 | 7.4 | 6.3 | <u>3.5</u> | <1 | <1 | <1 | <u>37</u> | | 2.0 ± 0.0*[h] | 1.8 ± 0.1***[h] | 2.2 | 2.8 |
| 1321E(GAA)/1313C[g] | 8.2 | 8.1 | 8.1 | 7.8 | 7.2 | <u><1</u> | <1 | <u>39</u> | +2 | 4.3 ± 0.0 | 4.2 ± 0.1 | | 0.4 |
| 1321K(AAA)/S1313 (TCA) | 8.4 | 8.3 | 8.2 | 7.2 | <u><1</u> | <1 | <1 | <u>38</u> | 0 | nd[i] | nd[i] | | |
| Δ1313☐ | 7.8 | 7.5 | 6.8 | <u><1</u> | <1 | <1 | <1 | <u>37</u> | −3 | 2.5 ± 0.2*[h] | 2.4 ± 0.1***[h] | 1.7 | 2.2 |

[a]The ts phenotype for each virus was evaluated by plaque assay on HEp-2 cells at the indicated temperatures. For viruses with the ts phenotype, values indicating the shut-off temperature are marked (bold, underlined). The shut off temperature is defined in footnote d below.
[b]10-week-old mice in groups of five were inoculated intranasally with 10$^6$ PFU of the indicated virus. Nasal turbinates and lungs were harvested on day 4, and virus titers were determined by plaque assay. The limit of detection was 2 log$_{10}$ PFU per g for nasal turbinates, and 1.7 log$_{10}$ PFU per g for lungs; SE: Standard error.
[c]Reduction in mean titer compared to the wt virus (Y1321/S1313) of the same experiment.
[d]Shut off temperature ($T_{SH}$) is defined as the lowest restrictive temperature at which the reduction compared to 32° C. is 100-fold or greater than that observed for wt RSV at the two temperatures. The ts phenotype is defined as having a shut off temperature of 40° C. or less (bold, underlined).
[e]Δ$T_{SH}$, Difference (° C.) in shutoff temperature between the indicated 1321 mutant bearing the original S1313 assignment versus the same 1321 mutant bearing the 1313C mutation.
[f]Wild-type amino acid assignments at positions 1321 and 1313: thus, this virus is wild-type. Note that all of the viruses in this Table were constructed in the recombinant wt RSV 6120 backbone (see the Description of FIG. 2 for an explanation).
[g]Second site compensatory mutation 1313C.
[h]Statistically significant difference compared to the wt RSV (one way ANOVA, Kruskal-Wallis test with Dunn's post-hoc test, ***P ≤ 0.001, *P ≤ 0.001 underlined).
[i]n.d. = not done.

As shown in Table 6, the Y1321/S1313 virus (i.e., wt assignments at each position) had a $T_{SH}$ of >40° C., consistent with this being a fully wt virus. The introduction of the 1313C assignment into the wt background (Y1321/1313C) did not result in a lower $T_{SH}$, showing that the introduction of the 1313 serine-to-cysteine mutation in the wt background does not affect temperature sensitivity. In addition, evaluation of the attenuation phenotype in mice showed that this virus remained fully wt (Table 6). For both of the glycine codons that were evaluated, combination with the wt S1313 assignment yielded virus with a $T_{SH}$ of 38° C., consistent with the previous results in Table 3; attenuation in mice was confirmed for the codon GGT (Table 6). However, when the 1313C assignment was combined with either glycine codon, the $T_{SH}$ was increased by 2° C., compared to Example 5—Stabilization of the Attenuating Assignment at L Protein Amino Acid Position 1321 and Wild Type Assignment at Position 1313

An additional mutant virus (1321K(AAA)/S1313(TCA)) was engineered to have the serine at position 1313 encoded by the codon TCA, rather than the AGC codon of the wt virus (FIG. 3A). This was done on the premise that the TCA codon would not be as likely to undergo a S1313C mutation since two bases would have to undergo mutation to encode a cysteine residue, rather than one as in the case of the AGC codon. This premise, that increasing the number of nucleotide changes necessary for reversion provides increased stability, had already been validated in this invention by the results of the analysis of various codons at position 1321

(e.g., see Tables 4 and 5). The 1321K(AAA)/S1313(TCA) virus retained the ts phenotype, with a $T_{SH}$ of 38° C. (Table 6) or 39° C. (Table 8). This virus was tested for phenotypic stability in an abbreviated version of the temperature stress test described above. In this test (FIG. 3B), only 4 consecutive passages were performed, namely two passages at 37° C., followed by two passages at 38° C., the latter being a restrictive temperature for the 1321K(AAA)/S1313(TCA) virus. To confirm that this abbreviated assay provided a stringent test of stability, this analysis also included the mutant virus 1321E(GAA)/1313C(TGC), which contained the alternative assignment 1321E(GAA). Sequence analysis showed that 80% of the cultures of the 1321E(GAA)/1313C (TGC) virus exhibited mutations at codon 1321, yielding amino acid substitutions of valine, lysine, and alanine (Table 7), which is consistent with the predictions in Table 4. These substitution assignments were either attenuating (lysine) or intermediate in attenuation phenotype (valine and alanine), and thus showed that the 1321E(GAA) assignment conferred substantial stability against reversion to a wt-like assignment. This also confirmed the effectiveness of the abbreviated stability assay. Importantly, the 1321K(AAA)/ S1313(TCA) virus retained the ts phenotype in this in vitro stress test, as evidenced by the substantially reduced titer compared to the control cultures passaged at the permissive temperature of 32° C. (FIG. 3B). Nucleotide sequencing of the vicinity of the 1321 locus also showed that there was no reversion or mutation at positions 1313 or 1 321 when assessed by nucleotide sequencing (Table 7). This indicated that the 1321 and 1313 codons indeed had both been stabilized.

To investigate this further, the L gene was completely sequenced from a number of the replicate cultures from the temperature stress test shown in FIG. 3B. This identified two amino acid changes in the L protein that were found individually, but not together, in a number of cultures, namely E649D and Q874H. It was possible that these might be compensatory mutations that might mitigate the attenuating effect of the 1321K(AAA)/S1313(TCA) mutation. To evaluate this possibility, viruses were constructed in which each of these mutations was placed in the backbone of wt RSV or the 1321K(AAA)/S1313(TCA) virus. These mutant viruses were recovered, the presence of the appropriate mutations confirmed by sequence analysis, and their ts and attenuation phenotypes determined (Table 8). When placed in the wt RSV backbone, the E649D mutation did not result in a ts phenotype, but it conferred 1.6 and 1.5 log 10 decreases in replication in the upper and lower respiratory tract of mice (Table 8). This identified the E649 mutation as a non-ts attenuating mutation. More importantly, when placed in the 1321K(AAA)/S1313(TCA) backbone, the E649D mutation did not mitigate either the ts or the attenuation phenotype, and thus did not appear to be a compensatory mutation. Similar findings were made with the Q874H mutation. In the wt RSV backbone, the Q874H mutation did not confer the ts phenotype, but it conferred a ≥2.1 and 2.8 log 10 reduction in viral titer in the upper and lower respiratory tract of mice (Table 8). When placed in the 1321K(AAA)/S1313(TCA) background, it caused a slight upward shift in $T_{SH}$, but, more importantly, it did not mitigate the attenuation phenotype.

Thus, it too was not a compensatory mutation. The identification of these two mutations in the 1321K(AAA)/S1313 (TCA) virus during the temperature stress test illustrates the well known potential of RNA viruses to accumulate mutations. However, the finding that neither of these two mutations was compensatory is further evidence of the stability of the 1321K(AAA)/S1313(TCA) backbone. Thus, no potential reversions, mutations, or compensatory changes were detected in the 1321K(AAA)/S1313(TCA) virus following the stress test. Importantly, this identifies a stabilized version of the "1030" mutation. Since the G(GGA), G(GGT), E(GAA), and P(CCT) mutations also exhibited complete stability [G(GGA) and G(GGT)] or improved stability [E(GAA) and P(CCT)] during the stress test summarized in Table 5, but exhibited the S1313C compensatory mutation, it should now be possible to stabilize position 1313 in each of these mutants by the S1313(TCA) assignment.

In addition, the finding that mutations E649D and Q874H are non-ts and attenuating identifies two more attenuating loci that can be used to construct vaccine viruses. Non-ts attenuating mutations are less common than are ts attenuating mutations, and are valuable since the combination of ts and non-ts attenuating mutations has been suggested to confer increased stability compared to ts attenuating mutations alone (Hall et al Virus Res 22:173-184, 1992).

In summary, these experiments identified the methods and means to achieve increased genetic and phenotypic stability, and identified specific alternative codons and amino acids at position 1321 that have increased genetic and phenotypic stability, especially when used in conjunction with a selected codon at position 1313.

TABLE 7

Stability of the assignments at L protein amino acid assignment 1321 and 1313 in the mutant 1321K(AAA)/1313(TCA) during passage at restrictive temperature[a]

| Virus[b] | % cultures with codon 1321 revertants[c] | Codon 1321 codon observed[d] | Amino Acid[e] | Codon 1313 Codon observed[d] | Amino acid[e] |
|---|---|---|---|---|---|
| 1321E(GAA)/ 1313C(TGC)[f] | 50 | G[A/<u>T</u>]A | E:<u>V</u> | TGC | C |
|  | 20 | [G/<u>A</u>]AA | E:<u>K</u> | TGC | C |
|  | 10 | G[A/<u>T/C</u>]A | E:<u>V:A</u> | TGC | C |
| 1321K(AAA)/ S1313(TCA) | 0 |  |  | TCA | S |

[a]Ten replicate 25 cm² flasks of HEp-2 cells were infected with the indicated 831L mutant at an MOI of 0.1 PFU/cell at 37° C. Virus was harvested between 5 and 7 days post-infection, serially passaged again at 37° C., and serially passaged twice at 38° C., for a total of four passages, each by transferring 1 ml (out of a total of 5 ml) of supernatant to a fresh 25 cm² flask of HEp-2 cells. In parallel, two control flasks per mutant were passaged four times at the permissive temperature of 32° C. For each passage, aliquots were frozen for titration and genotype analysis. Genotype analysis was done after the 4th passage by sequencing of a 249 nt region of the RSV L gene (RSV nt 12261-12511; Genbank accession number M74568). No mutations were detected in the 32° C. controls (not shown).
[b]Amino acid assignments of codons 1321 and 1313 are indicated in single-letter code. The codon sequence is shown in parentheses.
[c]% of cultures with detectable revertants.
[d]Observed codon sequence: mixtures are indicated in bracket. Nt changes are underlined.
[e]Amino acid coding: colon indicates a mixed population of the specified amino acids Amino acid changes are underlined.
[f]Control to show that the abbreviated stress test sensitively detects instability.

TABLE 8

Effect of L protein mutations E649 and Q874 on the temperature sensitivity and attenuation phenotypes of wt RSV and the mutant RSV 1321(AAA)/S1313(TCA)

| Virus | Exp #[d] | Virus titer (PFU per mL) at indicated temperature (° C.)[a] | | | | | | | $T_{SH}$[e] | $\Delta T_{SH}$[f] | Replication in mice[b] | | | |
|---|---|---|---|---|---|---|---|---|---|---|---|---|---|---|
| | | | | | | | | | | | Titer (log$_{10}$ PFU/g ± SE) | | Mean log$_{10}$ reduction[c] | |
| | | 32 | 35 | 36 | 37 | 38 | 39 | 40 | | | Nasal turbinates | Lung | Nasal turbinates | Lung |
| rA2 (wt) | 1 | 7.7 | 7.7 | 7.7 | 7.6 | 7.6 | 7.6 | 7.1 | >40 | | 4.0 ± 0.1 (10/10) | 4.5 ± 0.0 (10/10) | | |
| | 2 | 7.7 | 7.7 | 7.6 | 7.6 | 7.5 | 7.6 | 7.4 | >40 | | | | | |
| 1321K(AAA)/S1313 (TCA) | 2 | 8.1 | 8.2 | 8.1 | 8.1 | 7.4[#] | 5.3[#] | 3.4[#] | 39 | | 3.1 ± 0.1 (5/5) | 3.9 ± 0.1 (5/5) | 0.9 | 0.6 |
| 1321K(AAA)/S1313 (TCA) + E649D | 1 | 7.2 | 7.1 | 7.1 | 6.8 | 6.1[#] | ≤1 | <1 | 39 | | 2.8 ± 0.1 (5/5) | 3.0 ± 0.1 (5/5) | 1.2 | 1.5 |
| | 2 | 7.0 | 7.0 | 7.0 | 6.8 | 6.6 | 5.7[#] | ≤1 | 40 | | | | | |
| E649D[g] | 1 | 7.0 | 7.0 | 7.0 | 6.9 | 6.8 | 6.8 | 6.5 | >40 | 1 | 2.4 ± 0.2 (5/5) | 3.0 ± 0.2 (5/5) | 1.6 | 1.5 |
| 1321K(AAA)/S1313 (TCA) + Q874H | 1 | 7.2 | 7.1 | 7.0 | 7.0 | 6.8 | 6.4 | 4.5[#] | 40 | | 2.0 ± 0.1(5/5)[h] | 2.3 ± 0.1 (5/5) | 2.0 | 2.3 |
| | 2 | 6.8 | 6.7 | 6.8 | 6.7 | 6.5 | 6.3 | 5.7[#] | >40 | | | | | |
| Q874H[g] | 1 | 6.4 | 6.6 | 6.4 | 6.3 | 6.4 | 6.2 | 6.0 | >40 | 0-1 | ≤1.9 (0/5)[h] | 1.7 ± 0.0 (1/5)[h] | ≥2.1 | 2.8 |

[a]The ts phenotype for each virus was evaluated by plaque assay on HEp-2 cells at the indicated temperatures. For viruses with a ts phenotype, the shut-off temperatures are marked (bold, underlined). See footnote e for the definition of shut-off temperature. [#]micro plaque phenotype.
[b]5-week-old mice in groups of five (or ten for wt rA2) were inoculated intranasally with 10$^6$ PFU of the indicated virus. Nasal turbinates and lungs were harvested on day 4, and virus titers were determined by plaque assay. The limit of detection was 1.9 log$_{10}$ PFU per g for nasal turbinates, and 1.7 log$_{10}$ PFU per g for lungs; SE: Standard error. All of the data on replication in mice were from the same experiment (expt. #1).
[c]Reduction in mean titer compared to the wt virus (wt rA2).
[d]Shut off temperature experiment number; two independent plaque assay experiments (#1 and #2) were performed to evaluate the ts phenotype.
[e]Shut off temperature ($T_{SH}$) is defined as the lowest restrictive temperature at which the reduction compared to 32° C. is 100-fold or greater than that observed for wt RSV at the two temperatures. The ts phenotype is defined as having a shut off temperature of 40° C. or less (bold, underlined).
[f]$\Delta T_{SH}$, Difference (° C.) in shutoff temperature between a given viral backbone bearing the original E649 or Q874 codon assignment versus the 649D or 874H mutation.
[g]In the wt backbone. Note that the mutants in this Table were constructed in the recombinant wt RSV 6120 backbone (see the Description of FIG. 2 for an explanation).
[h]Statistically significant difference compared to wt RSV (one way ANOVA, Kruskal-Wallis test with Dunn's post-hoc test, P ≤ 0.001, underlined).

Example 6—Deletion of Codon 1313 Yields a Temperature-Sensitive, Attenuated Mutant In evaluating the second-site compensatory effects of the 1313C mutation, another virus was designed in which the 1313 codon was deleted altogether from the wt RSV backbone (thus, in this virus, the assignment at position 1321 remained unchanged as the wt assignment of tyrosine) (FIG. 4A). This was done with little expectation of success, since deletion of a residue is a more drastic change than a substitution and is less likely to result in a viable virus, as is generally known and was already shown (Table 1). The goal in making this deletion was to prevent compensation of the ts attenuating mutation at position 1321. As a first step, however, the mutation was introduced into the wt background with the idea that this approach would be the most likely to yield recoverable virus.

Surprisingly, the virus deletion mutant, Δ1313, could be recovered. More surprisingly, when grown at 32° C., the Δ1313 virus reached titers of about 7.8 log$_{10}$ PFU per ml, similar to that of wt RSV (Table 6). The genome of the recovered Δ1313 virus was sequenced in its entirety, and was to shown to be free of adventitious mutations (not shown). It was surprising to find that the Δ1313 virus was temperature-sensitive, with a $T_{SH}$ of 37° C. (Table 6). This was a surprise because, whereas the serine-to-cysteine amino acid substitution at position 1313 reduced the level of temperature sensitivity, the deletion of codon 1313 had the opposite effect, and increased the level of temperature sensitivity. In addition, the Δ1313 virus showed significantly reduced replication in the upper and lower respiratory tract of mice (Table 6). Compared to wt virus, titers were reduced by about 50-fold in the upper, and 160-fold in the lower respiratory tract (Table 6). This also was an unexpected finding, since the spontaneous mutation at position 1313 had had the opposite effect, namely to increase the ability of virus with an attenuating mutation at 1321 to replicate in the upper and lower respiratory tract of mice. (Also, as shown below, the combination of the Δ1313 mutation with an attenuating mutation at position 1321 or elsewhere increased rather than decreased the ts and attenuation phenotypes, e.g. Table 9.)

The Δ1313 virus was tested for phenotypic stability in an in vitro stress test (FIG. 4B). Replication of the Δ1313 virus was strongly inhibited at increasing temperatures and, by passage 4, titers of all of the 10 independent lineages were at or just above the detection limit. Thus, the Δ1313 virus had a genetically stable temperature sensitive phenotype. Sequence analysis was not performed because the low level of viral replication produced insufficient RNA for analysis.

Taken together, the S1313 deletion had phenotypic consequences that are desirable for live attenuated RSV vaccine candidates. It conferred in vitro temperature sensitivity and in vivo attenuation to wt RSV. At the permissive temperature of 32° C., replication of the Δ1313 virus was indistinguishable from that of wt RSV in a side-by-side comparison (not shown), which is important since efficient growth is necessary for vaccine manufacture. Theoretical chances for genetic reversion usually are much lower for a deletion mutation compared to a point mutation, since a multiple of 3 nt must be inserted to maintain the translational reading frame. Although this can sometimes occur (Table 1), it seems to depend on the sequence context and appears to occur with specific mutations and not with others. The S1313 deletion was phenotypically stable in a temperature stress test, indicating that reversion did not readily occur. These findings are unanticipated and novel for the following reasons: (i) deletion mutations involving one or a few codons are rarely reported because they typically are non-viable or debilitating, (ii) this particular deletion mutation did not reduce replication at 32° C., fulfilling the need for efficient growth for vaccine manufacture, and (iii) the effect of this mutation was to confer temperature-sensitivity and attenuation, in contrast to previous mutations involving codon 1313, which had the opposite effect of decreasing temperature-sensitivity and attenuation.

The Δ1313 deletion mutation is now available to use on its own or in combination with other attenuating mutations to create live-attenuated RSV vaccines that will be phenotypically stable and thus will have increased safety and utility.

Example 7—New Attenuated Viruses Designed with Stabilized Mutations Including Deletion of Codon 1313

Identification of the Δ1313 deletion, and identification of methods to stabilize the "1030" mutation, both of this invention, provided new ways to construct improved vaccine candidate viruses. A number of examples are shown in FIG. 5. Each of these viruses were recovered successfully from cDNA, and their growth properties—important for vaccine manufacture—and temperature senstivity phenotype—an indirect marker of attenuation—were evaluated in vitro.

The first example at the top of FIG. 5 is cps-3 or cp/ΔSH/Δ1313. This virus combined the Δ1313 mutation of this invention with the previously described "cp" mutations and with the previously described ΔSH mutation. The mutations noted as "cp" comprise a set of five amino acid substitutions that were originally identified in a cold-passaged mutant and which specify an attenuation phenotype: V267I in N, E218A and T523I in F, and C319Y and H1690Y in L (Whitehead et al J Virol 72:4467-4471, 1998). The present ΔSH deletion involved nucleotides 4210-4628, and joined the last nucleotide of the M gene-end signal to the first nucleotide of the SH-G intergenic region. However, it is well appreciated by those skilled in the art that the beginning and end of a deletion in non-coding flanking sequence have flexibility in spacing provided the deletion does not affect cis-acting signals of adjacent genes. Thus a gene deletion can, for example, begin and end at various points within noncoding sequence that flanks each gene, and indeed it was previously described SH deletions involving several different beginning and end positions (Bukreyev et al J Virol 71:8973, 1997; Karron et al JID 191:1093-1104, 2005; Whitehead et al J Virol 73:3438-3442, 1999). The SH gene encodes a small hydrophobic surface protein whose function is unclear, but this protein does not appear to be a significant neutralization antigen. This cps-3 virus was readily recovered and, in this particular preparation, replicated in cell culture to a titer of $1.9 \times 10^7$ PFU/ml (FIG. 5). Further analysis showed that this virus has a $T_{SH}$ of 36-37° C. and exhibited a reduction in titer of 2.1 and 2.6 log 10 in the upper and lower respiratory tract, respectively, of mice (Table 9).

The second virus in FIG. 5, 404/Δ1313, combines the Δ1313 deletion with the previously-described "404" mutation in the gene-start signal of the M2 gene (Whitehead et al, J. Virol. 247:232-239, 1998). This vaccine candidate replicated in cell culture to a titer of $3.3 \times 10^6$ PFU/ml in the experiment shown in FIG. 5. Further analysis (Table 9, and data not shown) showed that it has a $T_{SH}$ of 36-37° C. and exhibited a reduction in titer of >2.1 and >2.8 in the upper and lower respiratory tract of mice.

The third virus in FIG. 5, 1321K(AAA)/Δ1313, combines the Δ1313 deletion with the "stabilized" 1030 mutation involving K(AAA) at position 1321, both of this invention. This vaccine candidate replicated in cell culture to a titer of $1.7 \times 10^7$ PFU/ml (FIG. 5) and had a $T_{SH}$ of 36° C. in the experiment shown in Table 9. This virus was subjected to an in vitro stress test consisting of two passages at 34° C., two passages at 35° C., and two passages at 36° C., at which point virus was barely detectable (FIG. 6). The level of virus was insufficient for sequence analysis, but the lack of significant replication was indicative of a lack of significant reversion.

The fourth virus in FIG. 5, 1321G(GGT)/Δ1313, combined the Δ1313 deletion with an alternative "stabilized" 1030 mutation of this invention, namely 1321G(GGT)(see Table 5 for stress test stability data). This virus replicated in cell culture to a titer of $1.5 \times 10^7$ PFU/ml (FIG. 5) and had a $T_{SH}$ of 35° C. in the experiment shown in Table 9.

The fifth virus in FIG. 5, ΔNS2/Δ1313, combined the Δ1313 deletion of this invention with the previously described ΔNS2 deletion (Whitehead et al J Virol 73:3438-3442, 1999; Wright et al JID 193:573-581, 2006)). The NS2 gene encodes an NS2 protein that functions to inhibit the host interferon response (Spann et al J Virol. 79:5353-5362, 2005). This vaccine candidate replicated in cell culture to a titer of $1.1 \times 10^7$ PFU/ml in the experiment shown in FIG. 5. Further analysis (Table 9) showed that it has a $T_{SH}$ of 38° C. and exhibited a reduction in titer of >2.1 and >2.8 in the upper and lower respiratory tract of mice. This virus was subjected to an in vitro stress test consisting of two passages each at 35°, 36°, 37°, 38°, 39°, and 40° C. (FIG. 7). The observation that a substantial level of replication occurred at the restrictive temperatures, namely 38°, 39°, and 40° C., suggested that reversion or compensatory mutations had occurred. Indeed, sequence analysis identified a mutation I1314T in the L protein, which thus was a potential compensatory mutation (FIG. 7).

Studies were carried out to determine whether this 1314T mutation indeed was a compensatory mutation: in other words, whether it reduced the ts phenotype (and accompanying attenuation phenotype) conferred by the deletion of codon 1313. Thus, versions of the Δ1313 virus were compared that contained either the wt isoleucine or mutant threonine at position 1314 (Table 10). In addition, as described above, it was found that the serine at position 1313 had frequently mutated to cysteine. Cysteine, threonine and serine have nucleophilic properties. Thus, it was hypothesized that phenotypic reversion is dependent on the availability of a nucleophilic residue in this region. Therefore, a version of Δ1313 also was constructed that contained the mutant assignment of L(CTG) at codon 1314. Leucine was chosen because it has similar properties to those of the natural assignment isoleucine, and it is therefore unlikely to result in a phenotypic change. The codon CTG was selected because there is no single nucleotide change that can result in a nucleophilic amino acid (S, T, C). The mutations at positions 1313 and 1314 are illustrated in FIG. 8. Also, a parallel set of mutants was made in the ΔNS2/Δ1313 backbone, specifically: ΔNS2/Δ1313 bearing the wt assignment of I1314, and ΔNS2/Δ1313/1314T and ΔNS2/Δ1313/1314L (CTG) bearing the mutant assignments of 1314T or 1314L (Table 10). The ΔNS2/Δ1313/1314T and ΔNS2/Δ1313/1314L(CTG) viruses were sequenced in their entirety and were to shown to be free of adventitious mutations.

As shown in Table 10, wt RSV had a $T_{SH}$ of >40° C., consistent with this being a fully wt virus. The introduction of the Δ1313 mutation into this wt background resulted in a $T_{SH}$ of 37° C. Combination of the 1314T mutation with Δ1313 increased the $T_{SH}$ by 2° C. A similar observation was made when virus bearing the Δ1313 and ΔNS2 deletions was compared to a version containing in addition the 1314T mutation. In this virus, the 1314T mutation increased the $T_{SH}$ by 1° C. This shows that, in combination with the attenuating Δ1313 mutation, the 1314T mutation clearly has a compensatory effect, eliminating to a large extent the ts phenotype specified by the Δ1313 deletion. The introduction of the alternative 1314L(CTG) mutation into either the Δ1313 or ΔNS2/Δ1313 backbones had no effect on the ts phenotypes of either backbone viruses (Table 10). The ΔNS2/Δ1313/1314L(CTG) virus was subjected to a temperature stress test involving 2 passages each at 36°, 37°, 38° C., and 39° C. and once at 40° C. (FIG. 9). The reduction in titer for most of the cultures at the higher temperatures indicated that the virus retained its temperature-sensitivity. Sequence analysis of virus following the second passage at 37° C. confirmed an absence of mutations (not shown). Importantly, this identifies the ΔNS2/Δ1313/1314L(CTG) virus as an attenuated, stabilized vaccine candidate.

In another approach, amino acid I1314 was deleted in both the wt and ΔNS2 backbones, and in additional viruses deletion was made instead of the nearby nucleophilic amino acid T1316 or T1320 (FIG. 8, Table 10). This was done with little expectation of success, since deletion of a residue is a more drastic change than a substitution and is less likely to result in a viable virus, as is generally known and as was shown in Table 1 above.

Surprisingly, the Δ1314 and Δ1316 mutations could be recovered in both viral backbones (i.e., wt and ΔNS2), but the Δ1320 deletion mutant could not be recovered in either backbone. In either backbone, the Δ1316 mutations conferred a slight ts phenotype (40° C. in either backbone), while the Δ1316 mutation conferred a somewhat greater shift (36° C. and 37° C. in the wt and ΔNS2 backbones, respectively)(Table 10). This identified Δ1314 and Δ1316 as two new codon-deletion mutations that could be included in vaccine viruses, and identified the ΔNS2/Δ1316 virus in particular as a candidate attenuated virus.

TABLE 9

Temperature sensitivity and attenuation phenotypes of new vaccine candidate viruses bearing the Δ1313 deletion combined with other mutations.

| | | | | | | | | | | | | Replication in mice[b] | | | |
|---|---|---|---|---|---|---|---|---|---|---|---|---|---|---|---|
| | | Virus titer (PFU per mL) at indicated temperature (° C.)[a] | | | | | | | | | | Titer ($log_{10}$ PFU/g ± SE) | | Mean $log_{10}$ reduction[c] | |
| Virus | Exp #[d] | 32 | 35 | 36 | 37 | 38 | 39 | 40 | $T_{SH}$[e] | $T_{SP}$[f] | Exp #[g] | Nasal turbinates | Lung | Nasal turbinates | Lung |
| rA2 (wt) | 1 | 8.1 | 8.1 | 8.1 | 8.1 | 8.0 | 8.0 | 7.9 | >40 | >40 | 1 | 4.0 ± 0.1 (10/10) | 4.5 ± 0.0 (10/10) | | |
| | 2 | 7.7 | 7.7 | 7.7 | 7.6 | 7.6 | 7.6 | 7.1 | >40 | >40 | 2 | 4.2 ± 0.1 (5/5) | 4.6 ± 0.1 (5/5) | | |
| | 3 | 7.7 | 7.7 | 7.6 | 7.6 | 7.5 | 7.6 | 7.4 | >40 | >40 | | | | | |
| Δ1313 | 1a[h] | 8.3 | 8.0 | 6.6 | ≤1 | <1 | <1 | <1 | 37 | 36 | 2 | 2.5 ± 0.2 (8/10) | 2.4 ± 0.1 (10/10) | 1.7 | 2.2 |
| | 1b[h] | 8.2 | 7.9 | 6.8 | ≤1 | <1 | <1 | <1 | 37 | 36 | | | | | |
| Cps-3: cp/ΔSHΔ/1313[i] | 2 | 6.3 | 5.4 | 2.7 | 2.5 | 2.4 | <1 | <1 | 36 | | 1 | 1.9 ± 0.0 (1/5) | 1.9 ± 0.1 (4/5) | 2.1 | 2.6 |
| | 3 | 6.3 | 5.6 | 5.1 | 3.5 | 2.2 | 2.3 | <1 | 37 | 36 | | | | | |
| ΔNS2/Δ1313[i] | 1 | 7.1 | 6.9 | 6.7 | 6.0 | ≤1 | <1 | <1 | 38 | 37 | 1 | ≤1.9 (0/5) | ≤1.7 (0/5) | >2.1 | >2.8 |
| 404/Δ1313[i] | 2 | 5.4 | 3.7 | 2.2 | <1 | <1 | <1 | <1 | 36 | 36 | 1 | ≤1.9 (0/5) | ≤1.7 (0/5) | >2.1 | >2.8 |
| | 3 | 5.3 | 4.6 | 3.7 | ≤1 | <1 | <1 | <1 | 37 | 36 | | | | | |
| 1321N(AAT)[j] | 1 | 8.1 | 8.0 | 7.9 | 7.1 | ≤1 | <1 | <1 | 38 | | | nd[k] | nd | | |
| 1321N(AAT)/Δ1313 | 1 | 6.2 | ≤1 | <1 | <1 | <1 | <1 | <1 | 35 | | | nd | nd | | |
| 1321K(AAA) | 1 | 7.8 | 7.8 | 7.8 | 7.4 | ≤1 | <1 | <1 | 38 | 37 | nd | nd | | | |
| 1321K(AAA)/Δ1313[i] | 1 | 7.4 | 5.8 | ≤1 | <1 | <1 | <1 | <1 | 36 | 35 | nd | nd | | | |
| 1321G(GGT) | 1 | 7.8 | 7.7 | 7.7 | 7.5 | ≤1 | <1 | <1 | 38 | | nd | nd | | | |
| 1321G(GGT)/Δ1313[i] | 1 | 7.2 | ≤1 | <1 | <1 | <1 | <1 | <1 | 35 | | nd | nd | | | |

[a]The ts phenotype for each virus was evaluated by plaque assay on HEp-2 cells at the indicated temperatures. For viruses with a ts phenotype, the shut-off temperatures are marked (underlined). See footnote e for definition of shut-off temperature.

[b]5-week-old mice in groups of five (or ten for wt rA2) in were inoculated intranasally with $10^6$ PFU of the indicated virus. Nasal turbinates and lungs were harvested on day 4, and virus titers were determined by plaque assay. The limit of detection is 1.9 $log_{10}$ PFU per g for nasal turbinates, and 1.7 $log_{10}$ PFU per g for lungs; SE: Standard error. Values in parentheses are: (number shedding/number infected).

[c]Reduction in mean titer compared to the wt virus (rA2 (wt)) of the same experiment.

[d]Shut off temperature experiment number.

[e]Shut off temperature ($T_{SH}$, underlined) is defined as the lowest restrictive temperature at which the reduction compared to 32° C. is 100-fold or greater than that observed for wt RSV at the two temperatures. The ts phenotype is defined as having a shut off temperature of 40° C. or less.

[f]$T_{SP}$, Small plaque temperature is defined as the lowest restrictive temperature at which the small-plaque phenotype is observed.

[g]Mouse study experiment number.

[h]Two independent dilution series in the same experiment.

[i]Schematic representation shown in FIG. 5.

[j]N(AAT) is the original 1030 mutation, included for comparison. Note that all of the mutants in this Table were constructed in the recombinant wt RSV 6120 backbone (see the Description of FIG. 2 for an explanation).

[k]nd, not determined in this study.

TABLE 10

Analysis of the temperature sensitivity phenotypes of the Δ1313 virus and ΔNS2/Δ1313 virus, each bearing amino acid substitutions or deletions involving L protein amino acid residues 1314, 1316, and 1320

| Virus | Virus titer (PFU per mL) at indicated temperature (° C.)[a] | | | | | | | $T_{SH}$[b] | $T_{SH}$[c] | $\Delta T_{SP}$[d] |
|---|---|---|---|---|---|---|---|---|---|---|
| | 32 | 35 | 36 | 37 | 38 | 39 | 40 | | | |
| Assayed on HEp-2 cells: | | | | | | | | | | |
| wt rA2 | 7.7 | 7.7 | 7.7 | 7.8 | 7.7 | 7.7 | 7.6 | ≥40 | | |
| Δ1313 | 7.8 | 7.6 | 6.7 | <u>≤1</u> | <1 | <1 | <1 | 37 | | 35 |
| Δ1313/1314T | 7.6 | 7.4 | 7.6 | 7.4 | 6.7 | <u>≤1</u> | <1 | 39 | +2 | 37 |
| Δ1313/1314L(CTG) | 7.0 | 6.7 | 6.2 | <u>≤1</u> | <1 | <1 | <1 | 37 | | 36 |
| Δ1314 | 6.9 | 7.0 | 7.0 | 6.9 | 6.7 | 5.4 | <u>≤1</u> | 40 | | 38 |
| Δ1316 | 5.8 | 4.6 | <u>≤1</u> | <1 | <1 | <1 | <1 | 36 | | |
| Assayed on Vero cells: | | | | | | | | | | |
| wt rA2 | 8.0 | 8.0 | 7.9 | 7.9 | 7.8 | 7.6 | 7.5 | ≥40 | | |
| ΔNS2/Δ1313 | 7.1 | 6.9 | 6.6 | 6.3 | 5.1 | <u>≤1</u> | <1 | 39 | | 32 |
| ΔNS2/Δ1313/1314T | 7.1 | 7.1 | 7.0 | 6.9 | 6.7 | 5.9 | <u>4.1</u> | 40 | +1 | 32 |
| ΔNS2/Δ1313/1314L(CTG) | 7.5 | 7.3 | 7.0 | 6.7 | 5.7 | <u>1.7</u> | <1 | 39 | | 37 |
| ΔNS2/Δ1314 | 6.4 | 6.5 | 6.4 | 6.3 | 6.0 | 5.7 | <u>4.4</u> | 40 | | 32 |
| ΔNS2/Δ1316 | 6.8 | 6.1 | 5.4 | <u>3.7</u> | 1.7 | <1 | <1 | 37 | | 32 |

[a]The ts phenotype for each virus was evaluated by plaque assay on HEp-2 cells (top) or Vero cells (bottom) at the indicated temperatures. Vero cells were used for the ΔNS2 viruses because loss of expression of NS2 renders RSV more sensitive to type I interferon, which is not made by Vero cells. Note that all of the mutants in this Table were constructed in the recombinant wt RSV 6120 backbone (see the Description of FIG. 2 for an explanation).
[b]Shut off temperature ($T_{SH}$, underlined) is defined as the lowest restrictive temperature at which the reduction compared to 32° C. is 100-fold or greater than that observed for wt RSV at the two temperatures. The ts phenotype is defined as having a shut off temperature of 40° C. or less.
[c]$\Delta T_{SH}$, Difference (° C.) in shutoff temperature between a specific Δ1313 or ΔNS2/Δ1313 mutant with original I1314 assignment and same Δ1313 or ΔNS2/Δ1313 mutant with the added 1314T mutation.
[d]$T_{SP}$, Small plaque temperature is defined as the lowest restrictive temperature at which the small-plaque phenotype is observed. Temperatures at which small plaques were observed are in bold.

Example 8. Additional New Attenuated Viruses Designed with Stabilized Mutations As already noted, an RSV vaccine candidate called rA2cp248/404/1030ΔSH ("cp248/404/1030ΔSH version 1") was previously designed by reverse genetics and evaluated in RSV-naïve young infants (Karron et al JID 191:1093-1104, 2005). This vaccine virus was well tolerated and was moderately immunogenic in young infants, and was protective against a second vaccine dose (Karron et al JID 191: 1093-1104, 2005). However, in this previous study, analysis of vaccine virus that was shed from vaccinees provided evidence of revertant and mutant virus in one-third of the nasal wash samples. Reversion and mutation involved either the "248" or "1030" mutation, with the incidence being more frequent with the "1030" mutation (Karron et al JID 191:1093-1104, 2005). A second version of the rA2cp248/404/1030ΔSH ("cp248/404/1030ΔSH version 2") cDNA also had been constructed, and virus recovered from this second version is presently being evaluated in clinical studies (ClinicalTrials.gov Identifier NCT00767416). Both versions contained the cp, 248, 404, 1030, and ΔSH mutations, and no differences have been identified between the two versions with regard to virus replication, ts and attenuation phenotypes, or other biological properties. The two versions differed by multiple point mutations throughout the genome that mostly are silent at the amino acid level and are considered inconsequential. These include differences due to naturally occurring variability in wt virus and in some cases due to the presence or absence of added restriction sites or sequence tags. As another difference, the "248" mutation (Q831L) is specified by the codon TTA in cp248/404/1030ΔSH version 2 and CTG in cp248/404/1030ΔSH version 1. Both of these codons readily reverted during an in vitro temperature stress test (Luongo et al Vaccine 27:5667-5676, 2009). Based on available data, the two versions of rA2cp248/404/1030ΔSH appear to have similar properties of growth, temperature sensitivity, and attenuation.

Using the information of this invention, a derivative of cp248/404/1030ΔSH version 2 was constructed in which the "1030" mutation involving 1321N(AAT) was replaced by 1321K(AAA), and the potential second site mutation site S1313(AGC) was replaced by S1313(TCA): this virus is designated cps-1 in FIG. 10 and Table 11. A derivative of cp248/404/1030ΔSH version 2 also was constructed in which the "248" mutation 831L(TTA) was replaced by the codon 831L(TTG), which had been previously shown to confer increased stability (Luongo et al Vaccine 27, 5667-5676, 2009); this virus is called cps-4 in FIG. 10 and Table 11. In addition, a derivative of cp248/404/1030ΔSH version 2 containing 1321K(AAA), S1313(TCA), and 831L(TTG), was constructed, which is called cps-2 and is represented in FIG. 10 and Table 11. Each of these viruses was readily recovered and readily replicated to titers in excess of 10[7] plaque forming units per ml, as summarized in FIG. 10. Also, each of these maintained a ts phenotype, with a shut-off temperature of 35-36° C. (FIG. 10 and Table 11). Each of these maintained an attenuation phenotype in mice (Table 11). These represent additional improved vaccine candidates, and illustrate the potential for making yet additional new combinations.

To directly evaluate the possibility of increased genetic stability of the cps-2 virus, it was subjected to an in vitro stress test in parallel with the cp248/404/1030ΔSH version 1 virus from the study of Karron et al (Karron et al JID 191:1093-1104, 2005), which had exhibited genetic instability. The two viruses were each passaged in ten parallel cultures for two passages each at 33°, 34°, 35°, 36°, and 37° C. Note that for these viruses, temperatures of 36° C. and higher are restrictive. Following the final passage, the genome regions containing the 248 and 1030 mutations were subjected to sequence analysis (Table 12). This analysis showed that the 248 mutation (L protein mutation 831L)

sustained mutations in each virus, reverting to the wt assignment of glutamine in 9 out of 10 cultures in the case of the cp248/404/1030ΔSH version 1 virus and changing to serine in 6 out of 10 cultures in the case of cps-2. It was not surprising to find reversion at this position in both viruses, since it was previously shown that the 248 mutation could not be strongly stabilized (Luongo et al Vaccine 27:5667-5676), and since the stress test involved four passages at restrictive temperatures. Overall, the frequency of reversion at the 248 site was 90% with the cp248/404/1030ΔSH version 1 virus and 60% with cps-2. With regard to the "1030" mutation (L protein amino acid position 1321), the sequence analysis showed that this mutation in the original cp248/404/1030/ΔSH virus (i.e., not stabilized) completely reverted to the wt assignment of tyrosine, while nine of the ten cultures of cps-2 at the restrictive temperatures retained the attenuating assignment of lysine. In the remaining culture, 30% of the culture appeared to have the assignment of arginine. However, virus containing arginine at this position was shown to be nonviable (Table 2). Thus, it may be that this mutant virus was able to replicate in the stress test because this in vitro infection occurred at relatively high MOI, conditions under which it is known that a defective virus can be replicated due to complementation by co-infecting functional virus. Thus, the virus with arginine at this position likely is defective and would not be pathogenic. The assignment at position 1313 at cps-2 also was confirmed to be completely stable during passage, and no other adventitious mutations were observed. In conclusion, therefore, these data showed that (i) the 248 mutation was moderately stabilized, with a reduced frequency of detection of revertants, and (ii) the 1030 mutation was completely stabilized against the generation of viable revertants by the alternative amino acids identified in this invention. This is particularly significant because the 1030 mutation exhibited a several-fold higher level of reversion in the previous clinical trial (Karron et al JID 191:1093-1104, 2005), and thus this invention has succeeded in providing a version of this virus with substantially increased genetic stability.

TABLE 11

Temperature sensitivity and attenuation phenotypes of the previously evaluated vaccine candidate cp248/404/1030ΔSH (version 1) and derivatives containing alternative codons at the "1030" and "248" loci

| Virus | Repl[d] | Virus titer (PFU per mL) at indicated temperature (° C.)[a] | | | | | | | | Replication in mice[b] | | Mean log$_{10}$ reduction[c] | |
|---|---|---|---|---|---|---|---|---|---|---|---|---|---|
| | | | | | | | | | | Titer (log$_{10}$ PFU/g ± SE) | | | |
| | | 32 | 35 | 36 | 37 | 38 | 39 | 40 | T$_{SH}$[e] | T$_{SP}$[f] | Nasal turbinates | Lung | Nasal turbinates | Lung |
| rA2 (wt) | A | 7.7 | 7.7 | 7.7 | 7.6 | 7.6 | 7.6 | 7.1 | >40 | >40 | 4.0 ± 0.1 (10/10) | 4.5 ± 0.0 (10/10) | | |
| | B | 7.7 | 7.7 | 7.6 | 7.6 | 7.5 | 7.6 | 7.4 | >40 | >40 | | | | |
| cp248/404/1030ΔSH (version 1)[g,h] | A | 6.7 | 6.3 | 4.7 | 3.4 | 2.0 | <1 | <1 | 36 | 35 | ≤1.9 (0/10) | ≤1.7 (0/10) | >2.1 | >2.8 |
| cps-1[h] | A | 6.0 | 4.3 | <1 | <1 | <1 | <1 | <1 | 36 | 35 | ≤1.9 (0/5) | ≤1.7 (0/5) | >2.1 | >2.8 |
| | B | 5.9 | 5.3 | 3.7 | 2.2 | <1 | <1 | <1 | 36 | 35 | | | | |
| cps-4[h] | A | 6.2 | 3.4 | 2.0 | <1 | <1 | <1 | <1 | 35 | 36 | ≤1.9 (0/5) | ≤1.7 (0/5) | >2.1 | >2.8 |
| | B | 6.2 | 5.2 | 3.4 | <1 | <1 | <1 | <1 | 36 | 35 | | | | |
| cps-2[h] | A | 5.8 | 4.0 | <1 | <1 | <1 | <1 | <1 | 36 | 35 | ≤1.9 (0/5) | ≤1.7 (0/5) | >2.1 | >2.8 |
| | B | 5.7 | 5.1 | 3.7 | <1 | <1 | <1 | <1 | 36 | 36 | | | | |

[a]The ts phenotype for each virus was evaluated by plaque assay on HEp-2 cells at the indicated temperatures. For viruses with the ts phenotype, the shut-off temperatures are are marked (bold, underlined). See footnote e for the definition of shut-off temperature.

[b]5-week-old mice in groups of five (or ten for wt rA2 and cps5) were inoculated intranasally with 10$^6$ PFU of the indicated virus. Nasal turbinates and lungs were harvested on day 4, and virus titers were determined by plaque assay. The limit of detection is 1.9 log$_{10}$ PFU per g for nasal turbinates, and 1.7 log$_{10}$ PFU per g for lungs; SE: Standard error. The data on replication in mice were from the same experiment.

[c]Reduction in mean titer compared to the wt virus (rA2 (wt)) of the same experiment.

[d]A and B represent duplicate dilution series of the same virus that were examined in parallel in the same experiment. Differences between these replicas (Repl) illustrate the variability that is inherent in these biological experiments.

[e]Shut off temperature (T$_{SH}$, bold, underlined) is defined as the lowest restrictive temperature at which the reduction compared to 32° C. is 100-fold or greater than that observed for wt RSV at the two temperatures. The ts phenotype is defined as having a shut off temperature of 40° C. or less.

[f]T$_{SP}$, Small plaque temperature is defined as the lowest restrictive temperature at which the small-plaque phenotype is observed.

[g]As noted in the text and the legend to FIG. 10, two cp248/404/1030ΔSH cDNAs have been constructed that share the same attenuating mutations (although they differ in the codon of the "248" mutation 831L) and differ by a number of incidental mutations. The virus used here is version 1 that had previously been analyzed in clinical studies by Karron et al (Karron et al JID 191: 1093-1104, 2005). The other mutants in this Table were constructed in the cp248/404/1030ΔSH version 2 backbone.

[h]See FIG. 10 for a diagram of the viral genome, although the version of cp248/404/1030ΔSH that is shown in FIG. 10 is version 2 and thus has CTG rather than TTA as the codon for mutation 831L.

TABLE 12

Stability of L protein codons 831 and 1321 in cp248/404/1030/ΔSH (version 1) and cps-2 during passage at restrictive temperatures[a]

| | | Codon 831L | | | | | Codon 1321 | | | | |
|---|---|---|---|---|---|---|---|---|---|---|---|
| Virus | % cultures with codon revertants[b] | Original codon present in virus | | Revertant | | Reversion (Estimated average % of population ± SD)[e] | Original Codon present in virus | | Revertant | | Reversion rate (Estimated average % of population)[e] |
| | | Codon | Amino acid | codon observed[c] | Amino Acid[d] | | Codon | Amino acid | Codon observed[c] | Amino acid[d] | |
| cp248/404/ 1030ΔSH (version 1)[f] | 70 | CTG | L | C[T/A]G | L:Q | 47 ± 15 | AAT | N | [A/T]AT | Y | 64 ± 22 |
| | 10 | | | CAG | Q | 100 | | | [A/T]AT | Y | 10 |
| | 10 | | | CAG | Q | 100 | | | | | 0 |
| | 10 | | | | | 0 | | | TAT | Y | 100 |
| cps-2 | 40 | TTG | L | TCG | S | 100 | AAA | K[g] | | | 0 |
| | 10 | | | TCG | S | 100 | | | A[A/G]A | R[h] | 30 |
| | 10 | | | T[T/C]G | L:S | 70 | | | | | 0 |

[a]Ten replicate 25 cm² flasks of HEp-2 cells were infected with the indicated virus at an MOI of 0.1 PFU/cell at 33° C. Virus was harvested between 5 and 7 days post-infection, serially passaged again at 33° C., and serially passaged twice at 34° C., 35° C., 36° C., and 37° C., for a total of ten passages, each by transferring 1 ml (out of a total of 5 ml) of supernatant to a fresh 25 cm² flask of HEp-2 cells. In parallel, two control flasks per mutant were passaged ten times at the permissive temperature of 32° C. For each passage, aliquots were frozen for titration and genotype analysis. Genotype analysis was done after the 10th passage from a 2921 bp PCR fragment of the RSV genome (nt 12271-15191; Genbank accession number M74568) which was partially sequenced. No mutations were detected in the 32° C. controls (not shown).
[b]% of cultures with detectable revertants.
[c]Observed codon sequence: mixtures are indicated in bracket. Nt changes are underlined.
[d]Amino acid coding: Colon indicates a mixed population of the specified amino acids. Amino acid changes are underlined.
[e]In cultures with mixed populations, % of subpopulations with reversions were estimated from sequencing chromatograms. Averages and standard deviation SD from cultures with mixed populations are shown.
[f]As noted in the text, two mutant cp248/404/1030ΔSH cDNAs have been constructed that share the same attenuating mutations (except for a silent codon difference at the "248" mutation, as noted elsewhere) and differ by a number of incidental mutations. The virus used here is version 1 that had previously been analyzed in clinical studies by Karron et al (Karron et al JID 191: 1093-1104, 2005).
[g]The stabilized codon 1321K (AAA) was used together with codon S1313(TCA); this latter site was completely stable (not shown).
[h]This assignment yields non-viable virus, as shown in Table 2, and its presence here presumably depends on complementation by non-defective virus during this in vitro infection.

Example 9—Viable Deletion Mutants in the Vicinity of Amino Acid Position 1754

Despite the poor success rate in recovering RSV bearing codon deletions, an attempt was made to design another deletion mutation. In this case, deletion was made of codon 1754 (encoding a serine residue) in the RSV L protein (FIG. 11). Surprisingly, this mutant RSV (1754ΔS) was able to be recovered (Table 13). Further analysis showed that this mutant was not significantly inhibited in plaque formation at elevated temperatures, but had a small plaque phenotype at 38° C. or higher (Table 13). Also, the replication of the Δ1754 virus in mice was somewhat reduced, although the reduction was not significant compared to wt virus (Table 13).

Attempts were then made to recover additional mutations in this region, including single-amino acid mutations (1756ΔA), or bearing a deletion of two contiguous amino acids (1753ΔKS, 1754ΔSS, 1755ΔSA, see Table 13, footnote d for nomenclature), or four contiguous amino acids (1753ΔKSSA, 1754ΔSSAM), or between six and 21 contiguous amino acids (1752Δ6aa, 1749Δ9aa, 1752Δ13aa, 1744Δ14aa, and 1744Δ21aa, FIG. 11 and Table 13). Analysis of the viruses in a ts assay showed that none of these was ts with regard to plaque reduction, but that nine of the twelve mutants had reduced plaque sizes at temperatures ranging from 37° C. to 40° C. (indicated in bold in Table 13). When evaluated for replication in the upper and lower respiratory tract of mice, all of the mutants replicated to titers that were lower than those of wt RSV, and for seven of the viruses the reduction compared to wt RSV was significant. Thus, this series of mutations provides a range of values with regard to the magnitude of attenuation, and the level of attenuation of a recombinant RSV vaccine can thus be adjusted by inclusion of a mutation in this region with a lesser or greater attenuating effect, as desired.

TABLE 13

Temperature sensitivity and attenuation phenotypes of RSV bearing short amino acid deletions in the vicinity of amino acid sequence positions 1744-1764 in the L protein

| | Virus titer (PFU per mL) at indicated temperature (° C.)[a] | | | | | | | | | Replication in mice[b] | | Mean log₁₀ reduction[c] | |
|---|---|---|---|---|---|---|---|---|---|---|---|---|---|
| | | | | | | | | | | Titer (log₁₀ PFU/g ± SE) | | | |
| | | | | | | | | | | Nasal | | Nasal | |
| Virus[d] | 32 | 35 | 36 | 37 | 38 | 39 | 40 | $T_{SH}$[e] | $T_{SP}$[f] | turbinates | Lung | turbinates | Lung |
| Wt | 8.2 | 8.1 | 8.1 | 8.2 | 8.1 | 8.0 | 7.8 | >40 | >40 | 3.4 ± 01 | 3.4 ± 0.1 | | |
| 1754ΔS | 7.2 | 7.3 | 7.3 | 7.2 | 7.3 | 7.0 | 6.9 | >40 | 38 | 2.2 ± 0.3 | 3.2 ± 0.2 | 1.2 | 0.2 |
| 1756ΔA | 7.5 | 7.3 | 7.5 | 7.5 | 7.3 | 7.4 | 7.2 | >40 | 39 | 2.6 ± 0.2 | 3.3 ± 0.2 | 0.7 | 0.1 |
| 1753ΔKS | 6.5 | 6.6 | 6.6 | 6.5 | 6.4 | 6.2 | 6.0 | >40 | 39 | 1.9 ± 0.2***[g] | 2.5 ± 0.5 | 1.5 | 0.9 |
| 1754ΔSS | 6.2 | 6.3 | 6.2 | 6.3 | 5.9 | 5.8 | 5.3 | >40 | 37 | 2.0 ± 0.3**[g] | 2.9 ± 0.1 | 1.4 | 0.5 |
| 1755ΔSA | 6.4 | 6.2 | 6.2 | 6.1 | 6.1 | 6.0 | 5.6 | >40 | 39 | 1.9 ± 0.2***[g] | 2.7 ± 0.2*[g] | 1.5 | 0.7 |

TABLE 13-continued

Temperature sensitivity and attenuation phenotypes of RSV bearing short amino acid deletions in the vicinity of amino acid sequence positions 1744-1764 in the L protein

| Virus[d] | Virus titer (PFU per mL) at indicated temperature (° C.)[a] | | | | | | | $T_{SH}$[e] | $T_{SP}$[f] | Replication in mice[b] | | Mean $\log_{10}$ reduction[c] | |
|---|---|---|---|---|---|---|---|---|---|---|---|---|---|
| | | | | | | | | | | Titer ($\log_{10}$ PFU/g ± SE) | | | |
| | | | | | | | | | | Nasal turbinates | Lung | Nasal turbinates | Lung |
| | 32 | 35 | 36 | 37 | 38 | 39 | 40 | | | | | | |
| 1753ΔKSSA | 6.8 | 6.9 | 6.7 | 6.7 | 6.7 | 6.6 | 6.3 | >40 | 39 | 2.5 ± 0.2 | 3.3 ± 0.1 | 0.9 | 0.1 |
| 1754ΔSSAM | 6.4 | 6.2 | 6.2 | 6.2 | 5.9 | 5.7 | 5.1 | >40 | 37 | 1.5 ± 0.3***[g] | 3.2 ± 0.2 | 1.9 | 0.2 |
| 1752Δ6aa | 6.6 | 6.6 | 6.6 | 6.7 | 6.6 | 6.4 | 6.2 | >40 | 39 | 2.4 ± 0.1 | 3.0 ± 0.1 | 1.0 | 0.4 |
| 1749Δ9aa | 7.7 | 7.6 | 7.6 | 7.6 | 7.6 | 7.5 | 7.3 | >40 | >40 | 2.0 ± 0.3**[g] | 3.4 ± 0.2 | 1.4 | |
| 1752Δ13aa | 6.9 | 6.8 | 6.9 | 6.7 | 6.7 | 6.5 | 6.2 | >40 | >40 | 1.6 ± 0.4**[g] | 2.5 ± 0.1**[g] | 1.8 | 0.9 |
| 1744Δ14aa | 7.4 | 7.5 | 7.4 | 7.5 | 7.3 | 7.3 | 7.1 | >40 | >40 | 2.6 ± 0.1 | 3.2 ± 0.1 | 0.8 | 0.2 |
| 1744Δ21aa | 6.7 | 6.7 | 6.7 | 6.7 | 6.6 | 6.4 | 6.3 | >40 | 39 | 1.7 ± 0.3***[g] | 2.0 ± 0.3***[g] | 1.7 | 1.4 |

[a]The ts phenotype for each virus was evaluated by plaque assay on HEp-2 cells at the indicated temperatures.
[b]10-week-old mice in groups of five were inoculated intranasally with $10^6$ PFU of the indicated virus. Nasal turbinates and lungs were harvested on day 4, and virus titers were determined by plaque assay. The limit of detection is 2 $\log_{10}$ PFU per g for nasal turbinates, and 1.7 $\log_{10}$ PFU per g for lungs; SE: Standard error.
[c]Reduction in mean titer compared to the wt virus (rA2) of the same experiment.
[d]Viruses are named by the amino acid residue in the L protein that was deleted. Viruses that involve deletion of 2-4 residues are named using the L protein amino acid position of the first residue that is deleted, followed by the Δ symbol, followed by the specific contiguous residues that were deleted (e.g., 1754ΔSSAM involves deletion of residues 1754-1757, which have the identities SSAM). For deletions larger than 4 residues, the number of contiguous deleted residues is indicated (e.g., 1752Δ13aa involves a deletion of 13 residues beginning with 1752 and ending 1764). All of the mutants in this Table were constructed in the recombinant wt RSV 6120 backbone (see the Description of FIG. 2 for an explanation).
[e]Shut off temperature ($T_{SH}$) is defined as the lowest restrictive temperature at which the reduction compared to 32° C. is 100-fold or greater than that observed for wt RSV at the two temperatures. The ts phenotype is defined as having a shut off temperature of 40° C. or less. None of these viruses were ts.
[f]$T_{SP}$, Small plaque temperature is defined as the lowest restrictive temperature at which the small-plaque phenotype was observed. Temperatures giving small plaques are indicated in bold.
[g]Statistically significant difference compared to the wt control virus (one way ANOVA, Kruskal-Wallis test with Dunn's post-hoc test, ***P ≤ 0.001, *P ≤ 0.001 underlined).

Example 10—Evaluation of the Attenuation Phenotypes of New Vaccine Candidates in Experimental Animals The level of attenuation is a critical parameter for a vaccine. In the case of RSV, it is generally recognized that the level of disease or reactogenicity is related to the level of viral replication (Collins and Melero Virus Res 2011, 162:80-99). It was therefore sought to evaluate the level of replication in experimental animals of selected vaccine candidates bearing deletion mutations of this invention. As noted, the mouse model is commonly used to evaluate the replication of RSV variants. However, preliminary studies indicated that the cp248/404/1030ΔSH version 2 virus replicated sporadically and at very low levels in mice due to its high level of attenuation (data not shown). This was true even in mice with genetic immunodeficiencies, including SCID (severe combined immunodeficiency), SCID beige, and nude mice (not shown). In these immunodeficient strains, wt RSV replicates to a higher level and for a longer period of time compared to non-immunodeficient mice (results not shown, and Zhou et al. Med. Microbiol. Immunol., 2008 197:345-51), and it was hoped that this increased permissiveness in the immunodeficient strains would provide a higher degree of sensitivity to highly attenuated viruses. However, this was not the case.

Therefore, selected viruses were evaluated in juvenile chimpanzees, which among experimental animals evaluated to date is the most permissive for RSV replication and which has the same body temperature as humans, which is critical for evaluation of viruses with a temperature-sensitive phenotype. It was confirmed that the animals were RSV-seronegative (except for one animal, A9A011, as noted below). Animals were infected by combined intranasal and intratracheal inoculations of $10^6$ PFU per site, and virus shedding in the respiratory tract was evaluated by taking nasal washes daily for 12 days post-infection, bronchioalveolar lavages (BAL) on days 2, 4, 6, and 8, and tracheal lavages on day 10 and 12. Virus titers were determined by plaque assay on Vero cells at 32° C. There were two or three animals in each group, depending on the virus (Tables 14 and 15): unfortunately, one drawback of the chimpanzee model is the limited number of available animals. Three viruses were evaluated: cp248/404/1030ΔSH version 2 (which served as a comparator, since cp248/404/1030ΔSH version 1 was well-tolerated in 1- to 2-month old infants, Karron et al, JID 191:1093-1104, 2005), cps2 (i.e., a virus with a complement of mutations similar to those of cp248/404/1030ΔSH version 2, but with the 1030 mutation in particular designed for increased stability by the methods of this invention, see FIG. 10), and ΔNS2/Δ1313/1314L(CTG) (which also contains stabilized mutations of this invention, see FIG. 9). The nasal wash data are presented in Table 14, and the BAL and tracheal lavage data are presented in Table 15. This showed that cp248/404/1030ΔSH version 2 replicated at a low level over 8-9 days, with virus being detected primarily in the nasal washes. This is consistent with cp248/404/1030ΔSH version 2 being a highly attenuated virus, based on our previous analysis of multiple viruses in the chimpanzee model (Whitehead et al J Virol 1998, 72:4467-4471; Whitehead et al J Virol 1999, 73:3438-3442; Teng et al J Virol 2000, 74:9317-9321). Importantly, the cps-2 and ΔNS2/Δ1313/1324L viruses also were highly attenuated, comparable to cp248/404/1030ΔSH version 2. Note that one of the three animals (animal A9A011) in the group inoculated with the last virus was found to have pre-existing antibodies to RSV, and no vaccine virus shedding was observed, presumably due to inhibition. This animal was excluded from analysis. Importantly, these findings indicate that the cps-2 and ΔNS2/Δ1313/1324L viruses are suitable to be manufactured as clinical trial material for evaluation as candidate RSV vaccines.

TABLE 14

Viral Titers of Nasal Wash Samples from Chimpanzees Inoculated with the RSV Vaccine Candidates cp248/404/1030ΔSH version 2 (abbreviated as "Version 2"), cps-2, or ΔNS2/Δ1313/1314L[a]

| RSV Vaccine candidate | Chimp ID | NW virus titer ($log_{10}$PFU/mL) on indicated days[b] 1 | 2 | 3 | 4 | 5 | 6 | 7 | 8 | 9 | 10 | 12 | Duration of Shedding[c] | Peak virus titer | Sum of daily titers[d] |
|---|---|---|---|---|---|---|---|---|---|---|---|---|---|---|---|
| Version 2 | A8A007 | — | 1.5 | — | 1.8 | — | 1.8 | 1.8 | 2.6 | 1.5 | 1.0 | — | 9 | 2.6 | 15.5 |
| | A8A008 | — | 1.9 | 1.9 | 2.4 | 2.7 | 2.8 | 2.6 | 2.9 | 2.4 | — | — | 8 | 2.9 | 22.5 |
| | Mean: | | | | | | | | | | | | 8.5 | 2.7 | 19.0 |
| cps-2 | A8A009 | — | 1.0 | 2.3 | — | — | 2.2 | 2.0 | 2.8 | 2.3 | 1.0 | — | 9 | 2.8 | 17.2 |
| | A9A002 | — | — | 1.5 | 2.2 | 3.3 | 2.8 | 3.3 | 3.3 | 1.7 | 1.5 | — | 8 | 3.3 | 22.4 |
| | 4X0533 | — | — | 1.0 | 2.2 | 3.7 | 2.4 | 4.6 | 2.6 | 1.6 | 1.0 | — | 8 | 4.6 | 21.9 |
| | Mean: | | | | | | | | | | | | 8.3 | 3.6 | 20.5 |
| ΔNS2/Δ1313/1314L | A5A006 | — | 1.0 | 1.0 | 2.3 | 2.0 | 1.8 | 2.0 | 1.8 | — | — | — | 7 | 2.3 | 15.3 |
| | A6A014 | — | — | — | 1.0 | 1.9 | 1.3 | 1.7 | 2.0 | — | — | — | 5 | 2.0 | 12.8 |
| | A9A011[e] | — | — | — | — | — | — | — | — | — | — | — | [0] | [1.0] | [8.7] |
| | Mean: | | | | | | | | | | | | 6.0 | 2.1 | 14.1 |

[a]Chimpanzees were inoculated by the combined intranasal and intratracheal routes with $10^6$ PFU of the indicated virus in a 1 mL inoculum per site (total dose = $2 \times 10^6$ PFU per animal).
[b]Nasal wash was performed with 3 mL of Lactated Ringer's solution per nostril. Virus titrations were performed on Vero cells at 32° C. The lower limit of detection was 1.0 $log_{10}$ PFU/mL of nasal wash solution. Samples with no detectable virus are represented as "—". Peak titers for each animal are underlined.
[c]The period of days from the first to the last day on which virus was detected, including negative days (if any) in between.
[d]The sum of daily titers is used as an estimate for the magnitude of shedding (area under the curve). A value of 0.7 was used for samples with no detectable virus.
[e]Chimpanzee A9A011 had a pre-existing low RSV neutralizing antibody titer. Results from this animal were not used for calculations of mean values.

TABLE 15

Viral Titers of Bronchoalveolar and Tracheal Lavage Samples from Chimpanzees Inoculated with the RSV Vaccine Candidates cp248/404/1030ΔSH version 2 (abbreviated as "Version 2"), cps-2, or ΔNS2/Δ1313/1314L[a]

| RSV Vaccine candidate | Chimp ID | Bronchoalvcolar/Tracheal Lavage virus titer ($log_{10}$ PFU/mL) on indicated days[b] 2 | 4 | 6 | 8 | 10 | 12 | Duration of Shedding[c] | Peak virus titer | Sum of daily titers[d] |
|---|---|---|---|---|---|---|---|---|---|---|
| Version 2 | A8A007 | 2.7 | — | — | — | — | — | 1 | 2.7 | 6.2 |
| | A8A008 | — | — | — | — | — | — | 0 | 1.0 | 4.2 |
| | Mean: | | | | | | | 0.5 | 1.8 | 5.2 |
| cps-2 | A8A009 | — | — | — | — | — | — | 0 | 1.0 | 4.2 |
| | A9A002 | — | 1.9 | 3.7 | — | — | — | 3 | 3.7 | 8.4 |
| | 4X0533 | — | 1.0 | — | 1.6 | — | — | 5 | 1.6 | 5.4 |
| | Mean: | | | | | | | 4.0 | 2.1 | 6.0 |
| ΔNS2/Δ1313/1314L | A5A006 | 1.8 | 2.9 | 2.3 | — | — | — | 5 | 2.9 | 9.1 |
| | A6A014 | 1.7 | 3.3 | 2.9 | 2.8 | — | — | 7 | 3.3 | 12.1 |
| | A9A011[e] | — | — | — | — | — | — | [0] | [1.0] | [4.2] |
| | Mean: | | | | | | | 6.0 | 3.1 | 10.6 |

[a]Chimpanzees were inoculated by the combined intranasal and intratracheal routes with $10^6$ PFU of the indicated virus in a 1 mL inoculum per site (total dose = $2 \times 10^6$ PFU per animal).
[b]On days 2, 4, 6, and 8, bronchoalveolar lavage was performed with 6 mL of PBS; on days 10 and 12, tracheal lavage was done using 3 mL of PBS per animal. Virus titrations were performed on Vero cells at 32° C. The lower limit of detection was 1.0 $log_{10}$ PFU/mL of lavage solution. Samples with no detectable virus are represented as "—". Peak titers for each animal are underlined.
[c]The period of days from the first to the last day on which virus was detected, including negative days (if any) in between.
[d]The sum of daily titers is used as an estimate for the magnitude of shedding (area under the curve). A value of 0.7 was used for samples with no detectable virus.
[e]Chimpanzee A9A011 had a pre-existing low RSV neutralizing antibody titer. Results from this animal were not used for calculations of mean values.

General Methods

The following methods were used in the experiments described in the prior examples unless otherwise specified. These methods, in some cases, describe only one of a variety of ways by which experiments similar to those described above could be carried out, such alternative methods would be apparent to those of ordinary skill in the art.

Cells.

HEp-2 cells (ATCC CCL23) were maintained in Opti-MEM I (Gibco-Invitrogen, Carlsbad, Calif.) supplemented with 5% fetal bovine serum (FBS) (HyClone, Logan, Utah) and 1 mM L-glutamine (Gibco-Invitrogen). BSR T7/5 cells are baby hamster kidney 21 (BHK-21) cells that constitutively express T7 RNA polymerase (Buchholz, et al., J. Virol 73:251-9 (1999)). These cells are maintained in Glasgow minimal essential medium (GMEM) (Gibco-Invitrogen) supplemented with 2 mM L-glutamine, 2% MEM amino acids (Gibco-Invitrogen), and 10% FBS. Every other passage, the media was supplemented with 2% geneticin (Gibco-Invitrogen) to select for cells that retain the T7 polymerase construct.

Virus Growth and Titration.

RSV strains were propagated in HEp-2 cells at 32° C. in media containing 2% FBS, 250 Units/mL of penicillin and 250 μg/mL of streptomycin (Gibco-Invitrogen). Virus stocks were generated by scraping infected cells into media followed by three rounds of freeze-thawing of cell pellets or by vortexing, clarification of the supernatant by centrifugation, and addition of 10×SPG (2.18 M sucrose, 0.038 M $KH_2PO_4$, 0.072 M $K_2HPO_4$, 0.06 M L-glutamine at pH 7.1) to a final concentration of 1×. Virus aliquots were snap frozen and stored at −80° C. Virus titers were determined by plaque assay on HEp-2 or Vero cells under 0.8% methylcellulose overlay. After 5-day incubation at 32° C., plates were fixed with 80% cold methanol, and plaques were visualized by immunostaining with a cocktail of three HRSV specific monoclonal antibodies (Murphy, et al., Vaccine 8:497-502 (1990)).

Construction of Recombinant RSV Mutants.

The recombinant RSV mutants were constructed using a reverse genetics system based on strain A2 (Collins, P. L., et al., Proc Natl Acad Sci USA 92:11563-7 (1995)). The full-length RSV antigenome cDNA was modified previously by deleting a 112-nt region from the downstream noncoding region of the SH gene and silently modifying the last few codons of the SH open reading frame (ORF), resulting in antigenome cDNA D46/6120. These changes were made to improve stability of the cDNA during growth in *E. coli* and had no effect on the efficiency of virus replication in vitro or in mice (Bukreyev, et al., J. Virol 75:12128-40 (2001)).

Although the D46/6120 cDNA contains a deletion, for simplicity the numbering of sequence positions in the present manuscript is based on the complete sequence of biologically-derived strain A2 (Genbank accession number M74568).

Mutant cDNAs were constructed by well known methods using restriction enzymes to subclone fragments for manipulation, which were then replaced into the original or another mutant backbone. For example, a set of full-length cDNAs representing amino acid assignments N, K, or G for codon 1321 of the RSV L protein (nt 12,458-60) was generated, as well as a full-length cDNA containing a deletion near position 1321 (described above). A 4267 bp fragment containing the 3' end of the L gene and trailer region (restriction site XbaI to trailer end, RSV A2 nt 11,210 to 15,222; Genbank accession number M74568) was subcloned into pBluescript, using the XbaI site contained in the RSV L gene and an FspI restriction site in the antigenome plasmid, 254 bp downstream of the RSV trailer end. Small deletions and the targeted mutations of codon 1321 and codon 1313 were introduced in a by site directed mutaganesis using the QuikChange mutagenesis kit (Stratagene) as recommended by the supplier. The sequence of a 3,195 bp fragment was confirmed, and it was inserted into the RSV D46/6120 antigenome cDNA plasmid, using the PmlI restriction site located in the L gene (nt 12,254; Genbank accession number M74568), and an MluI site present in the plasmid, 225 bp downstream of the RSV trailer end. Other restriction sites in L or elsewhere also were used, such as XbaI and SalI sites. This methodology is well known to one skilled in the arts, and one can readily identify various combinations of enzymes and fragments that can be used to create desired constructs.

Generation of Recombinant RSV Viruses from cDNA.

BSR T7/5 cells were grown to 95% confluency in 6-well plates. Before transfection, cells were washed twice with GMEM containing 3% FBS, 1 mM L-glutamine, and 2% MEM amino acids prior to the addition of 2 ml of media per well. Cells were transfected using Lipofectamine 2000 and a plasmid mixture containing 5 µg of full-length plasmid, 2 µg each of pTM1-N and pTM1-P, and 1 µg each of pTM1-M2-1 and pTM1-L (J. Virol 73:251-9 and Proc. Natl. Acad. Sci. 92:11563-7). Transfected cells were incubated overnight at 37° C. To increase the frequency of virus recovery, some plates were then heat-shocked at 43° C., 3% $CO_2$ for 3 hours (Witko, S. E., et al., J. Virol. Methods 135:91-101 (2006)). All plates were incubated at 32° C. for at least 24 h. The BSR T7/5 cells were harvested by scraping into media, added to subconfluent monolayers of HEp-2 cells, and incubated at 32° C. Virus was harvested between 11 and 14 days post-transfection and titers were determined by plaque assay. Viruses were passaged twice prior to the isolation of RNA from infected cells and the complete sequence of each viral genome was determined from infected-cell RNA by RT-PCR and direct sequence analysis. The only sequences that were not directly confirmed for each genome were the positions of the outer-most primers, namely nt 1-29 and 15,191-15,222.

Evaluation of the Ts Phenotype.

The ts phenotype for each of the rRSV viruses was evaluated by efficiency of plaque formation at 32°, 35°, 36°, 37°, 38°, 39°, and 40° C. Plaque assays were done on HEp-2 cells, in duplicate, and incubated in sealed caskets at various temperatures in temperature controlled waterbaths as previously described (Crowe, J. E., Jr., et al., Vaccine 11:1395-404 (1993)).

Evaluation of the Attenuation Phenotype.

Virus replication was evaluated in the upper and lower respiratory tracts of mice as described (Whitehead, et al., Virology 247:232-9 (1998)). Briefly, 10-week-old female BALB/c mice in groups of five were inoculated intranasally under methoxyflurane anesthesia on day 0 with $10^6$ PFU of rRSV. On day 4, mice were sacrificed by carbon dioxide inhalation. Nasal turbinates and lung tissue were harvested and homogenized separately in L-15 medium containing 1×SPG, 2% L-glutamine, 0.06 mg/ml ciprofloxacin, 0.06 mg/ml clindamycin phosphate, 0.05 mg/ml gentamycin, and 0.0025 mg/ml amphotericin B. Virus titers were determined in duplicate on HEp-2 cells incubated at 32° C.

RSV A2 sequence (Genbank accession number M74568)
(SEQ ID NO: 48)

acgcgaaaaaatgcgtacaacaaacttgcataaaccaaaaaaatggggca aataagaatttgataagtaccacttaaatttaactcccaggttagagatg ggcagcaattcattgagtatgataaaagttagattacaaaatagtagaca atgatgaagtagcattgttaaaaataacatgctatactgataaattaata catttaactaacgctaggctaaggcagtgatacatacaatcaaattgaat ggcattgtgatgtgcatgttattacaagtagtgatatttgccctaataat aatattgtagtaaaatccaatttcacaacaatgccagtactacaaaatgg aggttatatatgggaaatgatggaattaacacattgctctcaacctaatg gtctactagatgacaattgtgaaattaaattctccaaaaaactaagtgat tcaacaatgaccaattatatgaatcaattatctgaattacttggatttga tcttaatccataaattataattaatatcaactagcaaatcaatgtcacta acaccattagttaatataaaacttaacagaagacaaaaatggggcaaata aatcaattcagccaacccaaccatggacacaacccacaatgataatacac cacaaagactgatgatcacagacatgagaccgagtcacttgagaccataa taacatcactaaccagagacatcataacacacaaatttatatacttgata aatcatgaatgcatagtgagaaaacttgatgaaaaacaggccacatttac attcctggtcaactatgaaatgaaactattacacaaagtaggaagcacta aatataaaaatatactgaatacaacacaaaatatggcactaccctatgc caatattcatcaatcatgatgggacttagaatgcattggcattaagccta caaagcatactcccataatatacaagtatgatctcaatccataaatttca acacaatattcacacaatctaaaacaacaactctatgcataactatactc catagtccagatggagcctgaaaattatagtaatttaaaattaaggagag atataagatagaagatggggcaaatacaaagatggctcttagcaaagtca agttgaatgatacactcaacaaagatcaacactgtcatccagcaaataca ccatccaacggagcacaggagatagtattgatactcctaattatgatgtg cagaaacacatcaataagttatgtggcatgttattaatcacagaagatgc taatcataaattcactgggttaataggtatgttatatgcgatgtctaggt taggaagagaagacaccataaaaatactcagagatgcgggatatcatgta aaagcaaatggagtagatgtaacaacacatcgtcaagacattaatggaaa agaaatgaaatttgaagtgttaacattggcaagcttaacaactgaaattc aaatcaacattgagatagaatctagaaaatcctacaaaaaaatgctaaaa -continued gaaatgggagaggtagctccagaatacaggcatgactctcctgattgtgg gatgataatattatgtatagcagcattagtaataactaaattagcagcag gggacagatctggtcttacagccgtgattaggagagctaataatgtccta aaaaatgaaatgaaacgttacaaaggcttactacccaaggacatagccaa cagatctatgaagtgatgaaaaacatccccactttatagatgatttgaca ttaggtatagcacaatcactaccagaggtggcagtagagttgaagggata ttgcaggattgatatgaatgcctatggtgcagggcaagtgatgttacggt ggggagtcttagcaaaatcagttaaaaatattatgttaggacatgctagt gtgcaagcagaaatggaacaagttgagaggatatgaatatgcccaaaaat tgggtggtgaagcaggattctaccatatattgaacaacccaaaagcatca ttattatcatgactcaatacctcacactccagtgtagtattaggcaatgc tgctggcctaggcataatgggagagtacagaggtacaccgaggaatcaag atctatatgatgcagcaaaggcatatgctgaacaactcaaagaaaatggt gtgattaactacagtgtactagacttgacagcagaagaactagaggctat caaacatcagcttaatccaaaagataatgatgtagagattgagttaataa aaaatggggcaaataaatcatcatggaaaagtagctcctgaattccatgg agaagatgcaaacaacagggctactaaaattcctagaatcaataaagggca aattcacatcacccaaagatcccaagaaaaagatagtatcatatctgtc aactcaatagatatagaagtaaccaaagaaagccctataacatcaaattc aactattatcaacccaacaaatgagacagatgatactgcagggaacaagc ccaattatcaaagaaaacctctagtaagatcaaagaagaccctacaccaa -continued gtgataatccatactaaactatacaaagaaaccatagaaacatttgataa caatgaagaagaatccagctattcatacgaagaaataaatgatcagacaa acgataatataacagcaagattagataggattgatgaaaaattaagtgaa atactaggaatgcttcacacattagtagtggcaagtgcaggacctacatc tgctcgggatggtataagagatgccatgattggataagagaagaaatgat agaaaaaatcagaactgaagcattaatgaccaatgacagattagaagcta tggcaagactcaggaatgaggaaagtgaaaagatggcaaaagacacatca gatgaagtgtctctcaatccaacatcagagaaattgaacaacctattgga agggaatgatagtgacaatgatctatcacttgaagatactgattagttac cactatcacatcaacacacaataccaacagaagaccaacaaactaaccaa cccaatcatccaaccaaacatccatccgccaatcagccaaacagccaaca aaacaaccagccaatccaaaactaaccacccggaaaaaatctataatata gttacaaaaaaggaaagggtggggcaaatatggaaacatacgtgaacaa gcttcacgaaggctccacatacacagctgctgttcaatacaatgtcttag aaaaagacgatgaccctgcatcacttacaatatgggtgcccatgttccaa tcatctatgccagcagatttacttataaaagaactagctaatgtcaacat actagtgaaacaaatatccacacccaagggaccacactaagagtcatgat aaactcaagaagtgcagtgctagcacaaatgcccagcaaatttaccatat gcgctaatgtgtccaggatgaaagaagcaaactagcatatgatgtaacca cacctgtgaaatcaaggcatgtagtctaacatgcctaaaatcaaaaaat atgagactacagttaaagatctcactatgaagcactcaaccctacacat gatattattgattatgtgaatttgaaaacatagtaa

---

It is claimed:

1. A recombinant infectious respiratory syncytial virus comprising a large polymerase protein (L), phosphoprotein (P), nucleocapsid protein (N) and a M2-1 protein and a genome or antigenome having a deletion of the codon that encodes the serine at position 1313, or a corresponding position, of the L protein, and optionally comprises non- structural protein 1 (NS1), nonstructural protein 2 (NS2), glycoprotein (G), fusion protein (F), matrix protein (M), M2-2 protein, and small hydrophobic protein (SH).

2. The recombinant infectious respiratory syncytial virus of claim 1, wherein the virus is attenuated.

3. The recombinant infectious respiratory syncytial virus of claim 1, wherein the viral genome or antigenome further comprises a mutation of the codon that encodes the tyrosine at position 1321, or a corresponding position, of the L protein.

4. The recombinant infectious respiratory syncytial virus of claim 1, wherein the viral genome or antigenome further comprises a deletion of the NS2 gene.

5. The recombinant infectious respiratory syncytial virus of claim 1, wherein the viral genome or antigenome further comprises one or more of the following mutations:
the L protein mutation of 1321K, 1321E, 1321P, 1321G, 1321K(AAA), 1321E(GAA), 1321P(CCT), 1321G(GGA), or 1321G(GGT);
the L protein mutation Q831L;
V267I in the N protein, E218A in the F protein, T523 I in the F protein, C319Y in the L protein, and H1690Y in the L protein;
a T to C substitution at the ninth nucleotide position of the gene-start signal of the M2 gene, which corresponds to nucleotide 7606 of a positive sense complement of the genome of RSV strain A2; and
deletion of the SH gene.

6. The recombinant infectious respiratory syncytial virus of claim 1, wherein the viral genome or antigenome further comprises:
a mutation of the codon that encodes the tyrosine at position 1321, or a corresponding position, of the L protein, wherein the mutation of the codon is an AAA mutation.

7. The recombinant infectious respiratory syncytial virus of claim 1, wherein the viral genome or antigenome further comprises:
a mutation of the codon that encodes the tyrosine at position 1321, or a corresponding position, of the L protein, wherein the mutation of the codon is an AAA mutation;
V267I in the N protein, E218A and T523I in the F protein, and C319Y and H1690Y in the L protein; and
a deletion of the SH gene.

8. The recombinant infectious respiratory syncytial virus of claim 1, wherein the viral genome or antigenome further comprises a mutation of amino acid sequence residue 1314, or a corresponding position, of the L protein, wherein the mutation of L protein amino acid sequence residue 1314 is an amino acid substitution of leucine for isoleucine.

9. The recombinant infectious respiratory syncytial virus of claim 8, wherein the mutation of L protein amino acid sequence residue 1314 is encoded by the codon CTG.

10. The recombinant infectious respiratory syncytial virus of claim 8, wherein the virus is attenuated.

11. The recombinant infectious respiratory syncytial virus of claim 8, wherein the viral genome or antigenome further comprises a mutation of the codon that encodes a tyrosine at position 1321, or a corresponding position, of the L protein.

12. The recombinant infectious respiratory syncytial virus of claim 8, wherein the viral genome or antigenome further comprises a deletion of the NS2 gene.

13. The recombinant infectious respiratory syncytial virus of claim 8, wherein the viral genome or antigenome further comprises one or more of the following mutations:
the L protein mutation of 1321K, 1321E, 1321P, 1321G, 1321K(AAA), 1321E(GAA), 1321P(CCT), 1321G(GGA), or 1321G(GGT);
the L protein mutation Q831L;
V267I in the N protein, E218A in the F protein, T523I in the F protein, C319Y in the L protein, and H1690Y in the L protein;
a T to C substitution at the ninth nucleotide position of the gene-start signal of the M2 gene, which corresponds to nucleotide 7606 of a positive sense complement of the genome of RSV strain A2; and
deletion of the SH gene.

14. A method of producing an immune response to a viral protein, comprising administering the respiratory syncytial virus of claim 1 to an animal.

15. The method of claim 14, wherein the respiratory syncytial virus is administered via injection, aerosol delivery, nasal spray, nasal droplets, oral inoculation, or topical application.

16. The method of claim 14, wherein the animal is a mammal.

17. The method of claim 16, wherein the mammal is a human.

18. A recombinant infectious respiratory syncytial virus comprising a large polymerase protein (L), phosphoprotein (P), nucleocapsid protein (N), a M2-1 protein nonstructural protein 1 (NS1), a glycoprotein (G), a fusion protein (F), a matrix protein (M), a M2-2 protein, and a small hydrophobic protein (SH), and a genome or antigenome having:
a deletion of the codon that encodes the serine at position 1313, or a corresponding position, of the L protein,
a mutation of amino acid sequence residue 1314, or a corresponding position, of the L protein, wherein the mutation of L protein amino acid sequence residue 1314 is an amino acid substitution of leucine for isoleucine, wherein the leucine is encoded by a codon set forth as CTG; and
a deletion of the NS2 gene.

19. A method of producing an immune response to a viral protein, comprising administering the respiratory syncytial virus of claim 18 to an animal.

20. The method of claim 19, wherein the respiratory syncytial virus is administered via injection, aerosol delivery, nasal spray, nasal droplets, oral inoculation, or topical application.

21. The method of claim 19, wherein the animal is a mammal.

22. The method of claim 21, wherein the mammal is a human.

* * * * *

SEQUENCE LISTING

<160> NUMBER OF SEQ ID NOS: 48

<210> SEQ ID NO 1
<211> LENGTH: 45
<212> TYPE: DNA
<213> ORGANISM: Human respiratory syncytial virus
<220> FEATURE:
<221> NAME/KEY: CDS
<222> LOCATION: (1)..(45)

<400> SEQUENCE: 1 atg gaa gaa ctc agc ata gga acc ctt ggg tta aca tat gaa aag     45
Met Glu Glu Leu Ser Ile Gly Thr Leu Gly Leu Thr Tyr Glu Lys
1               5                   10                  15

<210> SEQ ID NO 2
<211> LENGTH: 45
<212> TYPE: DNA
<213> ORGANISM: Human respiratory syncytial virus
<220> FEATURE:
<221> NAME/KEY: CDS
<222> LOCATION: (1)..(45)

<400> SEQUENCE: 2 atg gaa gaa ctc tgc ata gga acc ctt ggg tta aca tat gaa aag     45
Met Glu Glu Leu Cys Ile Gly Thr Leu Gly Leu Thr Tyr Glu Lys
1               5                   10                  15

<210> SEQ ID NO 3
<211> LENGTH: 45
<212> TYPE: DNA
<213> ORGANISM: Human respiratory syncytial virus
<220> FEATURE:
<221> NAME/KEY: CDS
<222> LOCATION: (1)..(45)

<400> SEQUENCE: 3

```
atg gaa gaa ctc agc ata gga acc ctt ggg tta aca gaa gaa aag      45
Met Glu Glu Leu Ser Ile Gly Thr Leu Gly Leu Thr Glu Glu Lys
1               5                   10                  15
```

<210> SEQ ID NO 4
<211> LENGTH: 45
<212> TYPE: DNA
<213> ORGANISM: Human respiratory syncytial virus
<220> FEATURE:
<221> NAME/KEY: CDS
<222> LOCATION: (1)..(45)

<400> SEQUENCE: 4

```
atg gaa gaa ctc tgc ata gga acc ctt ggg tta aca gaa gaa aag      45
Met Glu Glu Leu Cys Ile Gly Thr Leu Gly Leu Thr Glu Glu Lys
1               5                   10                  15
```

<210> SEQ ID NO 5
<211> LENGTH: 45
<212> TYPE: DNA
<213> ORGANISM: Human respiratory syncytial virus
<220> FEATURE:
<221> NAME/KEY: CDS
<222> LOCATION: (1)..(45)

<400> SEQUENCE: 5

```
atg gaa gaa ctc agc ata gga acc ctt ggg tta aca aaa gaa aag      45
Met Glu Glu Leu Ser Ile Gly Thr Leu Gly Leu Thr Lys Glu Lys
1               5                   10                  15
```

<210> SEQ ID NO 6
<211> LENGTH: 45
<212> TYPE: DNA
<213> ORGANISM: Human respiratory syncytial virus
<220> FEATURE:
<221> NAME/KEY: CDS
<222> LOCATION: (1)..(45)

<400> SEQUENCE: 6

```
atg gaa gaa ctc tgc ata gga acc ctt ggg tta aca aaa gaa aag      45
Met Glu Glu Leu Cys Ile Gly Thr Leu Gly Leu Thr Lys Glu Lys
1               5                   10                  15
```

<210> SEQ ID NO 7
<211> LENGTH: 45
<212> TYPE: DNA
<213> ORGANISM: Human respiratory syncytial virus
<220> FEATURE:
<221> NAME/KEY: CDS
<222> LOCATION: (1)..(45)

<400> SEQUENCE: 7

```
atg gaa gaa ctc agc ata gga acc ctt ggg tta aca gga gaa aag      45
Met Glu Glu Leu Ser Ile Gly Thr Leu Gly Leu Thr Gly Glu Lys
1               5                   10                  15
```

<210> SEQ ID NO 8
<211> LENGTH: 45
<212> TYPE: DNA

```
<213> ORGANISM: Human respiratory syncytial virus
<220> FEATURE:
<221> NAME/KEY: CDS
<222> LOCATION: (1)..(45)

<400> SEQUENCE: 8 atg gaa gaa ctc tgc ata gga acc ctt ggg tta aca gga gaa aag      45
Met Glu Glu Leu Cys Ile Gly Thr Leu Gly Leu Thr Gly Glu Lys
1               5                   10                  15

<210> SEQ ID NO 9
<211> LENGTH: 45
<212> TYPE: DNA
<213> ORGANISM: Human respiratory syncytial virus
<220> FEATURE:
<221> NAME/KEY: CDS
<222> LOCATION: (1)..(45)

<400> SEQUENCE: 9 atg gaa gaa ctc agc ata gga acc ctt ggg tta aca ggt gaa aag      45
Met Glu Glu Leu Ser Ile Gly Thr Leu Gly Leu Thr Gly Glu Lys
1               5                   10                  15

<210> SEQ ID NO 10
<211> LENGTH: 45
<212> TYPE: DNA
<213> ORGANISM: Human respiratory syncytial virus
<220> FEATURE:
<221> NAME/KEY: CDS
<222> LOCATION: (1)..(45)

<400> SEQUENCE: 10 atg gaa gaa ctc tgc ata gga acc ctt ggg tta aca ggt gaa aag      45
Met Glu Glu Leu Cys Ile Gly Thr Leu Gly Leu Thr Gly Glu Lys
1               5                   10                  15

<210> SEQ ID NO 11
<211> LENGTH: 15
<212> TYPE: PRT
<213> ORGANISM: Human respiratory syncytial virus

<400> SEQUENCE: 11

Met Glu Glu Leu Ser Ile Gly Thr Leu Gly Leu Thr Tyr Glu Lys
1               5                   10                  15

<210> SEQ ID NO 12
<211> LENGTH: 15
<212> TYPE: PRT
<213> ORGANISM: Human respiratory syncytial virus

<400> SEQUENCE: 12

Met Glu Glu Leu Cys Ile Gly Thr Leu Gly Leu Thr Tyr Glu Lys
1               5                   10                  15

<210> SEQ ID NO 13
<211> LENGTH: 15
<212> TYPE: PRT
<213> ORGANISM: Human respiratory syncytial virus

<400> SEQUENCE: 13

Met Glu Glu Leu Ser Ile Gly Thr Leu Gly Leu Thr Glu Glu Lys
1               5                   10                  15

<210> SEQ ID NO 14
<211> LENGTH: 15
<212> TYPE: PRT
<213> ORGANISM: Human respiratory syncytial virus
```

<400> SEQUENCE: 14

Met Glu Glu Leu Cys Ile Gly Thr Leu Gly Leu Thr Glu Glu Lys
1               5                   10                  15

<210> SEQ ID NO 15
<211> LENGTH: 15
<212> TYPE: PRT
<213> ORGANISM: Human respiratory syncytial virus

<400> SEQUENCE: 15

Met Glu Glu Leu Ser Ile Gly Thr Leu Gly Leu Thr Lys Glu Lys
1               5                   10                  15

<210> SEQ ID NO 16
<211> LENGTH: 15
<212> TYPE: PRT
<213> ORGANISM: Human respiratory syncytial virus

<400> SEQUENCE: 16

Met Glu Glu Leu Cys Ile Gly Thr Leu Gly Leu Thr Lys Glu Lys
1               5                   10                  15

<210> SEQ ID NO 17
<211> LENGTH: 15
<212> TYPE: PRT
<213> ORGANISM: Human respiratory syncytial virus

<400> SEQUENCE: 17

Met Glu Glu Leu Ser Ile Gly Thr Leu Gly Leu Thr Gly Glu Lys
1               5                   10                  15

<210> SEQ ID NO 18
<211> LENGTH: 15
<212> TYPE: PRT
<213> ORGANISM: Human respiratory syncytial virus

<400> SEQUENCE: 18

Met Glu Glu Leu Cys Ile Gly Thr Leu Gly Leu Thr Gly Glu Lys
1               5                   10                  15

<210> SEQ ID NO 19
<211> LENGTH: 36
<212> TYPE: DNA
<213> ORGANISM: Human respiratory syncytial virus
<220> FEATURE:
<221> NAME/KEY: CDS
<222> LOCATION: (1)..(36)

<400> SEQUENCE: 19 gaa ctc tca ata gga acc ctt ggg tta aca aaa gaa      36
Glu Leu Ser Ile Gly Thr Leu Gly Leu Thr Lys Glu
1               5                   10

<210> SEQ ID NO 20
<211> LENGTH: 42
<212> TYPE: DNA
<213> ORGANISM: Human respiratory syncytial virus
<220> FEATURE:
<221> NAME/KEY: CDS
<222> LOCATION: (1)..(42)

<400> SEQUENCE: 20 atg gaa gaa ctc ata gga acc ctt ggg tta aca tat gaa aag      42
Met Glu Glu Leu Ile Gly Thr Leu Gly Leu Thr Tyr Glu Lys
1               5                   10

<210> SEQ ID NO 21
<211> LENGTH: 14
<212> TYPE: PRT
<213> ORGANISM: Human respiratory syncytial virus

<400> SEQUENCE: 21

Met Glu Glu Leu Ile Gly Thr Leu Gly Leu Thr Tyr Glu Lys
1               5                   10

<210> SEQ ID NO 22
<211> LENGTH: 4
<212> TYPE: PRT
<213> ORGANISM: Human respiratory syncytial virus

<400> SEQUENCE: 22

Glu Leu Ile Gly
1

<210> SEQ ID NO 23
<211> LENGTH: 12
<212> TYPE: DNA
<213> ORGANISM: Human respiratory syncytial virus
<220> FEATURE:
<221> NAME/KEY: CDS
<222> LOCATION: (1)..(12)

<400> SEQUENCE: 23 gaa ctc ata gga                                                          12
Glu Leu Ile Gly
1

<210> SEQ ID NO 24
<211> LENGTH: 4
<212> TYPE: PRT
<213> ORGANISM: Human respiratory syncytial virus

<400> SEQUENCE: 24

Glu Leu Thr Gly
1

<210> SEQ ID NO 25
<211> LENGTH: 12
<212> TYPE: DNA
<213> ORGANISM: Human respiratory syncytial virus
<220> FEATURE:
<221> NAME/KEY: CDS
<222> LOCATION: (1)..(12)

<400> SEQUENCE: 25 gaa ctc aca gga                                                          12
Glu Leu Thr Gly
1

<210> SEQ ID NO 26
<211> LENGTH: 9
<212> TYPE: PRT
<213> ORGANISM: Human respiratory syncytial virus

<400> SEQUENCE: 26

Glu Leu Thr Gly Thr Leu Gly Leu Thr
1               5

<210> SEQ ID NO 27
<211> LENGTH: 27
<212> TYPE: DNA
<213> ORGANISM: Human respiratory syncytial virus

```
<220> FEATURE:
<221> NAME/KEY: CDS
<222> LOCATION: (1)..(27)

<400> SEQUENCE: 27 gaa ctc aca gga acc ctt ggg tta aca                           27
Glu Leu Thr Gly Thr Leu Gly Leu Thr
1               5

<210> SEQ ID NO 28
<211> LENGTH: 9
<212> TYPE: PRT
<213> ORGANISM: Human respiratory syncytial virus

<400> SEQUENCE: 28

Glu Leu Leu Gly Thr Leu Gly Leu Thr
1               5

<210> SEQ ID NO 29
<211> LENGTH: 27
<212> TYPE: DNA
<213> ORGANISM: Human respiratory syncytial virus
<220> FEATURE:
<221> NAME/KEY: CDS
<222> LOCATION: (1)..(27)

<400> SEQUENCE: 29 gaa ctc ctg gga acc ctt ggg tta aca                           27
Glu Leu Leu Gly Thr Leu Gly Leu Thr
1               5

<210> SEQ ID NO 30
<211> LENGTH: 9
<212> TYPE: PRT
<213> ORGANISM: Human respiratory syncytial virus

<400> SEQUENCE: 30

Glu Leu Ser Gly Thr Leu Gly Leu Thr
1               5

<210> SEQ ID NO 31
<211> LENGTH: 27
<212> TYPE: DNA
<213> ORGANISM: Human respiratory syncytial virus
<220> FEATURE:
<221> NAME/KEY: CDS
<222> LOCATION: (1)..(27)

<400> SEQUENCE: 31 gaa ctc agc gga acc ctt ggg tta aca                           27
Glu Leu Ser Gly Thr Leu Gly Leu Thr
1               5

<210> SEQ ID NO 32
<211> LENGTH: 9
<212> TYPE: PRT
<213> ORGANISM: Human respiratory syncytial virus

<400> SEQUENCE: 32

Glu Leu Ser Ile Gly Leu Gly Leu Thr
1               5

<210> SEQ ID NO 33
<211> LENGTH: 27
<212> TYPE: DNA
<213> ORGANISM: Human respiratory syncytial virus
<220> FEATURE:
```

```
<221> NAME/KEY: CDS
<222> LOCATION: (1)..(27)

<400> SEQUENCE: 33 gaa ctc agc ata gga ctt ggg tta aca                          27
Glu Leu Ser Ile Gly Leu Gly Leu Thr
1               5

<210> SEQ ID NO 34
<211> LENGTH: 9
<212> TYPE: PRT
<213> ORGANISM: Human respiratory syncytial virus

<400> SEQUENCE: 34

Glu Leu Ser Ile Gly Thr Leu Gly Leu
1               5

<210> SEQ ID NO 35
<211> LENGTH: 27
<212> TYPE: DNA
<213> ORGANISM: Human respiratory syncytial virus
<220> FEATURE:
<221> NAME/KEY: CDS
<222> LOCATION: (1)..(27)

<400> SEQUENCE: 35 gaa ctc agc ata gga acc ctt ggg tta                          27
Glu Leu Ser Ile Gly Thr Leu Gly Leu
1               5

<210> SEQ ID NO 36
<211> LENGTH: 21
<212> TYPE: PRT
<213> ORGANISM: Human respiratory syncytial virus

<400> SEQUENCE: 36

Pro Leu Leu Ser Asn Lys Lys Leu Ile Lys Ser Ser Ala Met Ile Arg
1               5                   10                  15

Thr Asn Tyr Ser Lys
            20

<210> SEQ ID NO 37
<211> LENGTH: 20
<212> TYPE: PRT
<213> ORGANISM: Human respiratory syncytial virus

<400> SEQUENCE: 37

Pro Leu Leu Ser Asn Lys Lys Leu Ile Lys Ser Ala Met Ile Arg Thr
1               5                   10                  15

Asn Tyr Ser Lys
            20

<210> SEQ ID NO 38
<211> LENGTH: 20
<212> TYPE: PRT
<213> ORGANISM: Human respiratory syncytial virus

<400> SEQUENCE: 38

Pro Leu Leu Ser Asn Lys Lys Leu Ile Lys Ser Ser Met Ile Arg Thr
1               5                   10                  15

Asn Tyr Ser Lys
            20

<210> SEQ ID NO 39
```

<211> LENGTH: 19
<212> TYPE: PRT
<213> ORGANISM: Human respiratory syncytial virus

<400> SEQUENCE: 39

Pro Leu Leu Ser Asn Lys Lys Leu Ile Ser Ala Met Ile Arg Thr Asn
1               5                   10                  15

Tyr Ser Lys

<210> SEQ ID NO 40
<211> LENGTH: 19
<212> TYPE: PRT
<213> ORGANISM: Human respiratory syncytial virus

<400> SEQUENCE: 40

Pro Leu Leu Ser Asn Lys Lys Leu Ile Lys Ala Met Ile Arg Thr Asn
1               5                   10                  15

Tyr Ser Lys

<210> SEQ ID NO 41
<211> LENGTH: 19
<212> TYPE: PRT
<213> ORGANISM: Human respiratory syncytial virus

<400> SEQUENCE: 41

Pro Leu Leu Ser Asn Lys Lys Leu Ile Lys Ser Met Ile Arg Thr Asn
1               5                   10                  15

Tyr Ser Lys

<210> SEQ ID NO 42
<211> LENGTH: 17
<212> TYPE: PRT
<213> ORGANISM: Human respiratory syncytial virus

<400> SEQUENCE: 42

Pro Leu Leu Ser Asn Lys Lys Leu Ile Met Ile Arg Thr Asn Tyr Ser
1               5                   10                  15

Lys

<210> SEQ ID NO 43
<211> LENGTH: 17
<212> TYPE: PRT
<213> ORGANISM: Human respiratory syncytial virus

<400> SEQUENCE: 43

Pro Leu Leu Ser Asn Lys Lys Leu Ile Lys Ile Arg Thr Asn Tyr Ser
1               5                   10                  15

Lys

<210> SEQ ID NO 44
<211> LENGTH: 15
<212> TYPE: PRT
<213> ORGANISM: Human respiratory syncytial virus

<400> SEQUENCE: 44

Pro Leu Leu Ser Asn Lys Lys Leu Ile Arg Thr Asn Tyr Ser Lys
1               5                   10                  15

<210> SEQ ID NO 45
<211> LENGTH: 12
<212> TYPE: PRT
<213> ORGANISM: Human respiratory syncytial virus

<400> SEQUENCE: 45

Pro Leu Leu Ser Asn Ile Arg Thr Asn Tyr Ser Lys
1               5                   10

<210> SEQ ID NO 46
<211> LENGTH: 8
<212> TYPE: PRT
<213> ORGANISM: Human respiratory syncytial virus

<400> SEQUENCE: 46

Pro Leu Leu Ser Asn Lys Lys Leu
1               5

<210> SEQ ID NO 47
<211> LENGTH: 7
<212> TYPE: PRT
<213> ORGANISM: Human respiratory syncytial virus

<400> SEQUENCE: 47

Ile Arg Thr Asn Tyr Ser Lys
1               5

<210> SEQ ID NO 48
<211> LENGTH: 15222
<212> TYPE: DNA
<213> ORGANISM: Human respiratory syncytial virus

<400> SEQUENCE: 48

| | | | | | |
|---|---|---|---|---|---|
| acgcgaaaaa | atgcgtacaa | caaacttgca | taaaccaaaa | aaatggggca | aataagaatt | 60 |
| tgataagtac | cacttaaatt | taactcccct | tggttagaga | tgggcagcaa | ttcattgagta | 120 |
| tgataaaagt | tagattacaa | aatttgtttg | acaatgatga | agtagcattg | ttaaaaataa | 180 |
| catgctatac | tgataaatta | atacatttaa | ctaacgcttt | ggctaaggca | gtgatacata | 240 |
| caatcaaatt | gaatggcatt | gtgtttgtgc | atgttattac | aagtagtgat | atttgcccta | 300 |
| ataataatat | tgtagtaaaa | tccaatttca | caacaatgcc | agtactacaa | aatggaggtt | 360 |
| atatatggga | aatgatggaa | ttaacacatt | gctctcaacc | taatggtcta | ctagatgaca | 420 |
| attgtgaaat | taaattctcc | aaaaaactaa | gtgattcaac | aatgaccaat | tatatgaatc | 480 |
| aattatctga | attacttgga | tttgatctta | atccataaat | tataattaat | atcaactagc | 540 |
| aaatcaatgt | cactaacacc | attagttaat | ataaaactta | acagaagaca | aaaatggggc | 600 |
| aaataaatca | attcagccaa | cccaaccatg | gacacaaccc | acaatgataa | atacaccacaa | 660 |
| agactgatga | tcacagacat | gagaccgttg | tcacttgaga | ccataataac | atcactaacc | 720 |
| agagacatca | taacacacaa | atttatatac | ttgataaatc | atgaatgcat | agtgagaaaa | 780 |
| cttgatgaaa | aacaggccac | atttacattc | ctggtcaact | atgaaatgaa | actattacac | 840 |
| aaagtaggaa | gcactaaata | taaaaaatat | actgaataca | acacaaaata | tggcactttc | 900 |
| cctatgccaa | tattcatcaa | tcatgatggg | ttcttagaat | gcattggcat | taagcctaca | 960 |
| aagcatactc | ccataatata | caagtatgat | ctcaatccat | aaatttcaac | acaatattca | 1020 |
| cacaatctaa | aacaacaact | ctatgcataa | ctatactcca | tagtccagat | ggagcctgaa | 1080 |
| aattatagta | atttaaaatt | aaggagagat | ataagataga | agatggggca | aatacaaaga | 1140 |
| tggctcttag | caaagtcaag | ttgaatgata | cactcaacaa | agatcaactt | ctgtcatcca | 1200 |
| gcaaatacac | catccaacgg | agcacaggag | atagtattga | tactcctaat | tatgatgtgc | 1260 |
| agaaacacat | caataagtta | tgtggcatgt | tattaatcac | agaagatgct | aatcataaat | 1320 |

```
tcactgggtt aataggtatg ttatatgcga tgtctaggtt aggaagagaa gacaccataa    1380
aaatactcag agatgcggga tatcatgtaa aagcaaatgg agtagatgta acaacacatc    1440
gtcaagacat taatggaaaa gaaatgaaat ttgaagtgtt aacattggca agcttaacaa    1500
ctgaaattca aatcaacatt gagatagaat ctagaaaatc ctacaaaaaa atgctaaaag    1560
aaatgggaga ggtagctcca gaatacaggc atgactctcc tgattgtggg atgataatat    1620
tatgtatagc agcattagta ataactaaat tagcagcagg ggacagatct ggtcttacag    1680
ccgtgattag gagagctaat aatgtcctaa aaatgaaat gaaacgttac aaaggcttac     1740
tacccaagga catagccaac agcttctatg aagtgtttga aaaacatccc cactttatag    1800 atgttttttgt tcattttggt atagcacaat cttctaccag aggtggcagt agagttgaag   1860 ggattttttgc aggattgttt atgaatgcct atggtgcagg gcaagtgatg ttacggtggg   1920
gagtcttagc aaaatcagtt aaaaatatta tgttaggaca tgctagtgtg caagcagaaa    1980
tggaacaagt tgttgaggtt tatgaatatg cccaaaaatt gggtggtgaa gcaggattct    2040
accatatatt gaacaaccca aaagcatcat tattatcttt gactcaattt cctcacttct    2100
ccagtgtagt attaggcaat gctgctggcc taggcataat gggagagtac agaggtacac    2160
cgaggaatca agatctatat gatgcagcaa aggcatatgc tgaacaactc aaagaaaatg    2220
gtgtgattaa ctacagtgta ctagacttga cagcagaaga actagaggct atcaaacatc    2280
agcttaatcc aaaagataat gatgtagagc tttgagttaa taaaaatgg ggcaaataaa     2340 tcatcatgga aaagtttgct cctgaattcc atggagaaga tgcaaacaac agggctacta    2400
aattcctaga atcaataaag ggcaaattca catcacccaa agatcccaag aaaaagata     2460 gtatcatatc tgtcaactca atagatatag aagtaaccaa agaaagccct ataacatcaa    2520
attcaactat tatcaaccca acaaatgaga cagatgatac tgcagggaac aagcccaatt    2580
atcaaagaaa acctctagta agtttcaaag aagaccctac accaagtgat aatccctttt    2640
ctaaactata caaagaaacc atagaaacat ttgataacaa tgaagaagaa tccagctatt    2700
catacgaaga aataaatgat cagacaaacg ataatataac agcaagatta gataggattg    2760
atgaaaaatt aagtgaaata ctaggaatgc ttcacacatt agtagtggca agtgcaggac    2820
ctacatctgc tcgggatggt ataagagatg ccatgattgg tttaagagaa gaatgataga    2880
aaaaaatcag aactgaagca ttaatgacca atgcagatt agaagctatg caagactca     2940 ggaatgagga aagtgaaaag atggcaaaag acacatcaga tgaagtgtct ctcaatccaa    3000
catcagagaa attgaacaac ctattggaag ggaatgatag tgacaatgat ctatcacttg    3060
aagatttctg attagttacc actcttcaca tcaacacaca ataccaacag aagaccaaca    3120
aactaaccaa cccaatcatc caaccaaaca tccatccgcc aatcagccaa acagccaaca    3180
aaacaaccag ccaatccaaa actaaccacc cggaaaaaat ctataatata gttacaaaaa    3240
aaggaaaggg tggggcaaat atggaaacat acgtgaacaa gcttcacgaa ggctccacat    3300
acacagctgc tgttcaatac aatgtcttag aaaaagacga tgaccctgca tcacttacaa    3360
tatgggtgcc catgttccaa tcatctatgc cagcagattt acttataaaa gaactagcta    3420
atgtcaacat actagtgaaa caaatatcca cacccaaggg accttcacta agagtcatga    3480
taaactcaag aagtgcagtg ctagcacaaa tgcccagcaa atttaccata tgcgctaatg    3540
tgtccttgga tgaaagaagc aaactagcat atgatgtaac cacaccctgt gaaatcaagg    3600
catgtagtct aacatgccta aaatcaaaaa atatgttgac tacagttaaa gatctcacta    3660
```

```
tgaagacact caaccctaca catgatatta ttgctttatg tgaatttgaa aacatagtaa    3720
catcaaaaaa agtcataata ccaacatacc taagatccat cagtgtcaga aataaagatc    3780
tgaacacact tgaaaatata acaaccactg aattcaaaaa tgctatcaca aatgcaaaaa    3840 tcatcccttta ctcaggatta ctattagtca tcacagtgac tgacaacaaa ggagcattca    3900
aatacataaa gccacaaagt caattcatag tagatcttgg agcttaccta gaaaagaaa    3960 gtatatatta tgttaccaca aattggaagc acacagctac acgatttgca atcaaaccca    4020
tggaagatta acctttttcc tctacatcag tgtgttaatt catacaaact ttctacctac    4080
attcttcact tcaccatcac aatcacaaac actctgtggt tcaaccaatc aaacaaaact    4140
tatctgaagt cccagatcat cccaagtcat tgtttatcag atctagtact caaataagtt    4200
aataaaaaat atacacatgg ggcaaataat cattggagga atccaactaa tcacaatat    4260 ctgttaacat agacaagtcc acacaccata cagaatcaac caatggaaaa tacatccata    4320
acaatagaat tctcaagcaa attctggcct tactttacac taatacacat gatcacaaca    4380
ataatctctt tgctaatcat aatctccatc atgattgcaa tactaaacaa actttgtgaa    4440
tataacgtat tccataacaa aacctttgag ttaccaagag ctcgagtcaa cacatagcat    4500
tcatcaatcc aacagcccaa aacagtaacc ttgcatttaa aaatgaacaa cccctacctc    4560
tttacaacac ctcattaaca tcccaccatg caaaccacta tccatactat aaagtagtta    4620
attaaaaata gtcataacaa tgaactagga tatcaagact aacaataaca ttggggcaaa    4680
tgcaaacatg tccaaaaaca aggaccaacg caccgctaag acattagaaa ggacctggga    4740
cactctcaat catttattat tcatatcatc gtgcttatat aagttaaatc ttaaatctgt    4800
agcacaaatc acattatcca ttctggcaat gataatctca acttcactta taattgcagc    4860
catcatattc atagcctcgg caaaccacaa agtcacacca caactgcaa tcatacaaga    4920 tgcaacaagc cagatcaaga acacaacccc aacatacctc acccagaatc ctcagcttgg    4980
aatcagtccc tctaatccgt ctgaaattac atcacaaatc accaccatac tagcttcaac    5040
aacaccagga gtcaagtcaa ccctgcaatc cacaacagtc aagaccaaaa acacaacaac    5100
aactcaaaca caacccagca agcccaccac aaaaacaacg caaaacaaac caccaagcaa    5160
acccaataat gattttcact ttgaagtgtt caactttgta ccctgcagca tatgcagcaa    5220
caatccaacc tgctgggcta tctgcaaaag aataccaaac aaaaaaccag gaaagaaaac    5280
cactaccaag cccacaaaaa aaccaaccct caagacaacc aaaaaagatc ccaaacctca    5340
aaccactaaa tcaaaggaag tacccaccac caagcccaca gaagagccaa ccatcaacac    5400
caccaaaaca aacatcataa ctacactact cacctccaac accacaggaa atccagaact    5460
cacaagtcaa atggaaacct tccactcaac ttcctccgaa ggcaatccaa gcccttctca    5520
agtctctaca acatccgagt acccatcaca accttcatct ccacccaaca caccacgcca    5580
gtagttactt aaaaacatat tatcacaaaa agccatgacc aacttaaaca gaatcaaaat    5640
aaactctggg gcaaataaca atggagttgc taatcctcaa agcaaatgca attaccacaa    5700
tcctcactgc agtcacattt tgttttgctt ctggtcaaaa catcactgaa gaattttatc    5760
aatcaacatg cagtgcagtt agcaaaggct atcttagtgc tctgagaact ggttggtata    5820
ccagtgttat aactatagaa ttaagtaata tcaaggaaaa taagtgtaat ggaacagatg    5880
ctaaggtaaa attgataaaa caagaattag ataaatataa aaatgctgta acagaattgc    5940
agttgctcat gcaaagcaca ccaccaacaa acaatcgagc cagaagagaa ctaccaaggt    6000
ttatgaatta tacactcaac aatgccaaaa aaaccaatgt aacattaagc aagaaaagga    6060
```

```
aaagaagatt tcttgttttt ttgttaggtg ttggatctgc aatcgccagt ggcgttgctg    6120
tatctaaggt cctgcaccta aaggggaag tgaacaagat caaaagtgct ctactatcca    6180
caaacaaggc tctagtcagc ttatcaaatg gagttagtgt cttaaccagc aaagtgttag    6240
acctcaaaaa ctatatagat aaacaattgt tacctattgt gaacaagcaa agctgcagca    6300
tatcaaatat agaaactgtg atagagttcc aacaaagaa caacagacta ctagagatta    6360
ccagggaatt tagtgttaat gcaggtgtaa ctacacctgt aagcacttac atgttaacta    6420
atagtgaatt attgtcatta atcaatgata tgcctataac aaatgatcag aaaaagttaa    6480
tgtccaacaa tgttcaaata gttagacagc aaagttactc tatcatgtcc ataataaaag    6540
aggaagtctt agcatatgta gtacaattac cactatatgg tgttatagat acaccctgtt    6600
ggaaactaca cacatcccct ctatgtacaa ccaacacaaa agaagggtcc aacatctgtt    6660
taacaagaac tgacagagga tggtactgtg acaatgcagg atcagtatct ttcttcccac    6720
aagctgaaac atgtaaagtt caatcaaatc gagtattttg tgacacaatg aacagtttaa    6780
cattaccaag tgaaataaat ctctgcaatg ttgacatatt caaccccaaa tatgattgta    6840
aaattatgac ttcaaaaaca gatgtaagca gctccgttat cacatctcta ggagccattg    6900
tgtcatgcta tggcaaaact aaatgtacag catccaataa aaatcgtgga atcataaaga    6960
cattttctaa cggtgcgat tatgtatcaa ataaagggat ggacactgtg tctgtaggta    7020
acacattata ttatgtaaat aagcaagaag gtaaaagtct ctatgtaaaa ggtgaaccaa    7080
taataaattt ctatgaccca ttagtattcc cctctgatga atttgatgca tcaatatctc    7140
aagtcaacga gaagattaac cagagcctag catttattcg taaatccgat gaattattac    7200
ataatgtaaa tgctggtaaa tccaccacaa atatcatgat aactactata attatagtga    7260
ttatagtaat attgttatca ttaattgctg ttggactgct cttatactgt aaggccagaa    7320
gcacaccagt cacactaagc aaagatcaac tgagtggtat aaataatatt gcatttagta    7380
actaaataaa aatagcacct aatcatgttc ttacaatggt ttactatctg ctcatagaca    7440
acccatctgt cattggattt tcttaaaatc tgaacttcat cgaaactctc atctataaac    7500
catctcactt acactattta gtagattcc tagtttatag ttatataaaa cacaattgaa    7560
tgccagatta acttaccatc tgtaaaaatg aaaactgggg caaatatgtc acgaaggaat    7620
ccttgcaaat ttgaaattcg aggtcattgc ttaaatggta agaggtgtca ttttagtcat    7680
aattattttg aatggccacc ccatgcactg cttgtaagac aaaactttat gttaaacaga    7740
atacttaagt ctatggataa aagtatagat accttatcag aaataagtgg agctgcagag    7800
ttggacagaa cagaagagta tgctcttggt gtagttggag tgctagagag ttatataqga    7860 tcaataaaca atataactaa acaatcagca tgtgttgcca tgagcaaact cctcactgaa    7920
ctcaatagtg atgatatcaa aaagctgagg gacaatgaag agctaaattc acccaagata    7980
agagtgtaca atactgtcat atcatatatt gaaagcaaca ggaaaaacaa taaacaaact    8040
atccatctgt taaaagatt gccagcagac gtattgaaga aaccatcaa aaacacattg    8100 gatatccata agagcataac catcaacaac ccaaaagaat caactgttag tgatacaaat    8160
gaccatgcca aaaataatga tactacctga caaatatcct tgtagtataa cttccatact    8220
aataacaagt agatgtagag ttactatgta taatcaaaag aacacactat atttcaatca    8280
aaacaaccca ataaccata tgtactcacc gaatcaaaca ttcaatgaaa tccattggac    8340
ctctcaagaa ttgattgaca caattcaaat ttttctacaa catctaggta ttattgagga    8400
```

```
tatatataca atatatatat tagtgtcata acactcaatt ctaacactca ccacatcgtt    8460
acattattaa ttcaaacaat tcaagttgtg ggacaaaatg gatcccatta ttaatggaaa    8520
ttctgctaat gtttatctaa ccgatagtta tttaaaaggt gttatctctt tctcagagtg    8580
taatgcttta ggaagttaca tattcaatgg tccttatctc aaaaatgatt ataccaactt    8640
aattagtaga caaatccat taatagaaca catgaatcta agaaactaa atataacaca      8700 gtccttaata tctaagtatc ataaaggtga aataaaatta gaagaaccta cttattttca    8760
gtcattactt atgacataca agagtatgac ctcgtcagaa cagattgcta ccactaattt    8820
acttaaaaag ataataagaa gagctataga aataagtgat gtcaaagtct atgctatatt    8880
gaataaacta gggcttaaag aaaaggacaa gattaaatcc aacaatggac aagatgaaga    8940
caactcagtt attacgacca taatcaaaga tgatatactt tcagctgtta aagataatca    9000
atctcatctt aaagcagaca aaaatcactc tacaaaacaa aaagacacaa tcaaaacaac    9060
actcttgaag aaattgatgt gttcaatgca acatcctcca tcatggttaa tacattggtt    9120
taacttatac acaaaattaa acaacatatt aacacagtat cgatcaaatg aggtaaaaaa    9180
ccatgggttt acattgatag ataatcaaac tcttagtgga tttcaattta ttttgaacca    9240
atatggttgt atagtttatc ataaggaact caaaagaatt actgtgacaa cctataatca    9300
attcttgaca tggaaagata ttagccttag tagattaaat gtttgtttaa ttacatggat    9360
tagtaactgc ttgaacacat taaataaaag cttaggctta agatgcggat tcaataatgt    9420
tatcttgaca caactattcc tttatggaga ttgtatacta aagctatttc acaatgaggg    9480
gttctacata ataaaagagg tagagggatt tattatgtct ctaattttaa atataacaga    9540
agaagatcaa ttcagaaaac gattttataa tagtatgctc aacaacatca cagatgctgc    9600
taataaagct cagaaaaatc tgctatcaag agtatgtcat acattattag ataagacagt    9660
gtccgataat ataataaatg gcagatggat aattctatta agtaagttcc ttaaattaat    9720
taagcttgca ggtgacaata accttaacaa tctgagtgaa ctatatttt tgttcagaat    9780 atttggacac ccaatggtag atgaaagaca agccatggat gctgttaaaa ttaattgcaa    9840
tgagaccaaa ttttacttgt taagcagtct gagtatgtta agaggtgcct ttatatatag    9900
aattataaaa gggtttgtaa ataattacaa cagatggcct actttaagaa atgctattgt    9960 tttacccctta agatggttaa cttactataa actaaacact tatccttctt tgttggaact   10020
tacagaaaga gatttgattg tgttatcagg actacgtttc tatcgtgagt ttcggttgcc   10080
taaaaaagtg gatcttgaaa tgattataaa tgataaagct atatcacctc ctaaaaattt   10140
gatatggact agtttcccta gaattacat gccatcacac atacaaaact atatagaaca    10200
tgaaaaatta aaattttccg agagtgataa atcaagaaga gtattagagt attatttaag   10260
agataacaaa ttcaatgaat gtgatttata caactgtgta gttaatcaaa gttatctcaa   10320
caaccctaat catgtggtat cattgacagg caaagaaaga gaactcagtg taggtagaat   10380
gtttgcaatg caaccgggaa tgttcagaca ggttcaaata ttggcagaga aaatgatagc   10440
tgaaaacatt ttacaattct ttcctgaaag tcttacaaga tatggtgatc tagaactaca   10500
aaaaatatta gaattgaaag caggaataag taacaaatca aatcgctaca atgataatta   10560
caacaattac attagtaagt gctctatcat cacagatctc agcaaattca atcaagcatt   10620
tcgatatgaa acgtcatgta tttgtagtga tgtgctggat gaactgcatg gtgtacaatc   10680 tctatttttcc tggttacatt taactattcc tcatgtcaca ataatatgca catataggca   10740 tgcaccccc tatataggag atcatattgt agatcttaac aatgtagatg aacaaagtgg   10800
```

```
attatataga tatcacatgg gtggcatcga agggtggtgt caaaaactgt ggaccataga    10860
agctatatca ctattggatc taatatctct caaagggaaa ttctcaatta ctgctttaat    10920
taatggtgac aatcaatcaa tagatataag caaaccaatc agactcatgg aaggtcaaac    10980
tcatgctcaa gcagattatt tgctagcatt aaatagcctt aaattactgt ataaagagta    11040
tgcaggcata ggccacaaat taaaaggaac tgagacttat atatcacgag atatgcaatt    11100
tatgagtaaa acaattcaac ataacggtgt atattaccca gctagtataa agaaagtcct    11160
aagagtggga ccgtggataa acactatact tgatgatttc aaagtgagtc tagaatctat    11220
aggtagtttg acacaagaat tagaatatag aggtgaaagt ctattatgca gtttaatatt    11280
tagaaatgta tggttatata atcagattgc tctacaatta aaaaatcatg cattatgtaa    11340
caataaacta tatttggaca tattaaaggt tctgaaacac ttaaaaacct tttttaatct    11400
tgataatatt gatacagcat taacattgta tatgaattta cccatgttat tggtggtgg     11460 tgatcccaac ttgttatatc gaagtttcta tagaagaact cctgacttcc tcacagaggc    11520
tatagttcac tctgtgttca tacttagtta ttatacaaac catgacttaa aagataaact    11580
tcaagatctg tcagatgata gattgaataa gttcttaaca tgcataatca cgtttgacaa    11640
aaaccctaat gctgaattcg taacattgat gagagatcct caagctttag ggtctgagag    11700
acaagctaaa attactagcg aaatcaatag actggcagtt acagaggttt tgagtacagc    11760
tccaaacaaa atattctcca aaagtgcaca acattatact actacagaga tagatctaaa    11820
tgatattatg caaatatag aacctacata tcctcatggg ctaagagttg tttatgaaag     11880
tttacccttt tataaagcag agaaaatagt aaatcttata tcaggtacaa aatctataac    11940
taacatactg gaaaaaactt ctgccataga cttaacagat attgatagag ccactgagat    12000
gatgaggaaa aacataactt tgcttataag gatacttcca ttggattgta acagagataa    12060
aagagagata ttgagtatgg aaaacctaag tattactgaa ttaagcaaat atgttaggga    12120
aagatcttgg tctttatcca atatagttgg tgttacatca cccagtatca tgtatacaat    12180
ggacatcaaa tatactacaa gcactatatc tagtggcata attatagaga aatataatgt    12240
taacagttta acacgtggtg agagaggacc cactaaacca tgggttggtt catctacaca    12300
agagaaaaaa acaatgccag tttataatag acaagtctta accaaaaaac agagagatca    12360
aatagatcta ttagcaaaat tggattgggt gtatgcatct atagataaca aggatgaatt    12420
catggaagaa ctcagcatag gaaccctggg gttaacatat gaaaaggcca agaaattatt    12480
tccacaatat ttaagtgtca attatttgca tcgccttaca gtcagtagta gaccatgtga    12540
attccctgca tcaataccag cttatagaac aacaaattat cactttgaca ctagccctat    12600
taatcgcata ttaacagaaa gtatggtga tgaagatatt gacatagtat tccaaaactg     12660
tataagcttt ggccttagtt taatgtcagt agtagaacaa tttactaatg tatgtcctaa    12720
cagaattatt ctcatcccta agcttaatga gatacatttg atgaaacctc ccatattcac    12780
aggtgatgtt gatattcaca gttaaaaaca agtgatacaa aaacagcata tgttttacc     12840 agacaaaata agttttgactc aatatgtgga attattctta agtaataaaa cactcaaatc    12900
tggatctcat gttaattcta atttaatatt ggcacataaa atatctgact attttcataa    12960
tacttacatt ttaagtacta atttagctgg acattggatt ctgattatac aacttatgaa    13020
agattctaaa ggtattttg aaaaagattg gggagaggga tatataactg atcatatgtt     13080
tattaatttg aaagttttct tcaatgctta taagacctat ctcttgtgtt ttcataaagg    13140
```

```
ttatggcaaa gcaaagctgg agtgtgatat gaacacttca gatcttctat gtgtattgga    13200
attaatagac agtagttatt ggaagtctat gtctaaggta tttttagaac aaaaagttat    13260
caaatacatt cttagccaag atgcaagttt acatagagta aaaggatgtc atagcttcaa    13320
attatggttt cttaaacgtc ttaatgtagc agaattcaca gtttgccctt ggggttgttaa   13380 catagattat catccaacac atatgaaagc aatattaact tatatagatc ttgttagaat    13440
gggattgata aatatagata gaatacacat taaaaataaa cacaaattca atgatgaatt    13500
ttatacttct aatctcttct acattaatta taacttctca gataatactc atctattaac    13560
taaacatata aggattgcta attctgaatt agaaaataat tacaacaaat tatatcatcc    13620
tacaccagaa accctagaga atatactagc caatccgatt aaaagtaatg acaaaaagac    13680
actgaatgac tattgtatag gtaaaaatgt tgactcaata atgttaccat tgttatctaa    13740
taagaagctt attaaatcgt ctgcaatgat tagaaccaat tacagcaaac aagatttgta    13800
taatttattc cctatggttg tgattgatag aattatagat cattcaggca atacagccaa    13860
atccaaccaa ctttacacta ctacttccca ccaaatatct ttagtgcaca atagcacatc    13920
actttactgc atgcttcctt ggcatcatat taatagattc aattttgtat ttagttctac    13980
aggttgtaaa attagtatag agtatatttt aaaagatctt aaaattaaag atcccaattg    14040
tatagcattc ataggtgaag gagcagggaa tttattattg cgtacagtag tggaacttca    14100
tcctgacata agatatattt acagaagtct gaaagattgc aatgatcata gtttacctat    14160
tgagttttta aggctgtaca atggacatat caacattgat tatggtgaaa atttgaccat    14220
tcctgctaca gatgcaacca acaacattca ttggtcttat ttacatataa agtttgctga    14280
acctatcagt cttttttgtct gtgatgccga attgtctgta acagtcaact ggagtaaaat    14340
tataatagaa tggagcaagc atgtaagaaa gtgcaagtac tgttcctcag ttaataaatg    14400
tatgttaata gtaaaatatc atgctcaaga tgatattgat ttcaaattag acaatataac    14460
tatattaaaa acttatgtat gcttaggcag taagttaaag ggatcggagg tttacttagt    14520
ccttacaata ggtcctgcga atatattccc agtatttaat gtagtacaaa atgctaaatt    14580
gatactatca agaaccaaaa atttcatcat gcctaagaaa gctgataaag agtctattga    14640
tgcaaatatt aaaagtttga tacccttttct ttgttaccct ataacaaaaa aaggaattaa    14700
tactgcattg tcaaaactaa agagtgttgt tagtggagat atactatcat attctatagc    14760
tggacgtaat gaagttttca gcaataaact tataaatcat aagcatatga acatcttaaa    14820
atggttcaat catgttttaa atttcagatc aacagaacta aactataacc atttatatat    14880
ggtagaatct acatatcctt acctaagtga attgttaaac agcttgacaa ccaatgaact    14940
taaaaaactg attaaaatca caggtagtct gttatacaac tttcataatg aataatgaat    15000
aaagatctta taataaaaat tcccatagct atacactaac actgtattca attatagtta   15060
ttaaaaatta aaaatcatat aatttttta ataacttta gtgaactaat cctaaagtta    15120
tcattttaat cttggaggaa taaatttaaa ccctaatcta attggtttat atgtgtatta    15180
actaaattac gagatattag tttttgacac ttttttttctc gt                      15222
```